US011247985B2

(12) United States Patent
Huryn et al.

(10) Patent No.: US 11,247,985 B2
(45) Date of Patent: Feb. 15, 2022

(54) PHENYL INDOLE ALLOSTERIC INHIBITORS OF P97 ATPASE

(71) Applicants: University of Pittsburgh—Of the Commonwealth System of Higher Education, Pittsburgh, PA (US); National Institutes of Health, A Component of the United States Department of Health and Human Services, Bethesda, MD (US); The Regents of the University of California, Oakland, CA (US)

(72) Inventors: Donna M. Huryn, Allentown, NJ (US); Peter Wipf, Pittsburgh, PA (US); Matthew G. LaPorte, Pittsburgh, PA (US); Raffaele Colombo, Pittsburgh, PA (US); Marina Kovaliov, Pittsburgh, PA (US); Chaemin Lim, Pittsburgh, PA (US); Celeste Natalie Alverez, Pittsburgh, PA (US); Zhizhou Yue, Pittsburgh, PA (US); Lalith Palitha Samankumara, Pittsburgh, PA (US); Alexander Julian Chatterley, Pittsburgh, PA (US); Yongzhao Yan, Pittsburgh, PA (US); Mary Liang, Pittsburgh, PA (US); Neal J. Green, Newton, MA (US); Eric T. Baldwin, Upper Holland, PA (US); William J. Moore, Hagerstown, MD (US); Michelle Arkin, San Francisco, CA (US); R. Jeffrey Neitz, Oakland, CA (US); Kean-Hooi Ang, Oakland, CA (US); Clifford Bryant, Oakland, CA (US); Stacie Bulfer, Oakland, CA (US)

(73) Assignees: University of Pittsburgh—Of the Commonwealth System of Higher Education, Pittsburgh, PA (US); National Institutes of Health, A Component of the U.S. Department of Hearth and Human Services, Bethesda, MD (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/748,654

(22) Filed: Jan. 21, 2020

(65) Prior Publication Data
US 2020/0157082 A1   May 21, 2020

Related U.S. Application Data

(62) Division of application No. 15/769,987, filed as application No. PCT/US2016/057869 on Oct. 20, 2016, now Pat. No. 10,633,370.

(60) Provisional application No. 62/244,497, filed on Oct. 21, 2015.

(51) Int. Cl.
| C07D 401/10 | (2006.01) |
| A61P 35/00 | (2006.01) |
| C07D 405/14 | (2006.01) |
| C07D 401/14 | (2006.01) |
| A61P 25/28 | (2006.01) |
| C07D 413/14 | (2006.01) |
| C07D 417/14 | (2006.01) |

(52) U.S. Cl.
CPC ........... *C07D 405/14* (2013.01); *A61P 25/28* (2018.01); *A61P 35/00* (2018.01); *C07D 401/10* (2013.01); *C07D 401/14* (2013.01); *C07D 413/14* (2013.01); *C07D 417/14* (2013.01)

(58) Field of Classification Search
CPC ........ C07D 405/14; A61P 35/00; A61P 25/28
See application file for complete search history.

(56) References Cited

U.S. PATENT DOCUMENTS

2011/2755628    11/2011  Yamagishi et al.

FOREIGN PATENT DOCUMENTS

| WO | WO 2005/105078 A1 | 11/2005 |
| WO | WO 2012/014994 A1 | 2/2012 |
| WO | WO 2014/015291 A1 | 1/2014 |

OTHER PUBLICATIONS

Chapman et al. Molecules 2015, 20, 3027-3049 . (Year: 2015).*
Vekaria et al. Frontiers in Oncology,vol. 6, p. 1-8. (Year: 2016).*
Huryn et al. J. Med. Chem. 2020, 63, 1892-1907. (Year: 2020).*
Brandvoid et al., "The chemical biology of molecular chaperones—implications for modulation of proteostasis," *J. Mol. Biol.*, 427(18): 2931-2947 (2015).
Bursavich et al., "2-Anilino-4-aryl-1,3-thiazole inhibitors of valosin-containing protein (VCP or p97)," *Bioorg. Med. Chem. Lett.*, 20:1677-1679 (2010).
Chou et al., "Reversible inhibitor of p97, DBeQ, impairs both ubiquitin-dependent and autophagic protein clearance pathways," *Proc. Natl. Acad. Sci. USA*, 108:4834-4839 (2011).
Chou, et al., "Specific inhibition of p97/VCP atpase and kinetic analysis demonstrate interaction between D1 and D2 ATPase domains." *J. Mol. Biol.* vol. 426, pp. 2886-2899 (2014).
Davies et al., "Improved structures of full-length p97, an AAA ATPase: Implications for mechanisms of nucleotide-dependent conformational change," *Structure*, 76:715-726 (2008).

(Continued)

*Primary Examiner* — Emily A Bernhardt
(74) *Attorney, Agent, or Firm* — Foley & Lardner LLP

(57) ABSTRACT

The present invention is directed to methods of inhibiting p97 and compounds and compositions useful in such methods. Diseases and conditions the can be treated with the compounds and compositions of the invention include, but are not limited to, cancer and neurodegenerative disorders susceptible to treatment by inhibition of p97.

8 Claims, 3 Drawing Sheets

(56) References Cited

OTHER PUBLICATIONS

Deshaies et al., "Proteotoxic crisis, the ubiquitin-proteasome system, and cancer therapy," *BMC Biology*, 72(94), 14 pages (2014).
Fang et al., "Evaluating p97 inhibitor analogues for their domain selectivity and potency against the p97-p47 complex," *ChemMedChem*, 10, pp. 52-56 (2015).
Haines, "P97-containing complexes in proliferation control and cancer: Emerging culprits or guilt by association?" *Genes Cancer*, 1, pp. 753-763 (2010).
Iakobson, et al., "Synthesis of Pentafluorosulfany-Containing Indoles and Oxindoles," *Synlett*.; 24, pp. 855-859 (2013).
Kang et al., "Functional chromatography reveals three natural products that target the same protein with distinct mechanisms of action," *ChemBioChem*, 15, pp. 2125-2131 (2014).
Kumar et al., Copper (II) tetrafluoroborate as a novel and highly efficient catalyst for acetal formation *Tetrahedron Lett.*, 46: pp. 8319-8323 (2005).
Magnaghi et al., "Covalent and allosteric inhibitors of the ATPase VCP/p97 induce cancer cell death," *Nat. Chem. Biol.*, 9, pp. 548-556 (2013).
Manos-Turvey et al., "The effect of structure and mechanism of the Hsp70 chaperone on the ability to identify chemical modulators and therapeutics," *Top. Med. Chem.*, 76, pp. 1-49 (2015).
Meyer et al., "Emerging functions of the VCP/p97 AAA-ATPase in the ubiquitin system," *Nature Cell Biology*, 14: pp. 117-123 (2012).
Meyer et al., "The VCP/p97 system at a glance: connecting cellular function to disease pathogenesis," *J. of Cell Sci.*, 127(18), pp. 3877-3883 (2014).
Polucci et al., "Alkylsulfanyl-1,2,4-triazoles, a new class of allosteric valosine containing protein inhibitors. Synthesis and structure-activity relationships," *J. Med. Chem.*, 56: 437-450 (2013).
Tao et al., "Withaferin A analogs that target the AAA+ chaperone p97," *ACS Chem. Biol.*, 10(8): pp. 1916-1924 (2015).
Tapia, et al., "2,3-Dihydro-2-oxo-1H-benzimidazole-1-carboxamides with selective affinity for the 5-HT(4) receptor: synthesis and structure-affinity and structure-activity relationships of a new series of partial agonist and antagonist derivatives," *A.J. Med. Chem.*, vol. 42, pp. 2870-2880 (1999).
Valle et al., "Critical Role of VCP/p97 in the Pathogenesis and Progression of Non-Small Cell Lung Carcinoma," *PlosOne*, 6(12): e29073, 12 pages (2011).
Walkington, "A Simple Two-Step Synthesis of Indoles," *Synth. Commun.* vol. 33, No. 13, pp. 2229-2233 (2003).
Wang et al., "Inhibition of p97-dependent protein degradation by Eeyarestatin I," *J. Biol. Chem.*, 283:7445-7454 (2008).
Yi et al., "Sorafenib-mediated targeting of the AAA+ ATPase p97/VCP leads to disruption of the secretory pathway, endoplasmic reticulum stress, and hepatocellular cancer cell death," *Mol. Cancer Ther.*, 11:2610-2620 (2012).
Zhang et al., "Structure of the AAA ATPase p97," *Molecular Cell*, 6(6): 1473-1484 (2000).
International Preliminary Report on Patentability issued in related International Patent Application No. PCT/US2016/057869, dated May 3, 2018.
Alverez, et al., "Structure-Activity Study of Bioisosteric Trifluoromethyl and Pentafluorosulfanyl Indole Inhibitors of the AAA ATPase p97," *ACS Medicinal Chemistry Letters*, vol. 6, pp. 1225-1230 (Oct. 2015).
Chemical Abstract compounds, STN express, RN 1212514-22-1 (Entered STN: Mar. 21, 2010); and RNs 1087586-67-1, 1087493-00-2, 1087486-11-0, 1087442-24-7 (Entered STN: Dec. 21, 2008).
Chemical Abstract compounds, STN express, RNs 1586144-91-3, 1585830-69-8 (Entered STN: Apr. 17, 2014); RN 1579457-72-9 (Entered STN: Apr. 3, 2014); RN 1579177-72-2 (Entered STN: Apr. 2, 2014); 1209579-69-0 (Entered STN: Mar. 14, 2010); 1172758-81-4 (Entered STN: Aug. 5, 2009); 1172103-40-0 (Entered STN: Aug. 3, 2009); and RN 1170055-51-2 (Entered STN: Jul. 29, 2009.
International Search Report and Written Opinion issued in related International Patent Application No. PCT/US2016/057869, completed Feb. 21, 2017.
Banerjee et al., Science pp. 1-32 (2016).
Ding et al., Bioorganic & Medicinal Chemistry Letters 26 (2016), pp. 5177-5181 (2016).

\* cited by examiner

PHENYL INDOLE ALLOSTERIC INHIBITORS OF P97 ATPASE

CROSS-REFERENCE TO RELATED APPLICATIONS

This application is a Divisional of U.S. patent application Ser. No. 15/769,987, filed Apr. 20, 2018, now U.S. Pat. No. 10,633,370, and which is the U.S. National Stage of International Patent Application No. PCT/US2016/057869, filed Oct. 20, 2016, which claims priority to U.S. Provisional Patent Application No. 62/244,497, filed Oct. 21, 2015, which all of these applications are incorporated herein by reference in their entirety.

STATEMENT OF GOVERNMENT SUPPORT

This invention was made with government support under HHSN261200800001E awarded by the National Institutes of Health. The government has certain rights in the invention.

BACKGROUND

The AAA ATPase p97 (also known as valosin-containing protein (VCP), Cdc48 in yeast and plants, CDC-48 in worms and Ter94 in flies), is a hexameric member of the AAA family (ATPases associated with diverse cellular activities). Zhang et al., "Structure of the AAA ATPase p97," *Molecular Cell*, 6(6): 1473-84 (2000).

Recent studies have uncovered cellular functions for p97 in autophagy, endosomal sorting and regulating protein degradation at the outer mitochondrial membrane, and elucidated a role for p97 in key chromatin-associated processes. These findings extend the functional relevance of p97 to lysosomal degradation and reveal a dual role in protecting cells from protein stress and ensuring genome stability during proliferation. Meyer et al., "Emerging functions of the VCP/p97 AAA-ATPase in the ubiquitin system," *Nature Cell Biology*, 14: 117-123 (2012).

p97 also functions as an interaction hub, and different sets of at least 30 cofactors have been shown to be responsible for modulating p97-mediated processes. Meyer et al., "The VCP/p97 system at a glance: connecting cellular function to disease pathogenesis," *J. of Cell Sci.*, 127: 1-7 (2014).

p97-associated disease and possible mechanisms: p97 is a potential therapeutic target for cancer and neurodegenerative diseases. Given the crucial role of p97 in maintaining cellular proteostasis, it is not surprising that autosomal dominant mutations in p97, the gene encoding p97, lead to a rare multisystem degenerative disorder previously termed IBMPFD/ALS. The acronym IBMPFD/ALS refers to the four main phenotypes that can affect patients carrying disease-associated mutations of p97 (i.e., inclusion body myopathy (IBM), Paget's disease of the bone (PDB), frontotemporal dementia (FTD) and amyotrophic lateral sclerosis (ALS)). However, a patient with a pathogenic p97 mutation can have any mixture of phenotypes, including all four phenotypes or just one phenotype in isolation. In addition, a member of the same family can have any combination of phenotypes. Id.

Some carriers of p97 mutation also manifest additional symptoms, including Parkinsonism, ataxia, cataracts, dilated cardiomyopathy, hepatic fibrosis, and hearing loss. The term multisystem proteinopathy' has been proposed as the nomenclature for an emerging family of genetic disorders that are unified by this characteristic variation in the penetrance of muscle, bone and CNS degenerative phenotypes along with the accumulation of ubiquitin and TDP-43-positive inclusions.

p97 and cancer: p97 figures prominently in protein quality control as well as serving a variety of other cellular functions associated with cancer. As found for other chaperones, various forms of cancer, including breast, lung, pancreatic, and colorectal cancer, upregulate p97 as a response to accelerated growth and deteriorating protein quality control. See Brandvold et al, "The chemical biology of molecular chaperones—implications for modulation of proteostasis," *J. Mol. Biol.*, 427(18): 2931-2947 (2015); Manos-Turvey et al., "The effect of structure and mechanism of the Hsp70 chaperone on the ability to identify chemical modulators and therapeutics," *Top. Med. Chem.*, 76:1-49 (2015); Deshaies, R. J., "Proteotoxic crisis, the ubiquitin-proteasome system, and cancer therapy," *BMC Biology*, 12: 94/1-94/14 (2014); and Haines, D. S., "P97-containing complexes in proliferation control and cancer: Emerging culprits or guilt by association?" *Genes Cancer*, 1:753-763 (2010). This property might render cancer cells more sensitive to p97 inhibitors than normal cells. In particular, combinations with proteasome or heat shock protein inhibitors could further widen the therapeutic window, but the test of this hypothesis awaits the development of clinically efficacious p97 antagonists.

Several small molecule inhibitors of p97 have been identified. See Davies et al., "Improved structures of full-length p97, an AAA ATPase: Implications for mechanisms of nucleotide-dependent conformational change," *Structure*, 76:715-726 (2008). This includes several amino-heterocycles, such as the diaminoquinazolines 1, 2, and 3, aminothiazole 4, and the irreversible inhibitor chloroacetamide 5 (FIG. 1). See Chou et al., "Reversible inhibitor of p97, DBeQ, impairs both ubiquitin-dependent and autophagic protein clearance pathways," *Proc. Natl. Acad. Sci. USA*, 705:4834-4839 (2011); Fang et al., "Evaluating p97 inhibitor analogues for their domain selectivity and potency against the p97-p47 complex," *ChemMedChem*, 10, 52-56 (2015); Zhou et al., "Preparation of fused pyrimidines as inhibitors of p97 complex," WO 2014/015291; *Chem. Abstr.*, 760:248915 (2014); Bursavich et al., "2-Anilino-4-aryl-1,3-thiazole inhibitors of valosin-containing protein (VCP or p97)," *Bioorg. Med. Chem. Lett.*, 20:1677-1679 (2010); Magnaghi et al., "Covalent and allosteric inhibitors of the ATPase VCP/p97 induce cancer cell death," *Nat. Chem. Biol.*, 9:548-556 (2013). 1,2,4-Triazole 6, sulfonate 7, and imidazolinone 8 were identified by high throughput screening campaigns, whereas the discovery of the anticancer agent 9 (sorafenib) and the natural products 10 (withaferin A) and 11 (rheoemodin) as p97 inhibitors was based on specific mechanism of action and targeted lead identification studies. See Polucci et al., "Alkylsulfanyl-1,2,4-triazoles, a new class of allosteric valosine containing protein inhibitors. Synthesis and structure-activity relationships," *J. Med. Chem.*, 56: 437-450 (2013); Kakizuka et al., "Preparation of 2-(arylazo or heteroarylazo)-4-aminonaphthalene-1-sulfonic acid derivatives as regulators of vasolin-containing protein (VCP)," WO 2012/014994; Wang et al., "Inhibition of p97-dependent protein degradation by eeyarestatin I," *J. Biol. Chem.*, 283: 7445-7454 (2008); Yi et al., "Sorafenib-mediated targeting of the AAA+ ATPase p97/VCP leads to disruption of the secretory pathway, endoplasmic reticulum stress, and hepatocellular cancer cell death," *Mol. Cancer Ther.*, 77:2610-2620 (2012); Tao et al., "Withaferin A analogs that target the AAA+ chaperone p97," *ACS Chem. Biol.*, 76(8): 1916-1924 (2015); Kang et al., "Functional chromatography reveals three natural products that target the same protein with distinct mechanisms of action," *ChemBioChem*, 75, 2125-2131 (2014).

There remains a need in the art for inhibitors of p97, useful in treating cancer and neurodegenerative disorders caused by proteostatic malfunction. The present invention satisfies these needs.

SUMMARY OF THE DISCLOSED SUBJECT MATTER

The present invention is directed to methods of inhibiting p97 and compounds and compositions useful in such methods. Diseases and conditions the can be treated with the compounds and compositions of the invention include, but are not limited to, cancer and neurodegenerative disorders susceptible to treatment by inhibition of p97. Exemplary neurodegenerative disorders include, but are not limited to, inclusion body myopathy (IBM), Paget's disease of the bone (PDB), frontotemporal dementia (FTD) and amyotrophic lateral sclerosis (ALS).

Subjects having p97 mutations may also be treated with the compounds and compositions according to the invention. Such p97 mutations may manifest symptoms including but not limited to Parkinsonism, ataxia, cataracts, dilated cardiomyopathy, hepatic fibrosis, and hearing loss. Treatment with a compound or composition according to the invention may ameliorate such symptoms.

In one aspect, provided is a compound having the structure of formula (I):

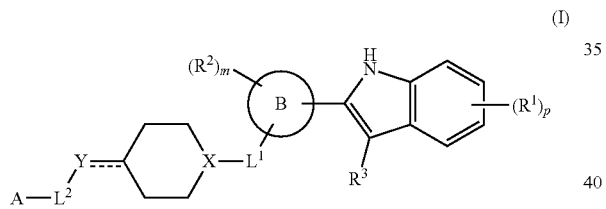

or a pharmaceutically acceptable salt thereof, wherein:
$R^1$ is H, D, halo, cyano, hydroxyl, nitro, —C(O)NR$^5$R$^6$, —C(O)OR$^5$, —N=N$^+$=N$^-$, an optionally substituted $C_1$-$C_3$ alkyl, an optionally substituted $C_1$-$C_3$ alkoxy, —S(O)$_2$NR$^5$R$^6$, an optionally substituted 6-10 membered aryl, an optionally substituted 5-10 membered heteroaryl, —S(O)$_2$R$^5$, —OCZ$_3$, —OCHZ$_2$, —OCH$_2$Z, —SZ$_3$, —SCZ$_3$, or S(Z)$_5$;
each of R$^5$ or R$^6$ is independently H, D, an optionally substituted $C_1$-$C_5$ alkyl, an optionally substituted $C_1$-$C_3$ alkoxy, or R$^5$ and R$^6$, together with the intervening atoms to which they are attached, can form a 5-6 membered ring;
Z is a halo;
ring B is a 6-10 membered aryl, a 5-10 membered heteroaryl, or a 5-10 membered heterocyclyl;
$R^2$ is H, D, halo, cyano, or an optionally substituted $C_1$-$C_3$ alkyl;
m is 0, 1, 2, 3, or 4;
$R^3$ is H, D, or an optionally substituted $C_1$-$C_3$ alkyl; or R$^2$ and R$^3$, together with the intervening atoms to which they are attached, can form a 5-6 membered ring;
$L^1$ is a bond; —C(O)—; —C(O)O—; —OC(O)—; —NR$^5$C(O)NR$^6$—; —NR$^5$C(O)O—; —C(O)NR$^6$—; —S(O)—; or —S(O)$_2$—;

X is CH or N;
Y is a bond, CH, CH$_2$, CH$_3$, N, NH, NH$_2$, O, or S;
$L^2$ is a bond, an optionally substituted $C_1$-$C_5$ alkyl, or an optionally substituted 3-10 membered cycloalkyl;
A is —NR$^{10}$R$^{10}$, —C(O)OR$^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl;
each $R^{10}$ independently is H, an optionally substituted $C_1$-$C_3$ alkyl, an optionally substituted 5-7 membered heteroaryl, or an optionally substituted 6-10 membered aryl;
p is 0, 1, 2, 3, or 4; and ╱╱╱╱  denotes a single or double bond;
wherein the compound is not:

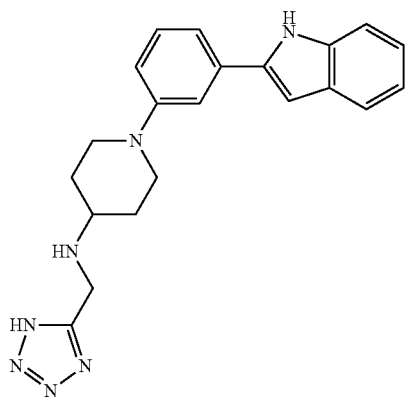

or

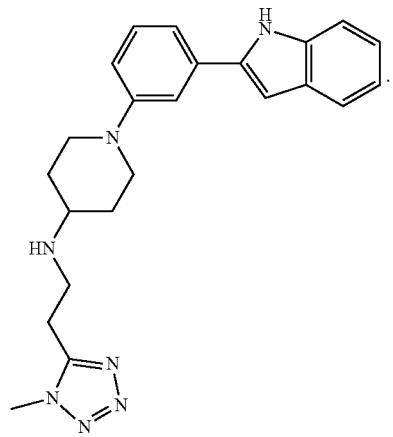

In another aspect, provided is a pharmaceutical composition comprising a compound provided herein and at least one pharmaceutically acceptable excipient or carrier.

In another aspect, provided is a method of inhibiting p97 in a subject in need thereof, comprising administering to the subject a therapeutically effective amount of a compound of formula II or a therapeutically effective amount of a pharmaceutical composition comprising a compound of formula I and at least one pharmaceutically acceptable excipient or carrier:

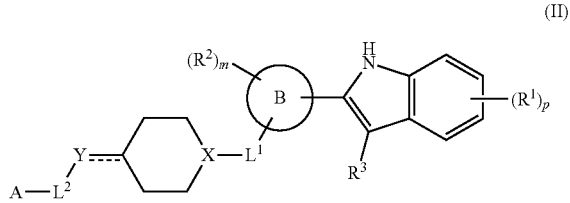

(II)

or a pharmaceutically acceptable salt thereof, wherein:
- $R^1$ is H, D, halo, cyano, hydroxyl, nitro, —C(O)NR$^5$R$^6$, —C(O)OR$^5$, —N=N$^+$=N$^-$ an optionally substituted $C_1$-$C_3$ alkyl, an optionally substituted $C_1$-$C_3$ alkoxy, —S(O)$_2$NR$^5$R$^6$, an optionally substituted 6-10 membered aryl, an optionally substituted 5-10 membered heteroaryl, —S(O)$_2$R$^5$, —OCZ$_3$, —OCHZ$_2$, —OCH$_2$Z, —SZ$_3$, —SCZ$_3$, or S(Z)$_5$;
- each of $R^5$ or $R^6$ is independently H, D, an optionally substituted $C_1$-$C_5$ alkyl, an optionally substituted $C_1$-$C_3$ alkoxy, or $R^5$ and $R^6$, together with the intervening atoms to which they are attached, can form a 5-6 membered ring;
- Z is a halo;
- ring B is a 6-10 membered aryl, a 5-10 membered heteroaryl, or a 5-10 membered heterocyclyl;
- $R^2$ is H, D, halo, cyano, or an optionally substituted $C_1$-$C_3$ alkyl;
- m is 0, 1, 2, 3, or 4;
- $R^3$ is H, D, or an optionally substituted $C_1$-$C_3$ alkyl; or $R^2$ and $R^3$, together with the intervening atoms to which they are attached, can form a 5-6 membered ring;
- $L^1$ is a bond; —C(O)—; —C(O)O—; —OC(O)—; —NR$^5$C(O)NR$^6$—; —NR$^5$C(O)O—; —C(O)NR$^6$—; —S(O)—; or —S(O)$_2$—;
- X is CH or N;
- Y is a bond, CH, CH$_2$, CH$_3$, N, NH, NH$_2$, O, or S;
- $L^2$ is a bond, an optionally substituted $C_1$-$C_5$ alkyl, or an optionally substituted 3-10 membered cycloalkyl;
- A is —NR$^{10}$R$^{10}$, —C(O)OR$^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl;
- each $R^{10}$ independently is H, an optionally substituted $C_1$-$C_3$ alkyl, an optionally substituted 5-7 membered heteroaryl, or an optionally substituted 6-10 membered aryl;
- p is 0, 1, 2, 3, or 4; and ⟋⟋ denotes a single or double bond.

In another aspect, provided is a method of treating cancer or a neurodegenerative disorder susceptible to treatment by p97 inhibition in a subject in need thereof. The method comprises administering to the subject a therapeutically effective amount of a compound of formula I or a therapeutically effective amount of a pharmaceutical composition comprising a compound of formula I and at least one pharmaceutically acceptable excipient or carrier:

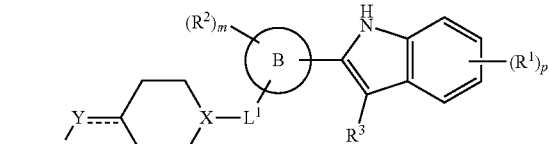

(II)

or a pharmaceutically acceptable salt thereof, wherein:
- $R^1$ is H, D, halo, cyano, hydroxyl, nitro, —C(O)NR$^5$R$^6$, —C(O)OR$^5$, —N=N$^+$=N$^-$ an optionally substituted $C_1$-$C_3$ alkyl, an optionally substituted $C_1$-$C_3$ alkoxy, —S(O)$_2$NR$^5$R$^6$, an optionally substituted 6-10 membered aryl, an optionally substituted 5-10 membered heteroaryl, —S(O)$_2$R$^5$, —OCZ$_3$, —OCHZ$_2$, —OCH$_2$Z, —SZ$_3$, —SCZ$_3$, or S(Z)$_5$;
- each of $R^5$ or $R^6$ is independently H, D, an optionally substituted $C_1$-$C_5$ alkyl, an optionally substituted $C_1$-$C_3$ alkoxy, or $R^5$ and $R^6$, together with the intervening atoms to which they are attached, can form a 5-6 membered ring;
- Z is a halo;
- ring B is a 6-10 membered aryl, a 5-10 membered heteroaryl, or a 5-10 membered heterocyclyl;
- $R^2$ is H, D, halo, cyano, or an optionally substituted $C_1$-$C_3$ alkyl;
- m is 0, 1, 2, 3, or 4;
- $R^3$ is H, D, or an optionally substituted $C_1$-$C_3$ alkyl; or $R^2$ and $R^3$, together with the intervening atoms to which they are attached, can form a 5-6 membered ring
- $L^1$ is a bond; —C(O)—; —C(O)O—; —OC(O)—; —NR$^5$C(O)NR$^6$—; —NR$^5$C(O)O—; —C(O)NR$^6$—; —S(O)—; or —S(O)$_2$—;
- X is CH or N;
- Y is a bond, CH, CH$_2$, CH$_3$, N, NH, NH$_2$, O, or S;
- $L^2$ is a bond, an optionally substituted $C_1$-$C_5$ alkyl, or an optionally substituted 3-10 membered cycloalkyl;
- A is —NR$^{10}$R$^{10}$, —C(O)OR$^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl;
- each $R^{10}$ independently is H, an optionally substituted $C_1$-$C_3$ alkyl, an optionally substituted 5-7 membered heteroaryl, or an optionally substituted 6-10 membered aryl;
- p is 0, 1, 2, 3, or 4; and ⟋⟋ denotes a single or double bond.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

DETAILED DESCRIPTION

I. Compounds of the Disclosure

Figure 1:
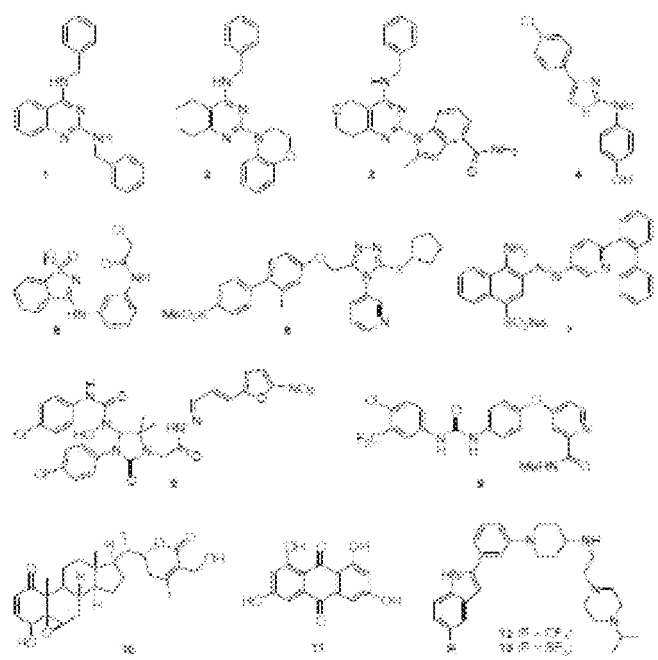
FIG. 1 shows the structures of p97 inhibitors.
Figure 2:
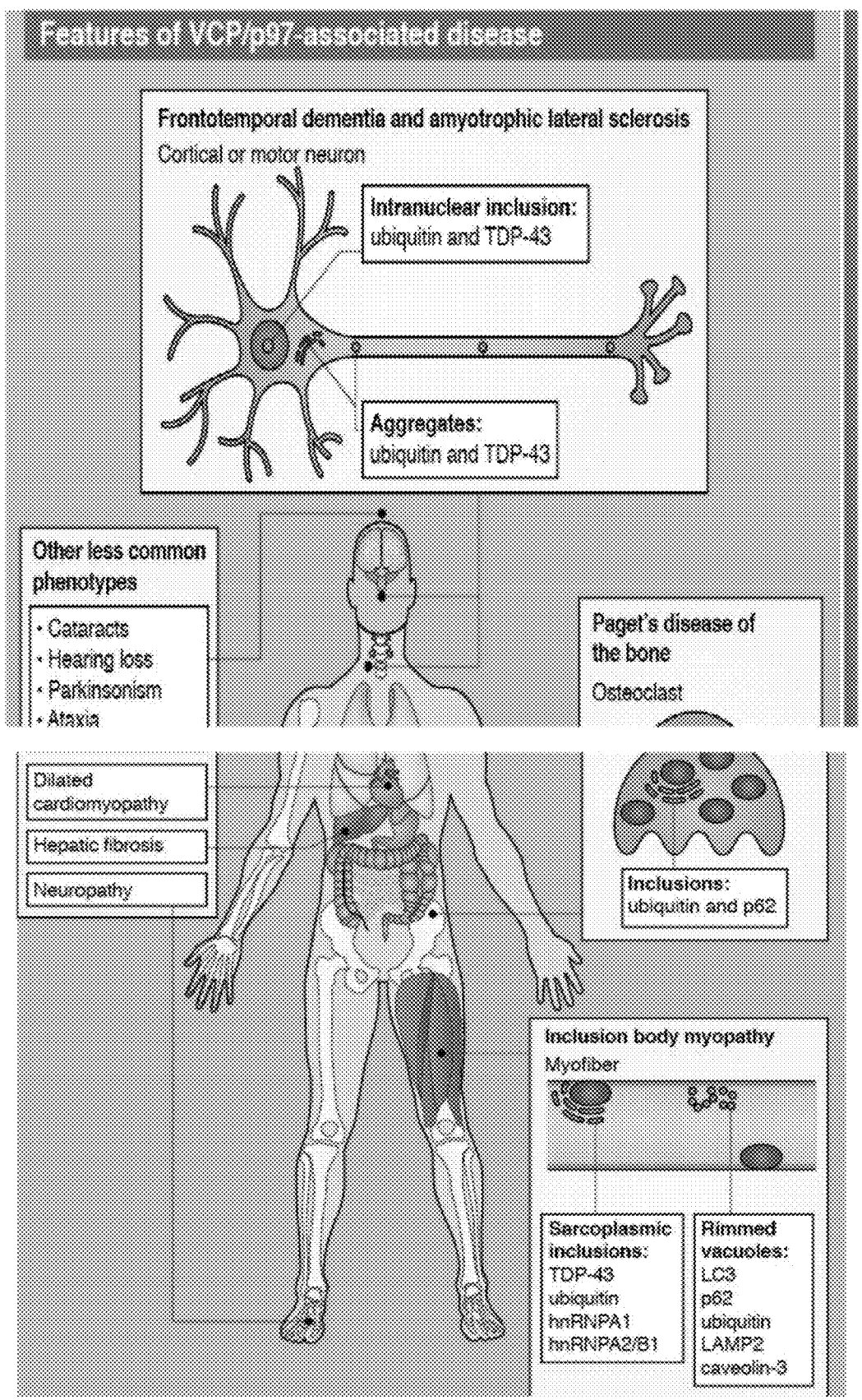
FIG. 2 shows the features of p97-associated disease.

Compounds of the present disclosure include novel compounds with the following core structure:

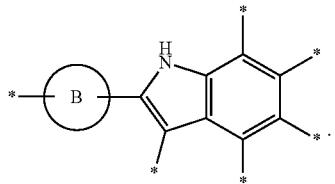

The core structure is substituted at one or more positions marked as *.

In some embodiments, the compounds of the present disclosure are represented by the following structure:

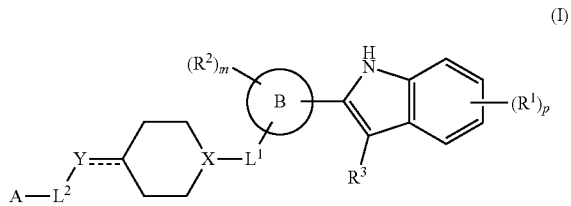

or a pharmaceutically acceptable salt thereof.

In some embodiments, $R^1$ is a H, D, halo, cyano, hydroxyl, nitro, or —N=N$^+$=N$^-$. In some embodiments, $R^1$ is an optionally substituted alkyl, an optionally substituted alkoxy, an optionally substituted aryl, or an optionally substituted heteroaryl. In some embodiments, $R^1$ is an optionally substituted $C_1$-$C_3$ alkyl, an optionally substituted $C_1$-$C_3$ alkoxy, an optionally substituted 6-10 membered aryl, or an optionally substituted 5-10 membered heteroaryl.

In some embodiments, $R^1$ is —C(O)NR$^5$R$^6$, —C(O)OR$^5$, —S(O)$_2$NR$^5$R$^6$, or —S(O)$_2$R$^5$, wherein each of R$^5$ or R$^6$ is independently H, D, an optionally substituted alkyl, or an optionally substituted alkoxy. In some embodiments, each of R$^5$ or R$^6$ is independently an optionally substituted $C_1$-$C_5$ alkyl or an optionally substituted $C_1$-$C_3$ alkoxy. In some embodiments, each of R$^5$ and R$^6$, together with the intervening atoms to which they are attached, can form a 5-6 membered ring.

In some embodiments, $R^1$ is —OCZ$_3$, —OCHZ$_2$, —OCH$_2$Z, —SZ$_3$, —SCZ$_3$, or S(Z)$_5$, wherein Z is a halo. In some embodiments, Z is preferably F.

In some embodiments, ring B is a 6-10 membered aryl, a 5-10 membered heteroaryl, or a 5-10 membered heterocyclyl. In some embodiments, ring B is a phenyl. In some embodiments, ring B is a 5-6 membered heteroaryl. In some embodiments, ring B is a pyridinyl.

In some embodiments, $R^1$ is preferably halo, cyano, N(O)$_2$, hydroxyl, or —C(O)NR$^5$R$^6$, wherein each of R$^5$ or R$^6$ is independently H, D, an optionally substituted alkyl, or an optionally substituted alkoxy. In some embodiments, each of R$^5$ or R$^6$ is independently an optionally substituted $C_1$-$C_5$ alkyl or an optionally substituted $C_1$-$C_3$ alkoxy. In some embodiments, each of R$^5$ and R$^6$, together with the intervening atoms to which they are attached, can form a 5-6 membered ring.

In some embodiments, $R^2$ is H, D, halo, cyano, or an optionally substituted alkyl. In some embodiments, $R^2$ is an optionally substituted $C_1$-$C_3$ alkyl.

In some embodiments, $R^3$ is H, D, or an optionally substituted alkyl. In some embodiments, $R^3$ is H, D, or an optionally substituted $C_1$-$C_3$ alkyl.

In some embodiments, $R^2$ and $R^3$, together with the intervening atoms to which they are attached, can form a 5-6 membered ring.

In some embodiments, $L^1$ is a bond; —C(O)—; —C(O)O—; —OC(O)—; —NR$^5$C(O)NR$^6$—; —NR$^5$C(O)O—; —C(O)NR$^6$—; —S(O)—; or —S(O)$_2$—; wherein each of R$^5$ or R$^6$ is independently H, D, an optionally substituted alkyl, or an optionally substituted alkoxy. In some embodiments, each of R$^5$ or R$^6$ is independently an optionally substituted $C_1$-$C_5$ alkyl or an optionally substituted $C_1$-$C_3$ alkoxy. In some embodiments, each of R$^5$ and R$^6$, together with the intervening atoms to which they are attached, can form a 5-6 membered ring.

In some embodiments, $L^1$ and

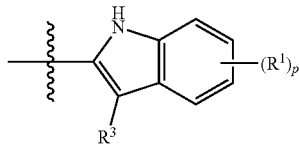

are meta-substituted to one another on ring B. In some embodiments, $R^2$ is para-substituted to $L^1$ on ring B. In some embodiments, $R^2$ is ortho-substituted to

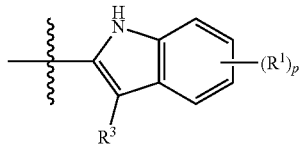

on ring B.

In some embodiments, X is CH or N. In some embodiments, X is preferably N.

In some embodiments, Y is a bond, CH, CH$_2$, CH$_3$, N, NH, NH$_2$, O, or S. In some embodiments, Y is preferably NH.

In some embodiments, $L^2$ is a bond, an optionally substituted alkyl, or an optionally substituted cycloalkyl. In some embodiments, $L^2$ is an optionally substituted $C_1$-$C_5$ alkyl or an optionally substituted 3-10 membered cycloalkyl. In some embodiments, $L^2$ is an optionally substituted $C_1$-$C_3$ alkyl. In some embodiments, $L^2$ is an optionally substituted $C_2$ alkyl.

In some embodiments, A is —NR$^{10}$R$^{10}$ or —C(O)OR$^{10}$, wherein each R$^{10}$ independently is H, an optionally substituted alkyl, an optionally substituted heteroaryl, or an optionally substituted aryl. In some embodiments, each R$^{10}$ independently is an optionally substituted $C_1$-$C_3$ alkyl, an optionally substituted 5-7 membered heteroaryl, or an optionally substituted 6-10 membered aryl.

In some embodiments, A is an optionally substituted alkyl, an optionally substituted heterocyclyl, an optionally substituted heteroaryl, an optionally substituted aryl, or an optionally substituted cycloalkyl. In some embodiments, A is an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl.

In some embodiments, A is a 4-10 membered heterocyclyl. In some embodiments, A is a 4-10 membered heterocyclyl, wherein one of the ring heteroatoms of A is N.

In some embodiments, A has the structure:

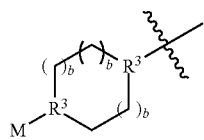

wherein each b is independently 0 or 1. In some embodiments, one b is 1 and the remaining two b's are 0. In some embodiments, two b's are 1 and the remaining b is 0. In some embodiments, all three b's are 1.

In some embodiments, A has the structure:

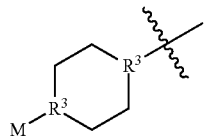

wherein each $R^3$ is independently CH or N and M is an optionally substituted alkyl. In some embodiments, M is an optionally substituted $C_1$-$C_6$ alkyl. In preferred embodiments, M is a $C_1$-$C_3$ alkyl.

In some embodiments, A has the structure:

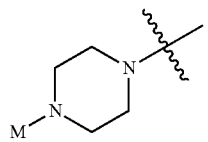

wherein M is an optionally substituted alkyl. In some embodiments, M is an optionally substituted $C_1$-$C_6$ alkyl. In preferred embodiments, M is a $C_1$-$C_3$ alkyl.

In some embodiments, m is 0, 1, 2, 3, or 4. In some embodiments, m is 0. In some embodiments, m is 1. In some embodiments, m is 2. In some embodiments, p is 0, 1, 2, 3, or 4. In some embodiments, p is 0. In some embodiments, p is 1. In some embodiments, p is 2.

 denotes a single or double bond.

In some embodiments, the compounds of the present disclosure are not

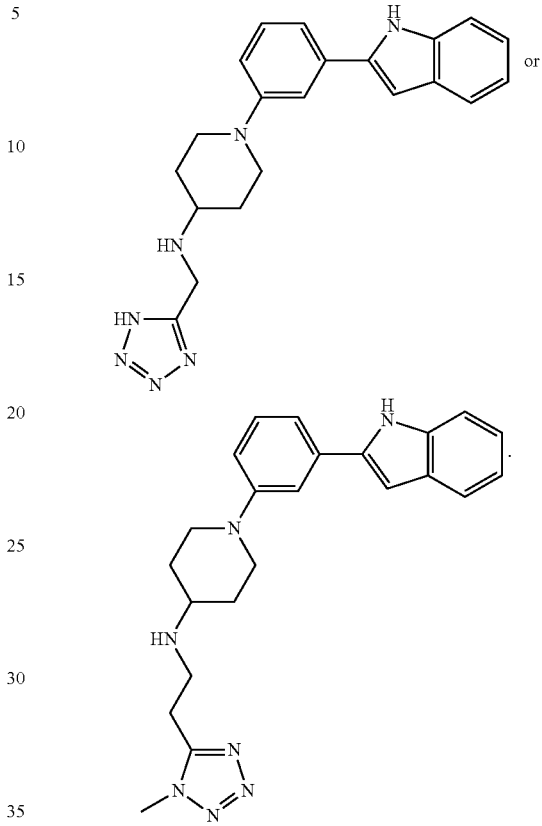

In some embodiments, the compounds of the present disclosure have the structure of formula III

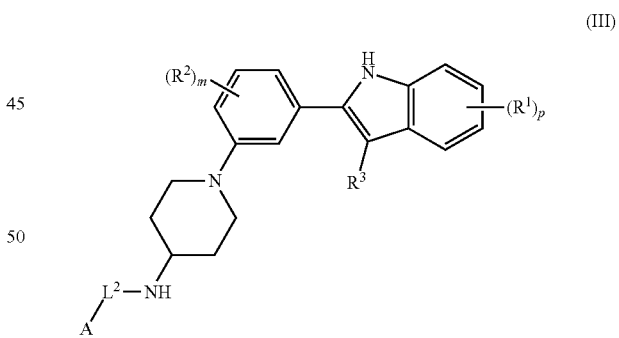

(III)

wherein the remaining variables are defined as above.

In some embodiments, the compounds of the present disclosure are selected from the compounds of Table 1 or a pharmaceutically acceptable salt thereof. It should be noted that the moieties of the compounds of Table 1 fall within the scope of compounds of Formulae (I) and (II). The present disclosure includes embodiments where one or more of the variable moieties of Formulae (I) or (II) are represented by the equivalent moiety of one or more of the compounds of Table 1 without requiring the other specific moieties of the same compound of Table 1.

TABLE 1
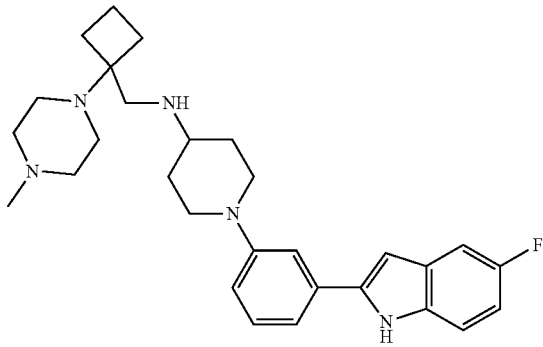 [SMILES: CN1CCN(C2(CNC3CCN(c4cccc(-c5cc6cc(F)ccc6[nH]5)c4)CC3)CCC2)CC1]
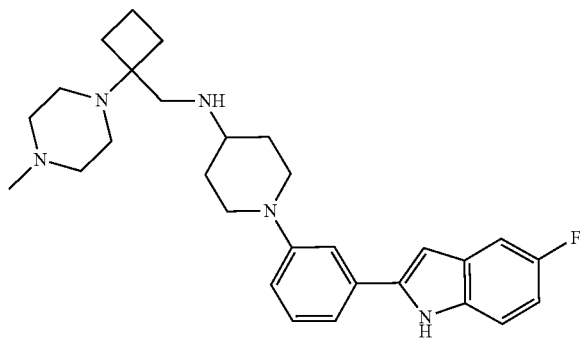 [SMILES: CN1CCN(C2(CNC3CCN(c4cccc(-c5cc6cc(F)ccc6[nH]5)c4)CC3)CCC2)CC1]
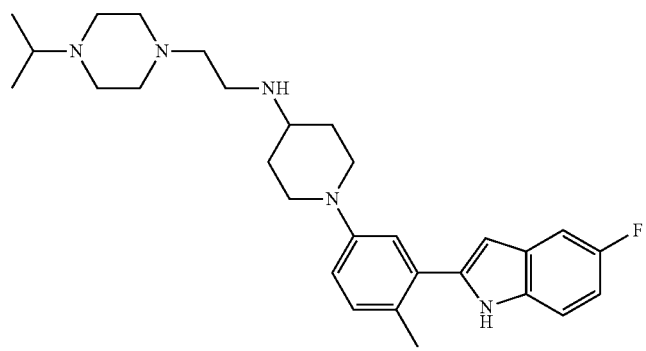 [SMILES: Cc1ccc(N2CCC(NCCN3CCN(C(C)C)CC3)CC2)cc1-c1cc2cc(F)ccc2[nH]1]
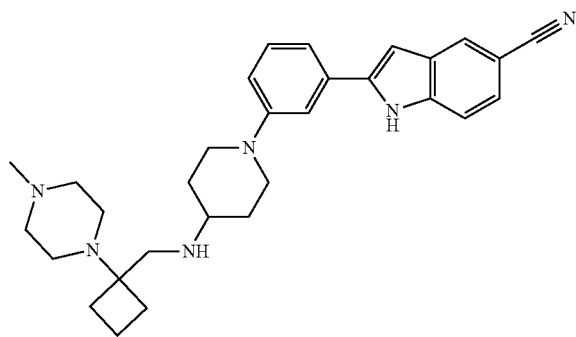 [SMILES: CN1CCN(C2(CNC3CCN(c4cccc(-c5cc6cc(C#N)ccc6[nH]5)c4)CC3)CCC2)CC1]

TABLE 1-continued
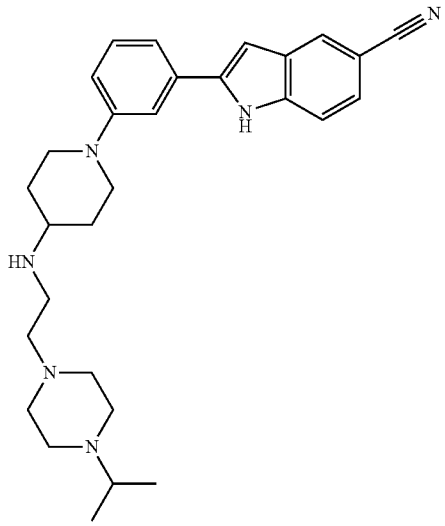 [SMILES: CC(C)N1CCN(CCNC2CCN(c3cccc(-c4cc5cc(C#N)ccc5[nH]4)c3)CC2)CC1]
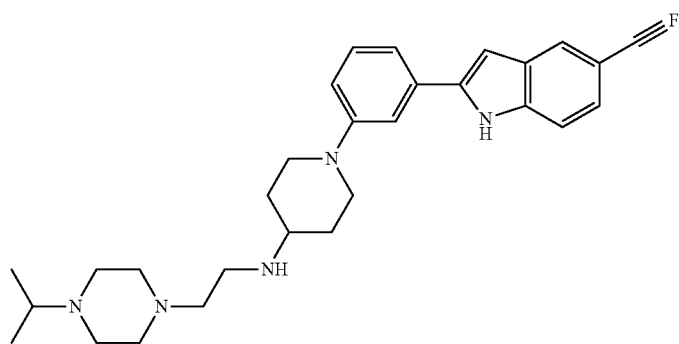
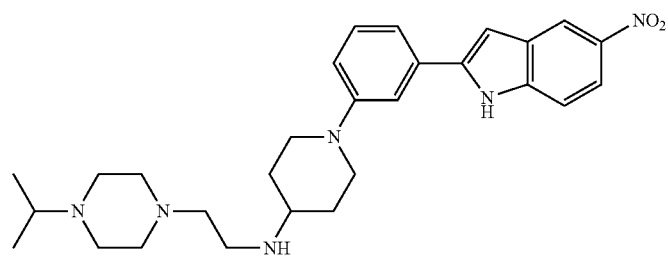 [SMILES: CC(C)N1CCN(CCNC2CCN(c3cccc(-c4cc5cc([N+](=O)[O-])ccc5[nH]4)c3)CC2)CC1]
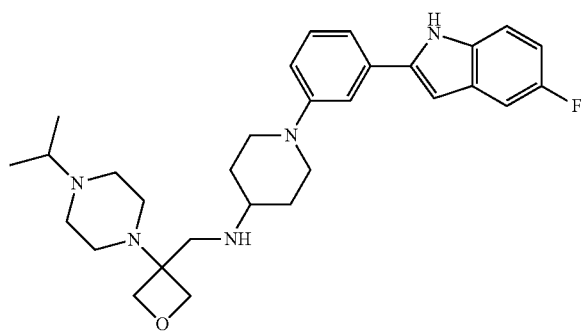 [SMILES: CC(C)N1CCN(C2(CNC3CCN(c4cccc(-c5cc6cc(F)ccc6[nH]5)c4)CC3)COC2)CC1]

TABLE 1-continued
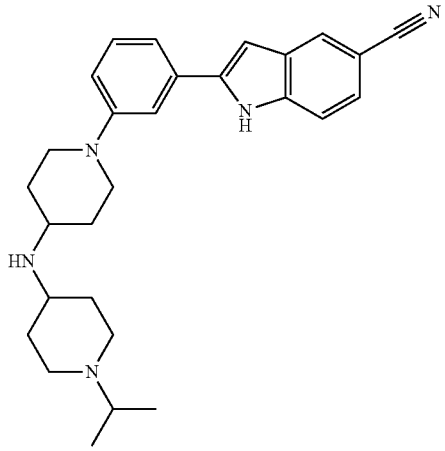 [SMILES: CC(C)N1CCC(NC2CCN(c3cccc(-c4cc5cc(C#N)ccc5[nH]4)c3)CC2)CC1]
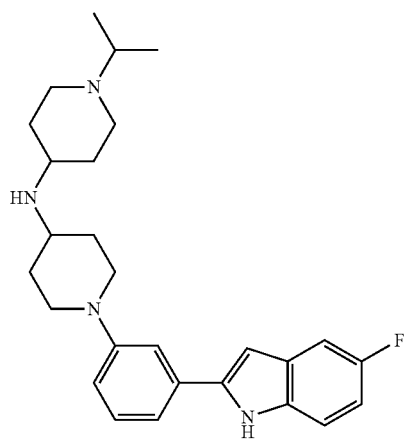 [SMILES: CC(C)N1CCC(NC2CCN(c3cccc(-c4cc5cc(F)ccc5[nH]4)c3)CC2)CC1]
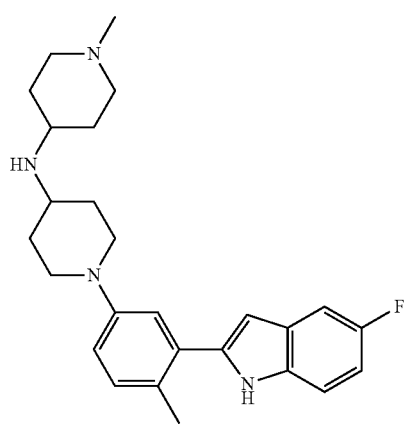 [SMILES: Cc1ccc(N2CCC(NC3CCN(C)CC3)CC2)cc1-c1cc2cc(F)ccc2[nH]1]

TABLE 1-continued
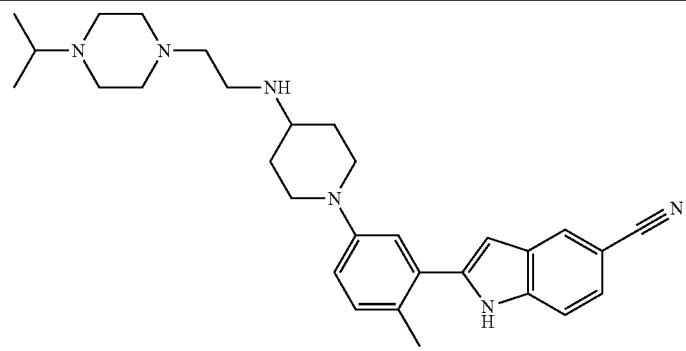
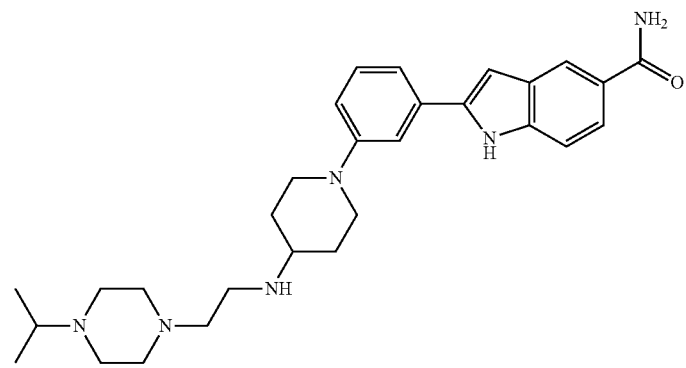 [SMILES: CC(C)N1CCN(CCNC2CCN(c3cccc(-c4cc5cc(C(N)=O)ccc5[nH]4)c3)CC2)CC1]
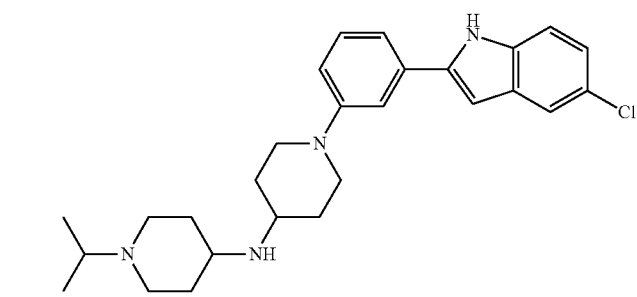 [SMILES: CC(C)N1CCC(NC2CCN(c3cccc(-c4cc5cc(Cl)ccc5[nH]4)c3)CC2)CC1]
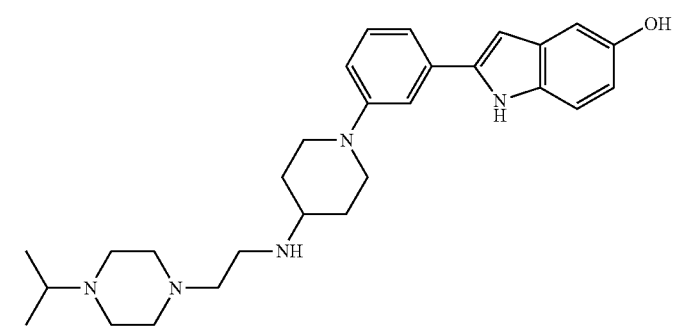 [SMILES: CC(C)N1CCN(CCNC2CCN(c3cccc(-c4cc5cc(O)ccc5[nH]4)c3)CC2)CC1]
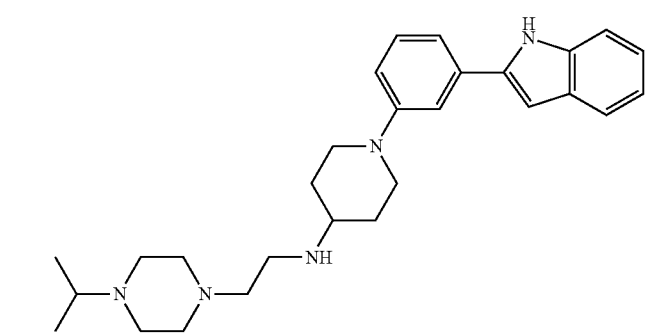 [SMILES: CC(C)N1CCN(CCNC2CCN(c3cccc(-c4cc5ccccc5[nH]4)c3)CC2)CC1]

TABLE 1-continued
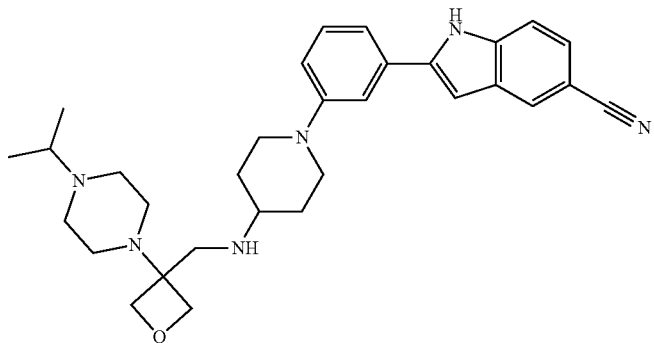 [SMILES: CC(C)N1CCN(C2(CNC3CCN(c4cccc(-c5cc6cc(C#N)ccc6[nH]5)c4)CC3)COC2)CC1]
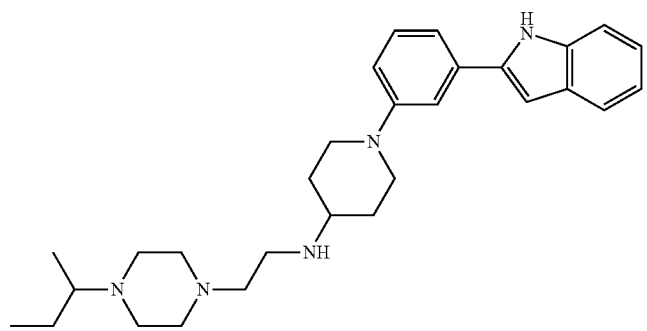 [SMILES: CCC(C)N1CCN(CCNC2CCN(c3cccc(-c4cc5ccccc5[nH]4)c3)CC2)CC1]
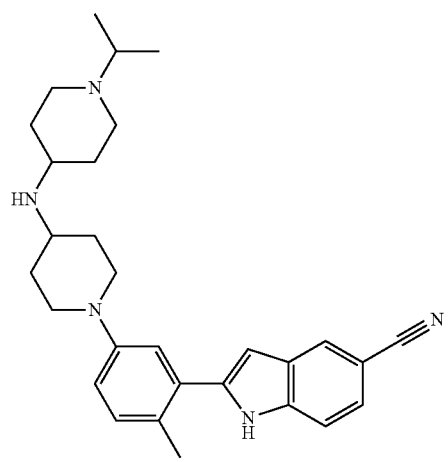 [SMILES: Cc1ccc(N2CCC(NC3CCN(C(C)C)CC3)CC2)cc1-c1cc2cc(C#N)ccc2[nH]1]
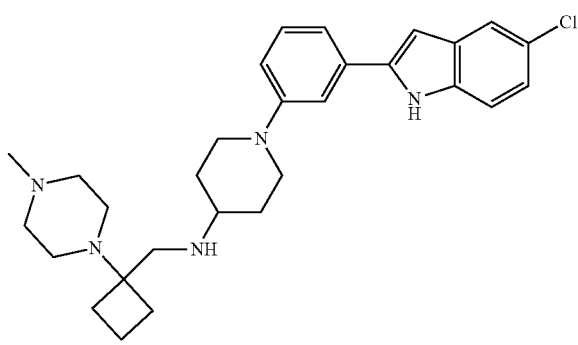 [SMILES: CN1CCN(C2(CNC3CCN(c4cccc(-c5cc6cc(Cl)ccc6[nH]5)c4)CC3)CCC2)CC1]

TABLE 1-continued
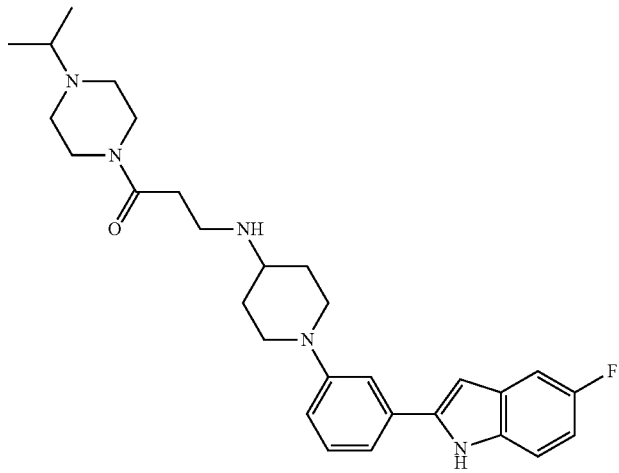 [SMILES: CC(C)N1CCN(C(=O)CCNC2CCN(c3cccc(-c4cc5cc(F)ccc5[nH]4)c3)CC2)CC1]
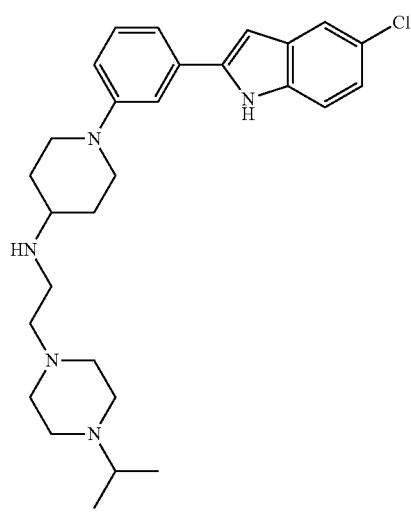
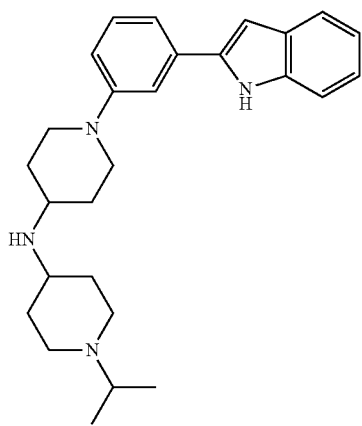 [SMILES: CC(C)N1CCC(NC2CCN(c3cccc(-c4cc5ccccc5[nH]4)c3)CC2)CC1]

TABLE 1-continued
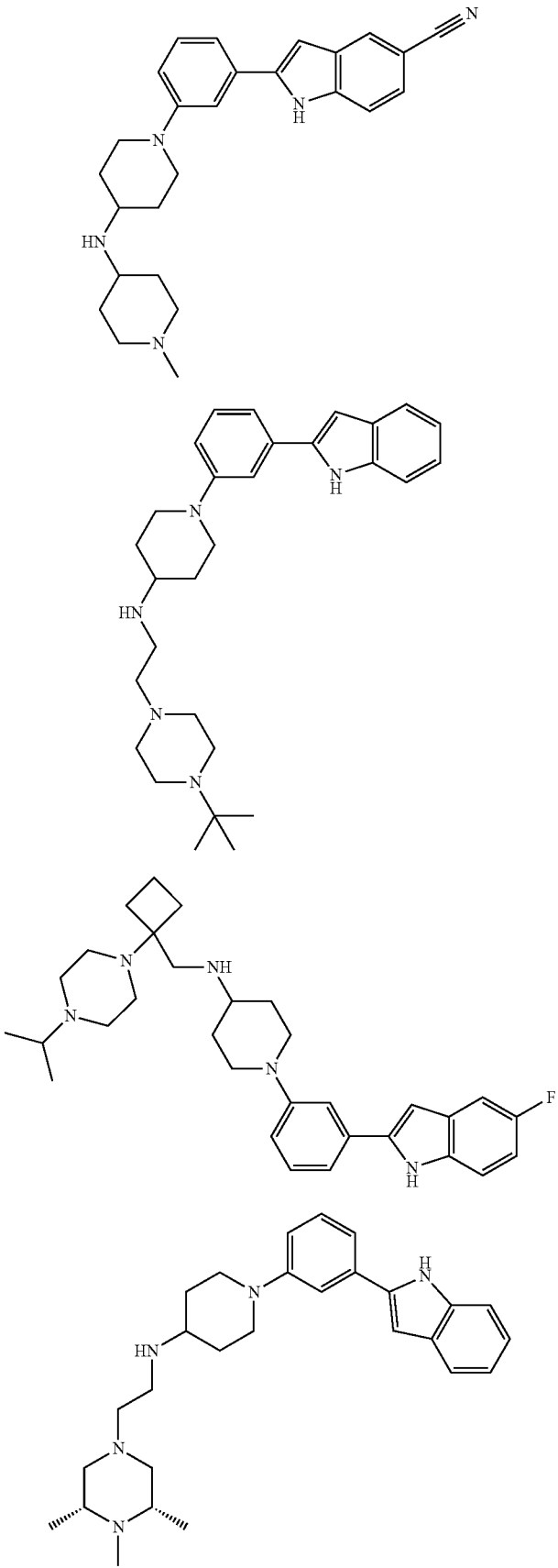

TABLE 1-continued
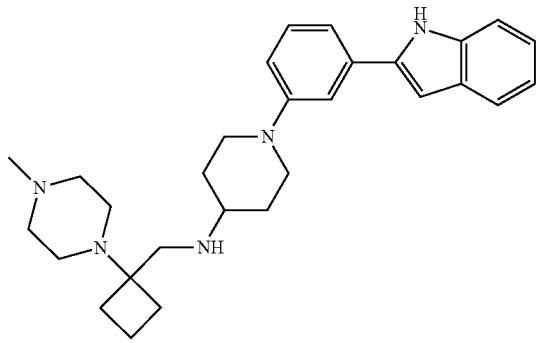 [SMILES: CN1CCN(C2(CNC3CCN(c4cccc(-c5cc6ccccc6[nH]5)c4)CC3)CCC2)CC1]
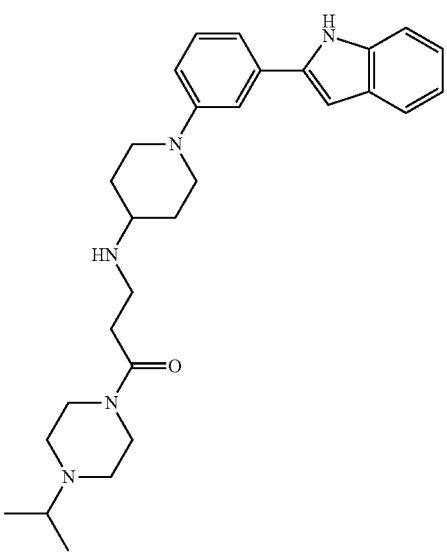 [SMILES: CC(C)N1CCN(C(=O)CCNC2CCN(c3cccc(-c4cc5ccccc5[nH]4)c3)CC2)CC1]
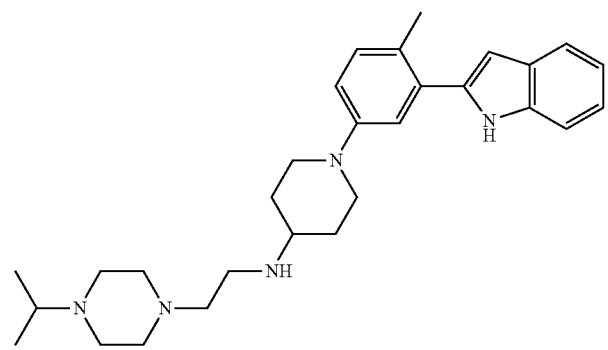 [SMILES: Cc1ccc(N2CCC(NCCN3CCN(C(C)C)CC3)CC2)cc1-c1cc2ccccc2[nH]1]
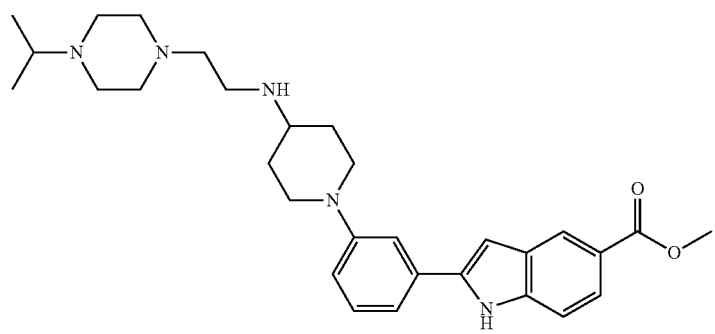 [SMILES: COC(=O)c1ccc2[nH]c(-c3cccc(N4CCC(NCCN5CCN(C(C)C)CC5)CC4)c3)cc2c1]

TABLE 1-continued
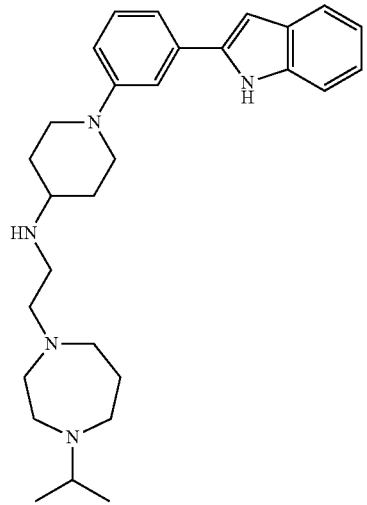 [SMILES: CC(C)N1CCCN(CCNC2CCN(c3cccc(-c4cc5ccccc5[nH]4)c3)CC2)CC1]
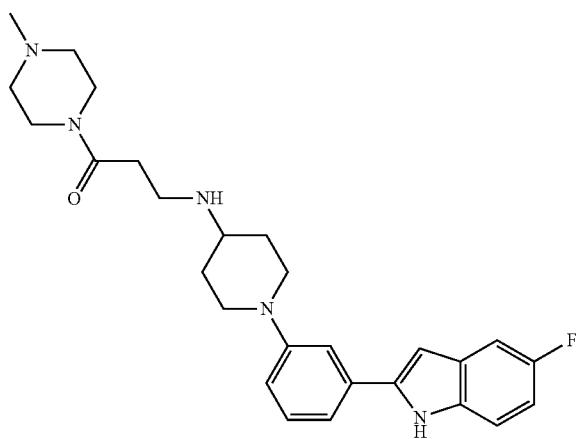 [SMILES: CN1CCN(C(=O)CCNC2CCN(c3cccc(-c4cc5cc(F)ccc5[nH]4)c3)CC2)CC1]
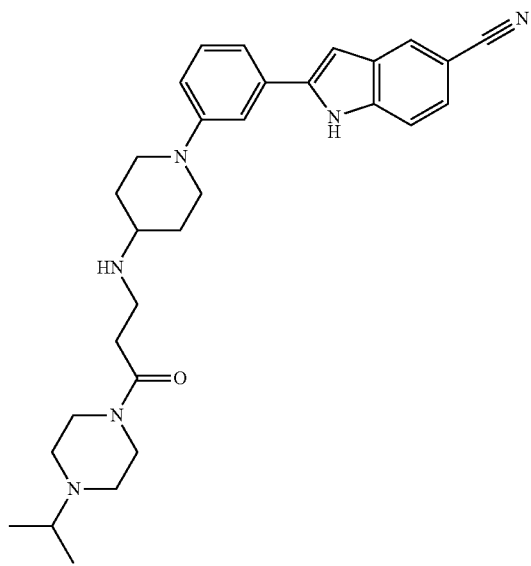 [SMILES: CC(C)N1CCN(C(=O)CCNC2CCN(c3cccc(-c4cc5cc(C#N)ccc5[nH]4)c3)CC2)CC1]

TABLE 1-continued
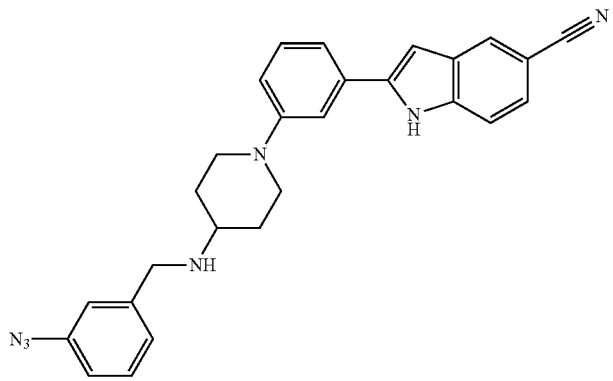 [SMILES: N#Cc1ccc2[nH]c(-c3cccc(N4CCC(NCc5cccc(N=[N+]=[N-])c5)CC4)c3)cc2c1]
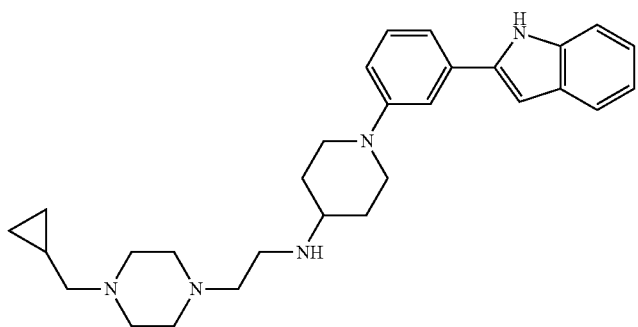 [SMILES: c1cc(-c2cc3ccccc3[nH]2)cc(N2CCC(NCCN3CCN(CC4CC4)CC3)CC2)c1]
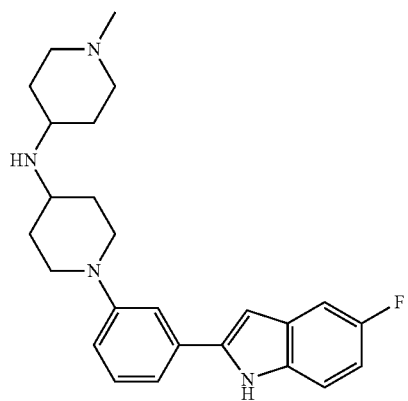 [SMILES: CN1CCC(NC2CCN(c3cccc(-c4cc5cc(F)ccc5[nH]4)c3)CC2)CC1]
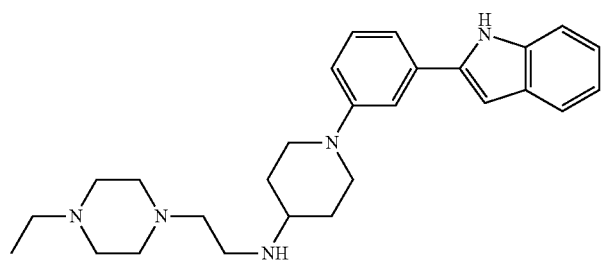 [SMILES: CCN1CCN(CCNC2CCN(c3cccc(-c4cc5ccccc5[nH]4)c3)CC2)CC1]

TABLE 1-continued
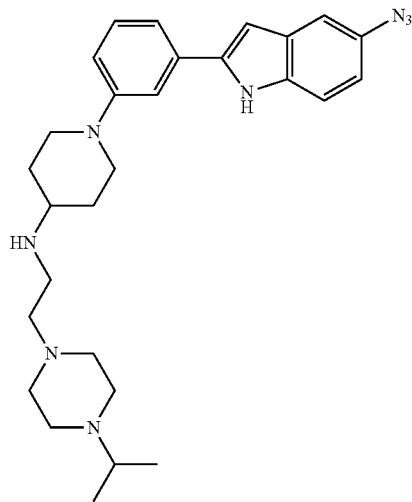 [SMILES: CC(C)N1CCN(CCNC2CCN(c3cccc(-c4cc5cc(N=[N+]=[N-])ccc5[nH]4)c3)CC2)CC1]
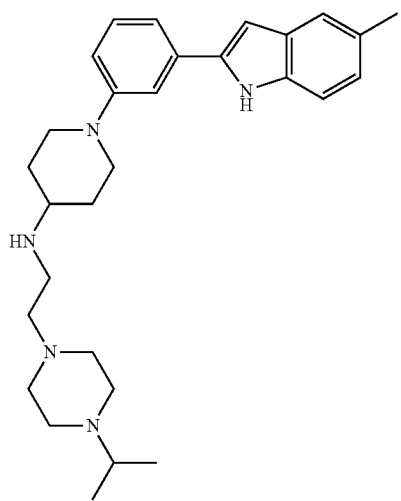 [SMILES: Cc1ccc2[nH]c(-c3cccc(N4CCC(NCCN5CCN(C(C)C)CC5)CC4)c3)cc2c1]
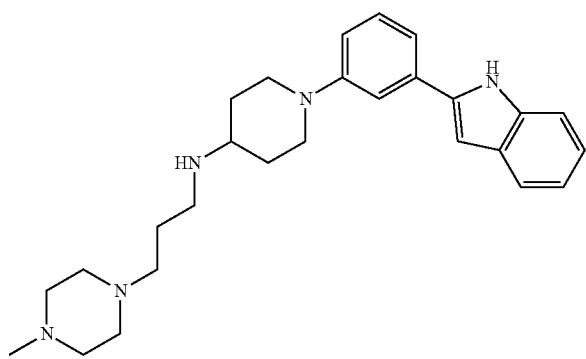 [SMILES: CN1CCN(CCCNC2CCN(c3cccc(-c4cc5ccccc5[nH]4)c3)CC2)CC1]

TABLE 1-continued
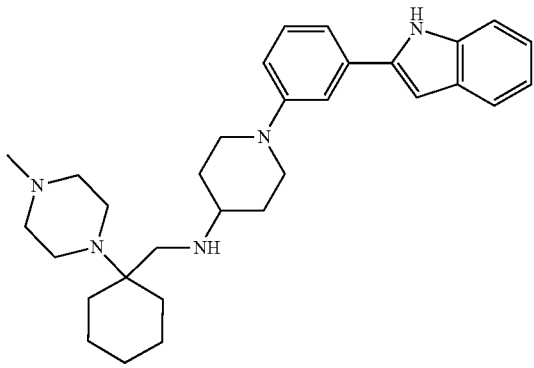 [SMILES: CN1CCN(C2(CNC3CCN(c4cccc(-c5cc6ccccc6[nH]5)c4)CC3)CCCCC2)CC1]
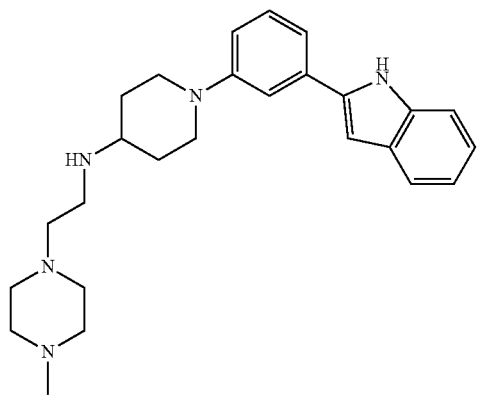 [SMILES: CN1CCN(CCNC2CCN(c3cccc(-c4cc5ccccc5[nH]4)c3)CC2)CC1]
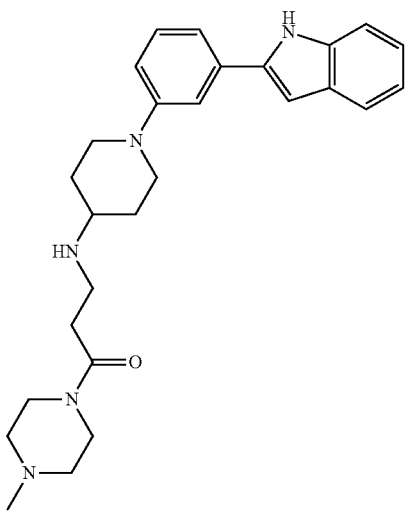 [SMILES: CN1CCN(C(=O)CCNC2CCN(c3cccc(-c4cc5ccccc5[nH]4)c3)CC2)CC1]

TABLE 1-continued
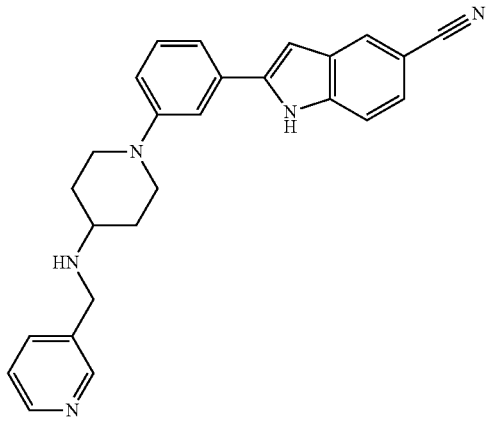 [SMILES: N#Cc1ccc2[nH]c(-c3cccc(N4CCC(NCc5cccnc5)CC4)c3)cc2c1]
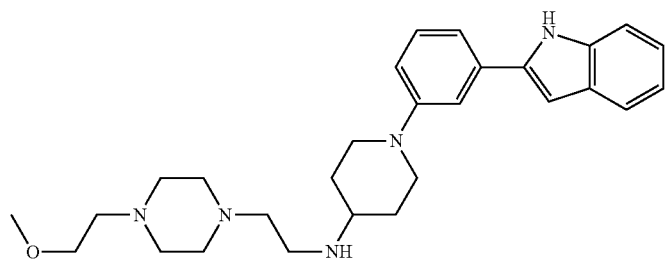 [SMILES: COCCN1CCN(CCNC2CCN(c3cccc(-c4cc5ccccc5[nH]4)c3)CC2)CC1]
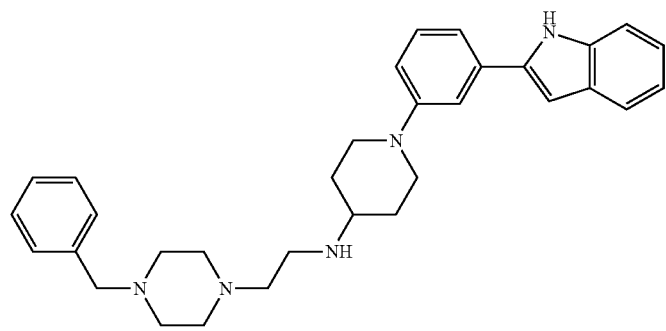 [SMILES: c1ccc(CN2CCN(CCNC3CCN(c4cccc(-c5cc6ccccc6[nH]5)c4)CC3)CC2)cc1]
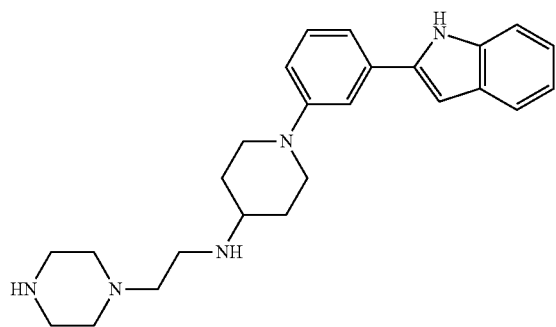 [SMILES: c1cc(-c2cc3ccccc3[nH]2)cc(N2CCC(NCCN3CCNCC3)CC2)c1]

TABLE 1-continued
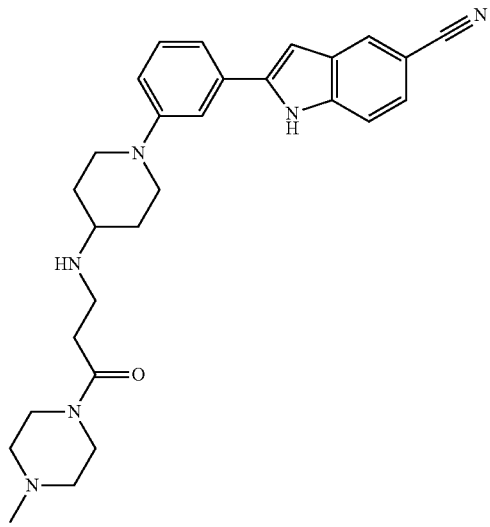 [SMILES: CN1CCN(C(=O)CCNC2CCN(c3cccc(-c4cc5cc(C#N)ccc5[nH]4)c3)CC2)CC1]
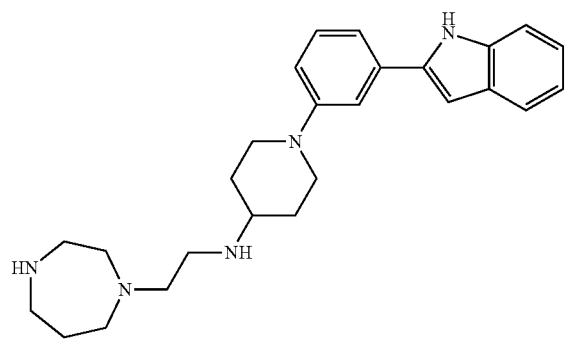 [SMILES: c1cc(-c2cc3ccccc3[nH]2)cc(N2CCC(NCCN3CCCNCC3)CC2)c1]
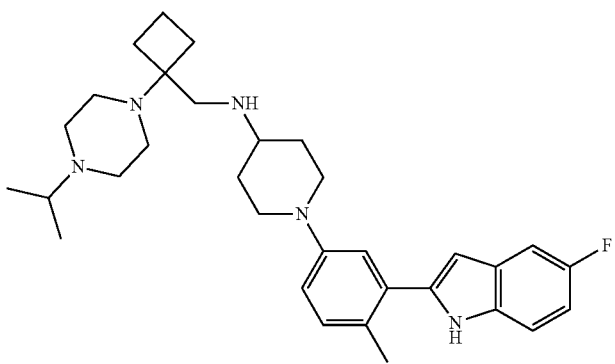 [SMILES: Cc1ccc(N2CCC(NCC3(N4CCN(C(C)C)CC4)CCC3)CC2)cc1-c1cc2cc(F)ccc2[nH]1]

TABLE 1-continued
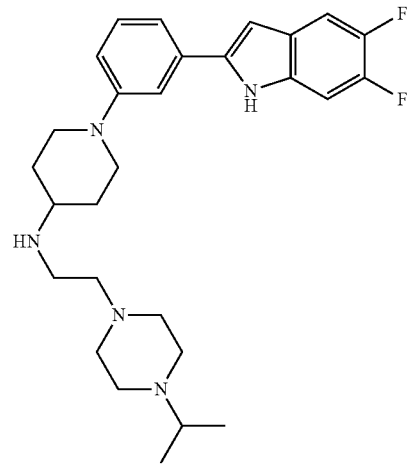 [SMILES: CC(C)N1CCN(CCNC2CCN(c3cccc(-c4cc5cc(F)c(F)cc5[nH]4)c3)CC2)CC1]
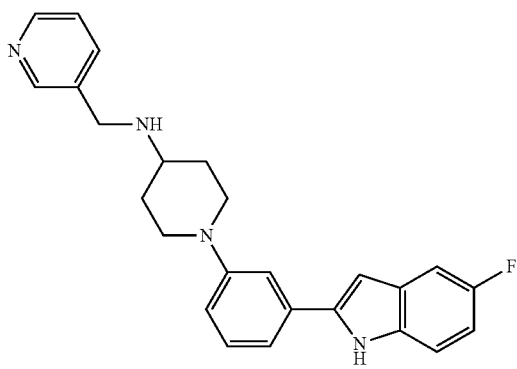 [SMILES: Fc1ccc2[nH]c(-c3cccc(N4CCC(NCc5cccnc5)CC4)c3)cc2c1]
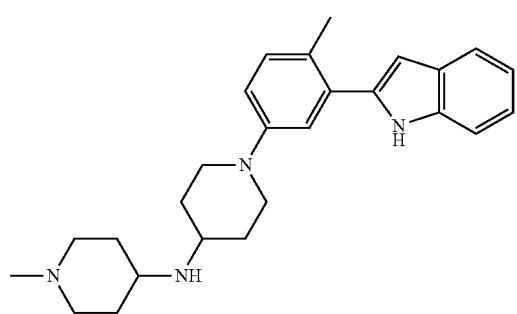 [SMILES: Cc1ccc(N2CCC(NC3CCN(C)CC3)CC2)cc1-c1cc2ccccc2[nH]1]

TABLE 1-continued
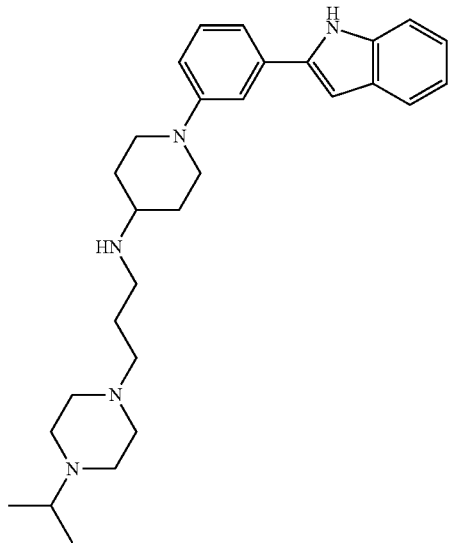 [SMILES: CC(C)N1CCN(CCCNC2CCN(c3cccc(-c4cc5ccccc5[nH]4)c3)CC2)CC1]
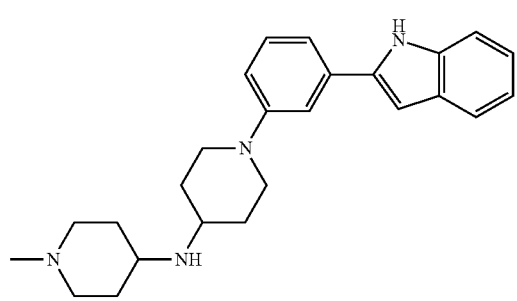 [SMILES: CN1CCC(NC2CCN(c3cccc(-c4cc5ccccc5[nH]4)c3)CC2)CC1]
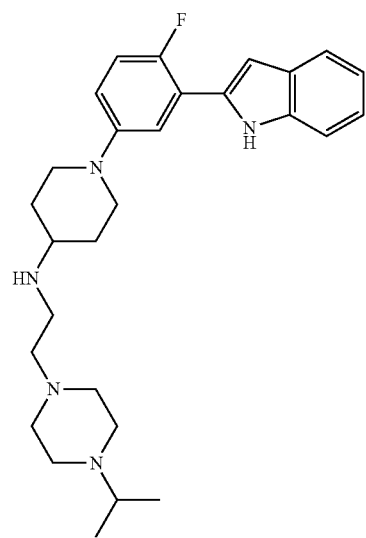

TABLE 1-continued
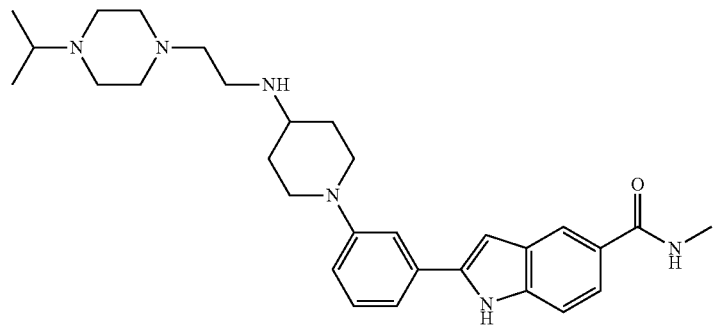
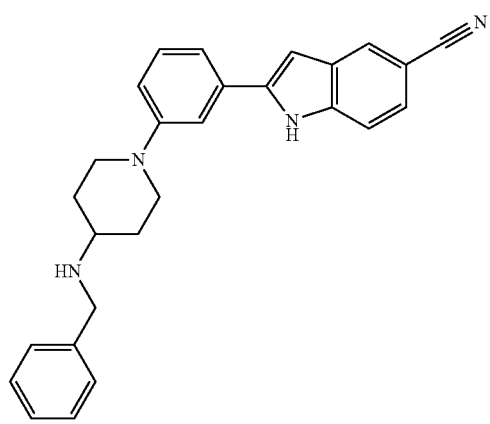 [SMILES: N#Cc1ccc2[nH]c(-c3cccc(N4CCC(NCc5ccccc5)CC4)c3)cc2c1]
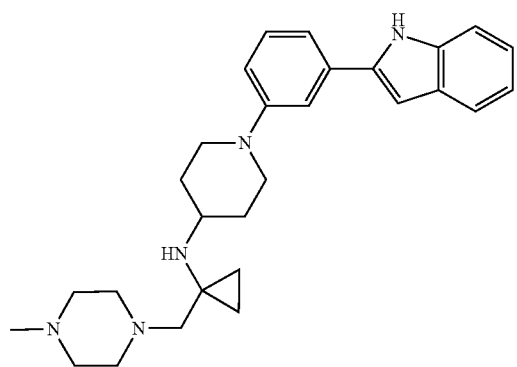 [SMILES: CN1CCN(CC2(NC3CCN(c4cccc(-c5cc6ccccc6[nH]5)c4)CC3)CC2)CC1]
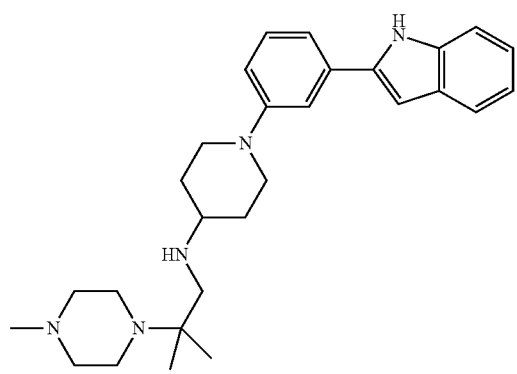 [SMILES: CN1CCN(C(C)(C)CNC2CCN(c3cccc(-c4cc5ccccc5[nH]4)c3)CC2)CC1]

TABLE 1-continued
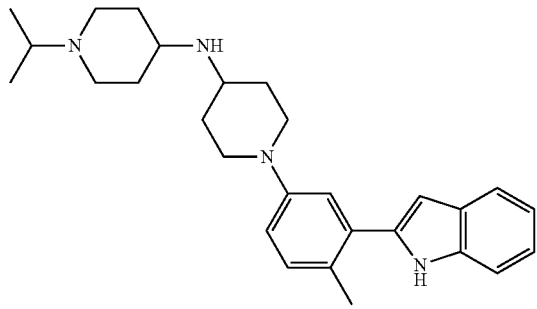 [SMILES: Cc1ccc(N2CCC(NC3CCN(C(C)C)CC3)CC2)cc1-c1cc2ccccc2[nH]1]
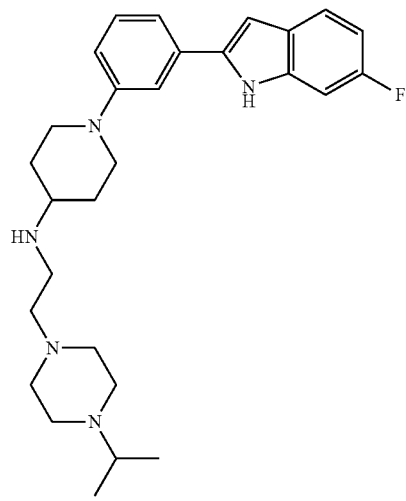 [SMILES: CC(C)N1CCN(CCNC2CCN(c3cccc(-c4cc5ccc(F)cc5[nH]4)c3)CC2)CC1]
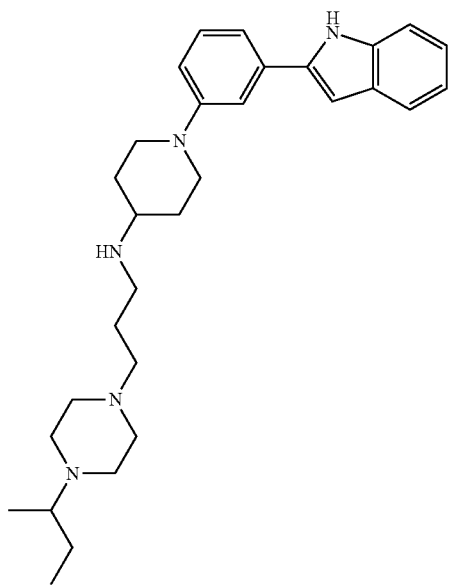 [SMILES: CCC(C)N1CCN(CCCNC2CCN(c3cccc(-c4cc5ccccc5[nH]4)c3)CC2)CC1]

TABLE 1-continued
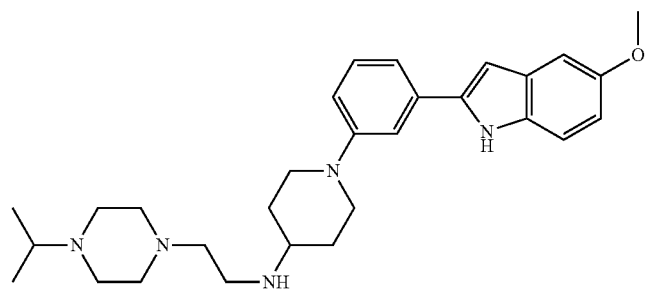 [SMILES: COc1ccc2[nH]c(-c3cccc(N4CCC(NCCN5CCN(C(C)C)CC5)CC4)c3)cc2c1]
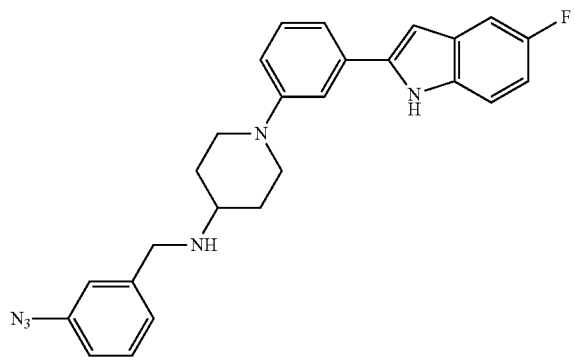 [SMILES: [N-]=[N+]=Nc1cccc(CNC2CCN(c3cccc(-c4cc5cc(F)ccc5[nH]4)c3)CC2)c1]
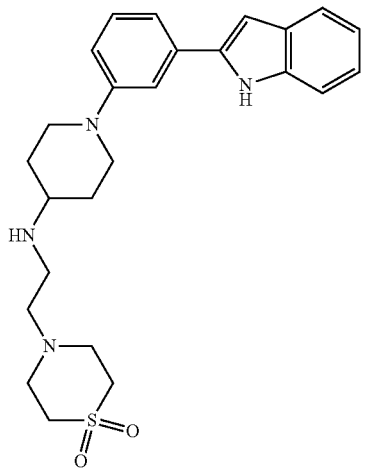
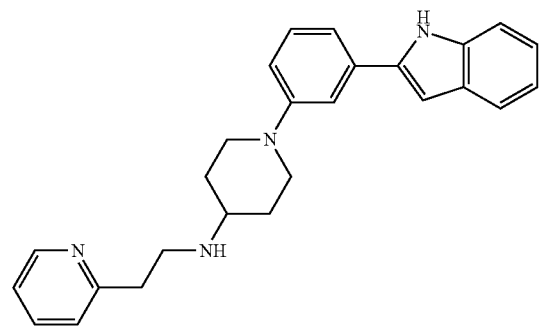 [SMILES: c1ccc(CCNC2CCN(c3cccc(-c4cc5ccccc5[nH]4)c3)CC2)nc1]

TABLE 1-continued
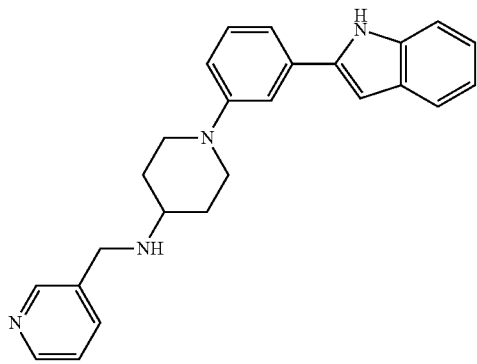 [SMILES: c1cncc(CNC2CCN(c3cccc(-c4cc5ccccc5[nH]4)c3)CC2)c1]
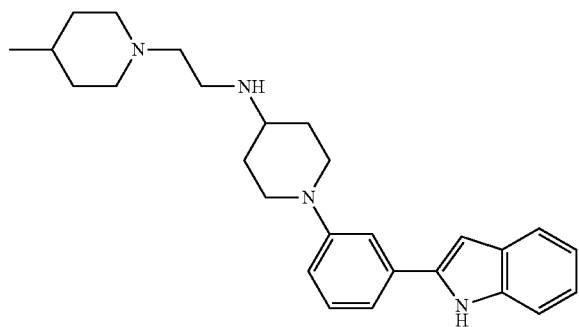 [SMILES: CC1CCN(CCNC2CCN(c3cccc(-c4cc5ccccc5[nH]4)c3)CC2)CC1]
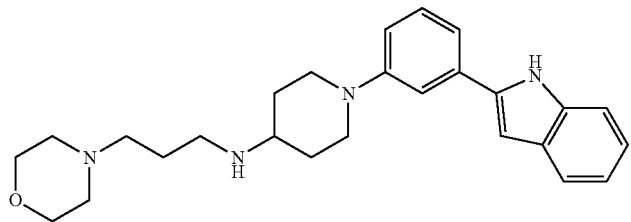 [SMILES: c1cc(-c2cc3ccccc3[nH]2)cc(N2CCC(NCCCN3CCOCC3)CC2)c1]
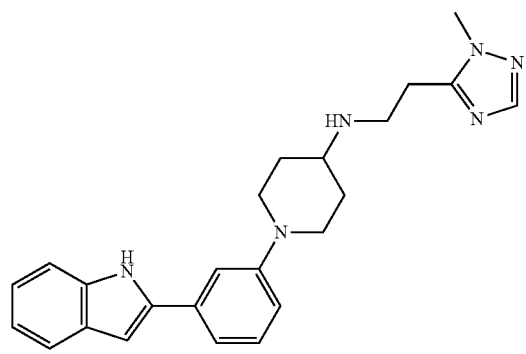 [SMILES: Cn1ncnc1CCNC1CCN(c2cccc(-c3cc4ccccc4[nH]3)c2)CC1]

TABLE 1-continued
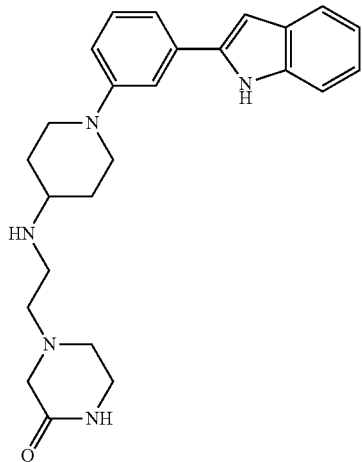 [SMILES: O=C1CN(CCNC2CCN(c3cccc(-c4cc5ccccc5[nH]4)c3)CC2)CCN1]
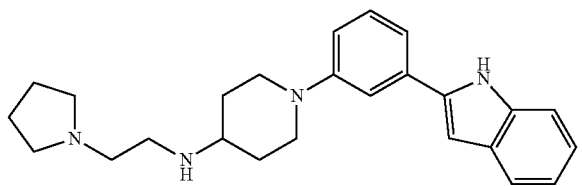 [SMILES: c1cc(-c2cc3ccccc3[nH]2)cc(N2CCC(NCCN3CCCC3)CC2)c1]
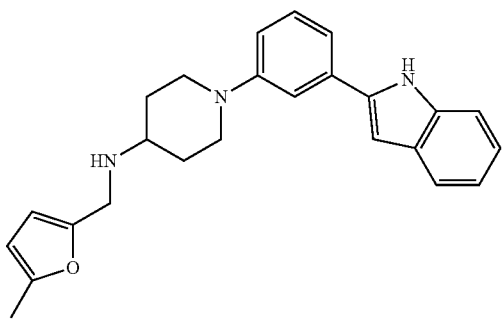 [SMILES: Cc1ccc(CNC2CCN(c3cccc(-c4cc5ccccc5[nH]4)c3)CC2)o1]
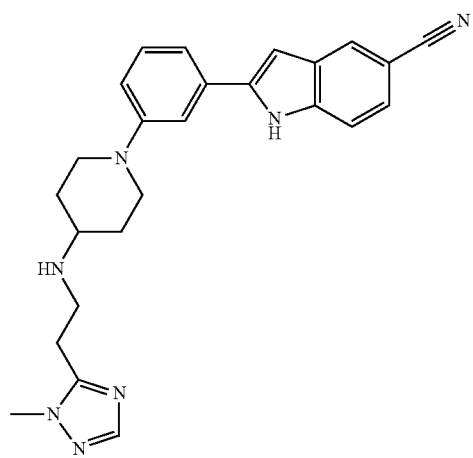 [SMILES: Cn1ncnc1CCNC1CCN(c2cccc(-c3cc4cc(C#N)ccc4[nH]3)c2)CC1]

TABLE 1-continued
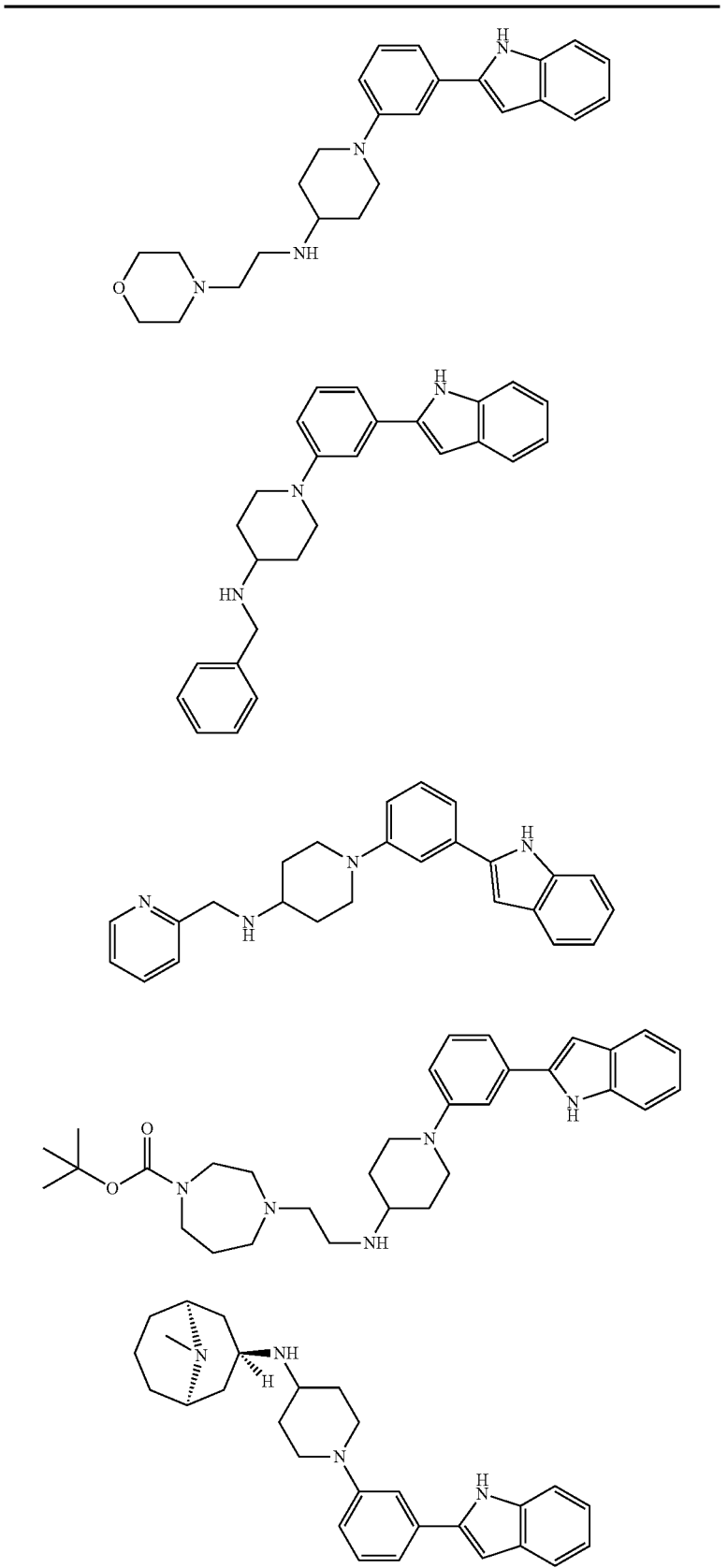

TABLE 1-continued
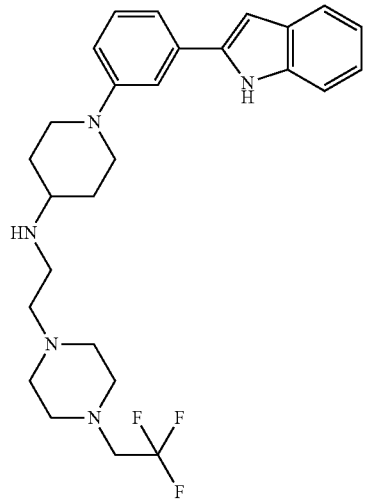 [SMILES: FC(F)(F)CN1CCN(CCNC2CCN(c3cccc(-c4cc5ccccc5[nH]4)c3)CC2)CC1]
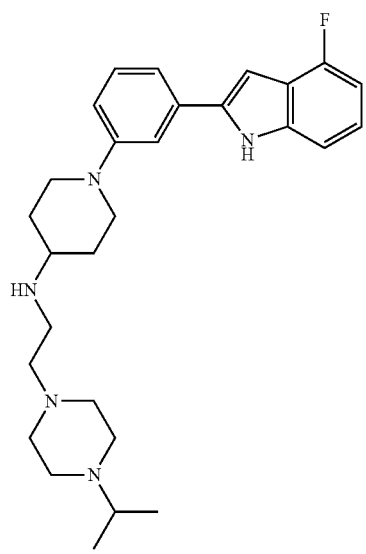 [SMILES: CC(C)N1CCN(CCNC2CCN(c3cccc(-c4cc5c(F)cccc5[nH]4)c3)CC2)CC1]
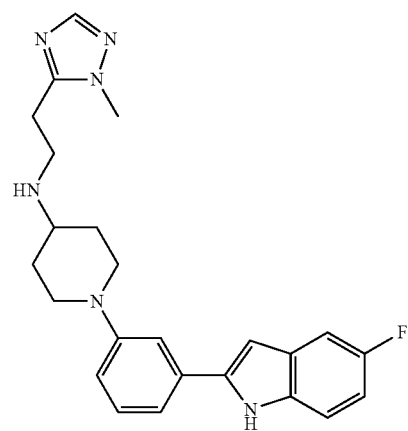 [SMILES: Cn1ncnc1CCNC1CCN(c2cccc(-c3cc4cc(F)ccc4[nH]3)c2)CC1]

TABLE 1-continued
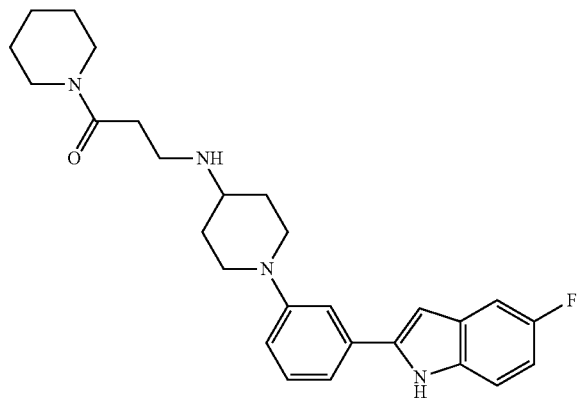 [SMILES: O=C(CCNC1CCN(c2cccc(-c3cc4cc(F)ccc4[nH]3)c2)CC1)N1CCCCC1]
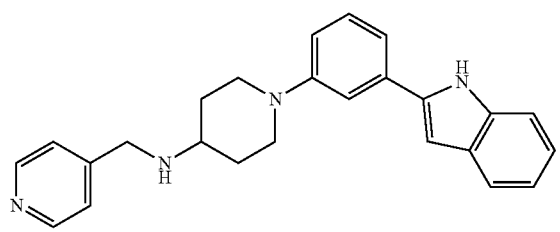 [SMILES: c1cc(-c2cc3ccccc3[nH]2)cc(N2CCC(NCc3ccncc3)CC2)c1]
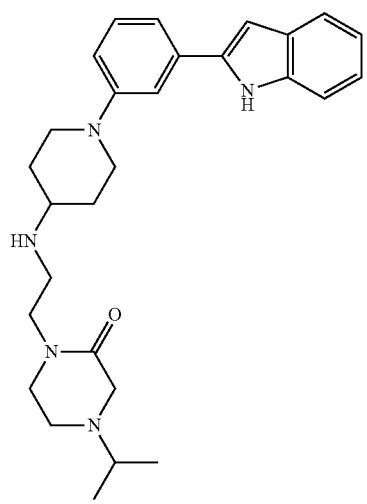 [SMILES: CC(C)N1CCN(CCNC2CCN(c3cccc(-c4cc5ccccc5[nH]4)c3)CC2)C(=O)C1]
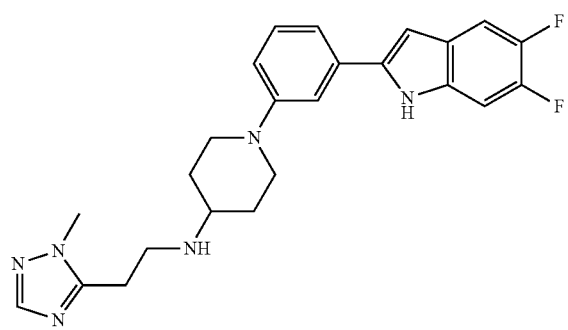 [SMILES: Cn1ncnc1CCNC1CCN(c2cccc(-c3cc4cc(F)c(F)cc4[nH]3)c2)CC1]

TABLE 1-continued
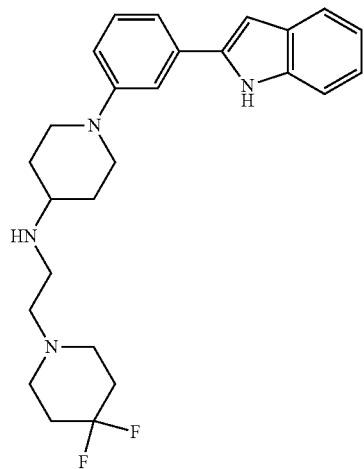 [SMILES: FC1(F)CCN(CCNC2CCN(c3cccc(-c4cc5ccccc5[nH]4)c3)CC2)CC1]
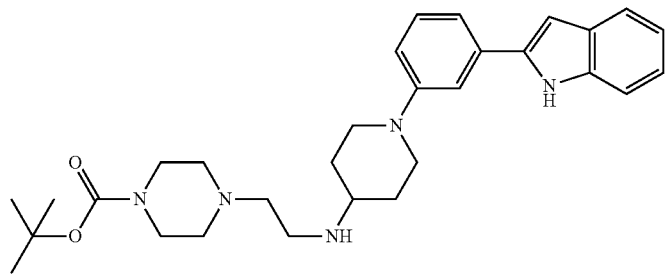 [SMILES: CC(C)(C)OC(=O)N1CCN(CCNC2CCN(c3cccc(-c4cc5ccccc5[nH]4)c3)CC2)CC1]
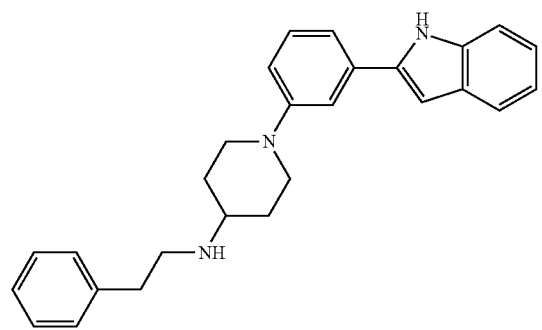 [SMILES: c1ccc(CCNC2CCN(c3cccc(-c4cc5ccccc5[nH]4)c3)CC2)cc1]
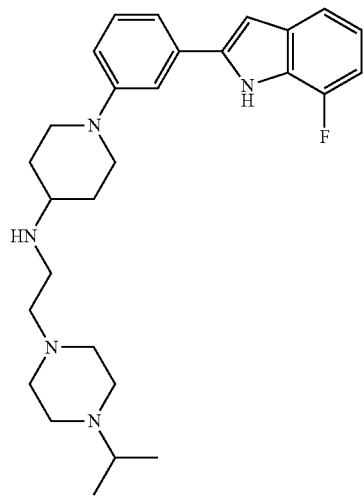 [SMILES: CC(C)N1CCN(CCNC2CCN(c3cccc(-c4cc5cccc(F)c5[nH]4)c3)CC2)CC1]

TABLE 1-continued
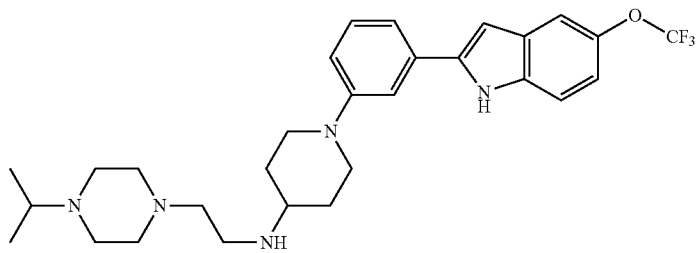 [SMILES: CC(C)N1CCN(CCNC2CCN(c3cccc(-c4cc5cc(OC(F)(F)F)ccc5[nH]4)c3)CC2)CC1]
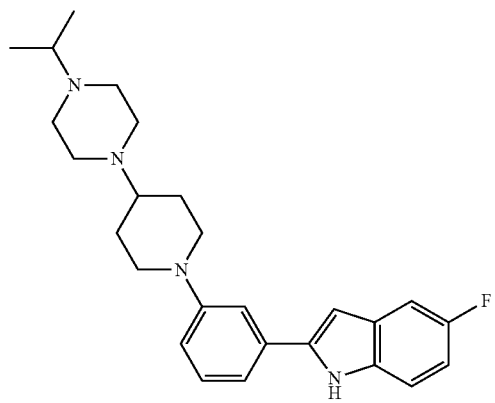 [SMILES: CC(C)N1CCN(C2CCN(c3cccc(-c4cc5cc(F)ccc5[nH]4)c3)CC2)CC1]
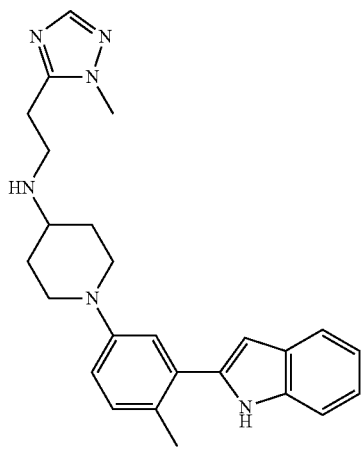 [SMILES: Cc1ccc(N2CCC(NCCc3ncnn3C)CC2)cc1-c1cc2ccccc2[nH]1]
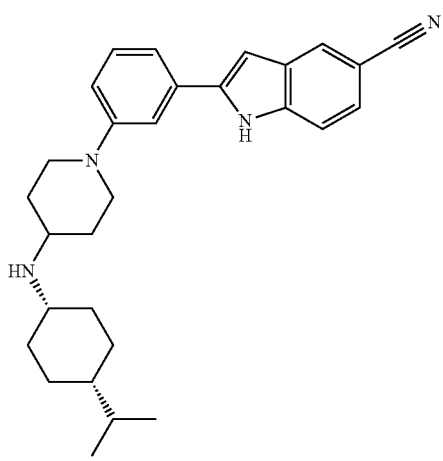 [SMILES: CC(C)[C@H]1CC[C@@H](NC2CCN(c3cccc(-c4cc5cc(C#N)ccc5[nH]4)c3)CC2)CC1]

TABLE 1-continued
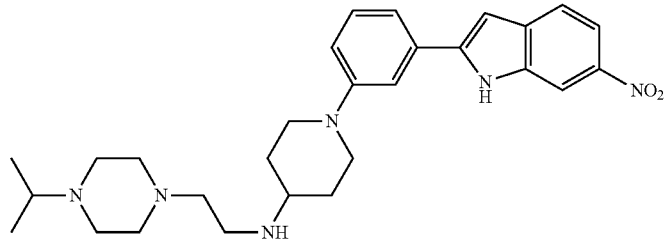 [SMILES: CC(C)N1CCN(CCNC2CCN(c3cccc(-c4cc5ccc([N+](=O)[O-])cc5[nH]4)c3)CC2)CC1]
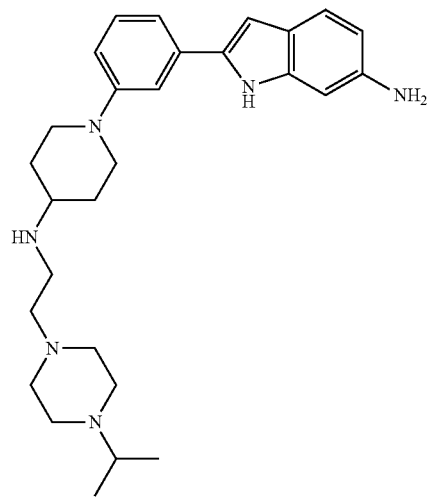 [SMILES: CC(C)N1CCN(CCNC2CCN(c3cccc(-c4cc5ccc(N)cc5[nH]4)c3)CC2)CC1]
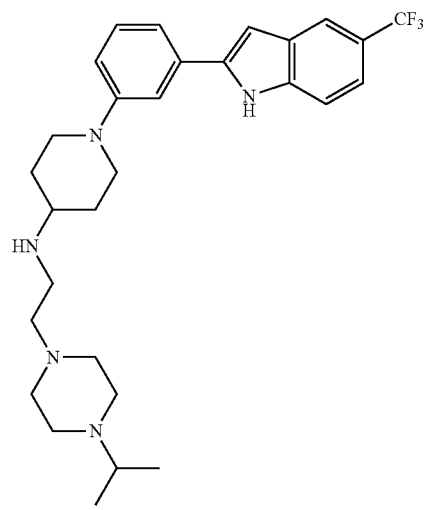 [SMILES: CC(C)N1CCN(CCNC2CCN(c3cccc(-c4cc5cc(C(F)(F)F)ccc5[nH]4)c3)CC2)CC1]

TABLE 1-continued
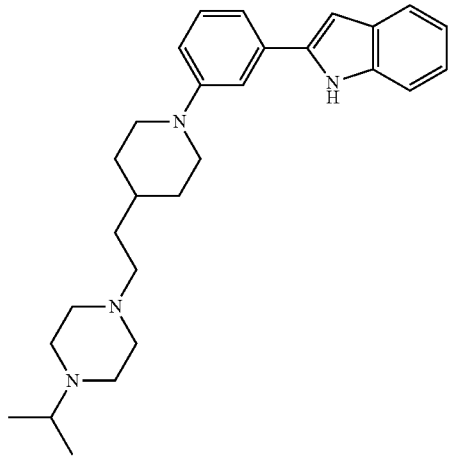 [SMILES: CC(C)N1CCN(CCC2CCN(c3cccc(-c4cc5ccccc5[nH]4)c3)CC2)CC1]
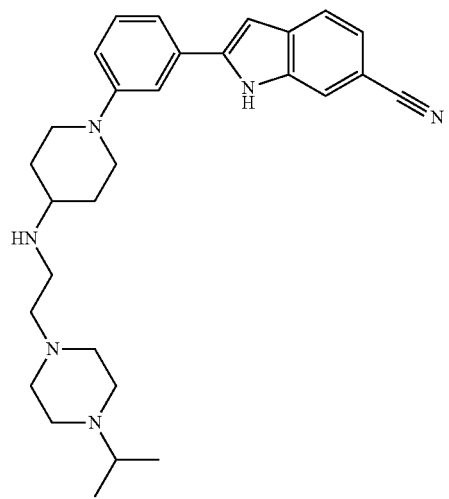 [SMILES: CC(C)N1CCN(CCNC2CCN(c3cccc(-c4cc5ccc(C#N)cc5[nH]4)c3)CC2)CC1]
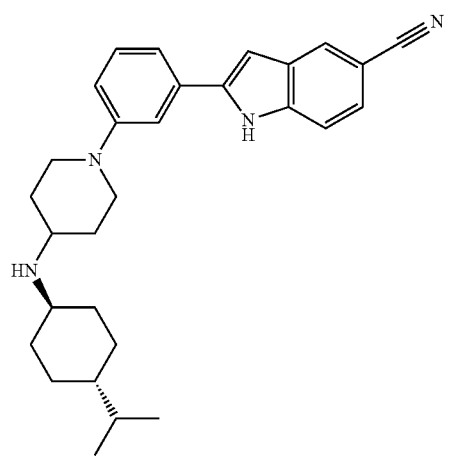 [SMILES: CC(C)[C@H]1CC[C@H](NC2CCN(c3cccc(-c4cc5cc(C#N)ccc5[nH]4)c3)CC2)CC1]

TABLE 1-continued
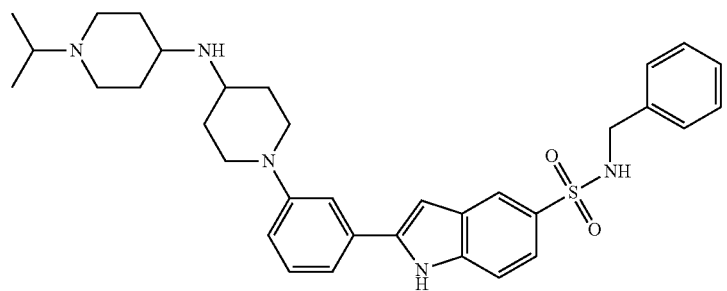 [SMILES: CC(C)N1CCC(NC2CCN(c3cccc(-c4cc5cc(S(=O)(=O)NCc6ccccc6)ccc5[nH]4)c3)CC2)CC1]
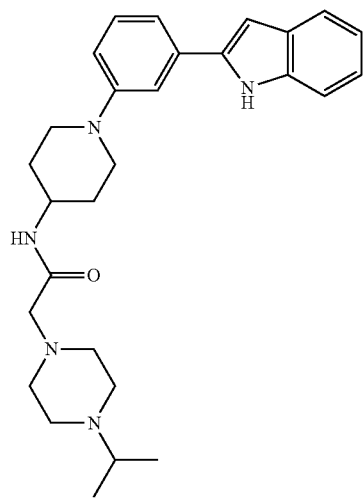 [SMILES: CC(C)N1CCN(CC(=O)NC2CCN(c3cccc(-c4cc5ccccc5[nH]4)c3)CC2)CC1]
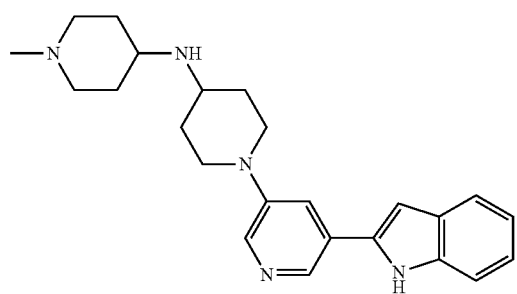 [SMILES: CN1CCC(NC2CCN(c3cncc(-c4cc5ccccc5[nH]4)c3)CC2)CC1]
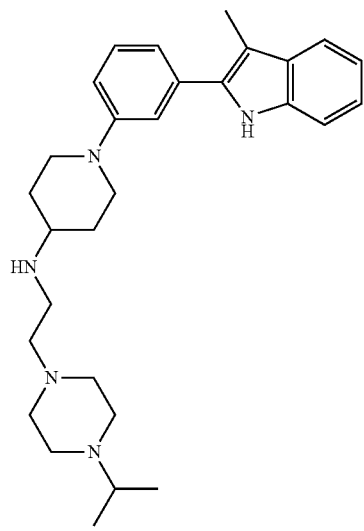 [SMILES: Cc1c(-c2cccc(N3CCC(NCCN4CCN(C(C)C)CC4)CC3)c2)[nH]c2ccccc12]

TABLE 1-continued
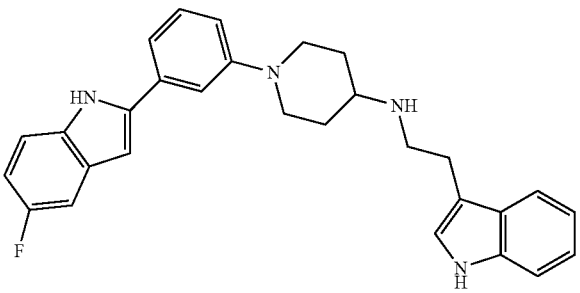 [SMILES: Fc1ccc2[nH]c(-c3cccc(N4CCC(NCCc5c[nH]c6ccccc56)CC4)c3)cc2c1]
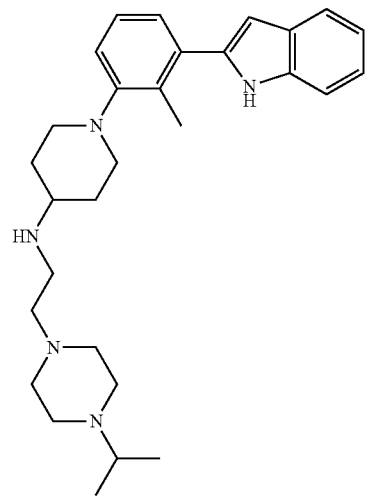 [SMILES: Cc1c(-c2cc3ccccc3[nH]2)cccc1N1CCC(NCCN2CCN(C(C)C)CC2)CC1]
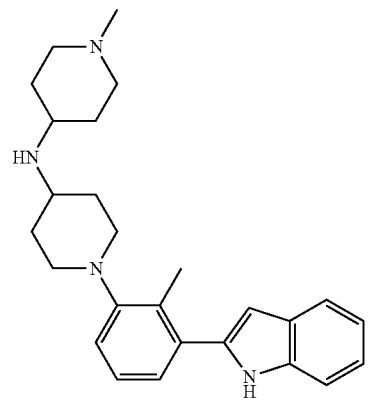 [SMILES: Cc1c(-c2cc3ccccc3[nH]2)cccc1N1CCC(NC2CCN(C)CC2)CC1]
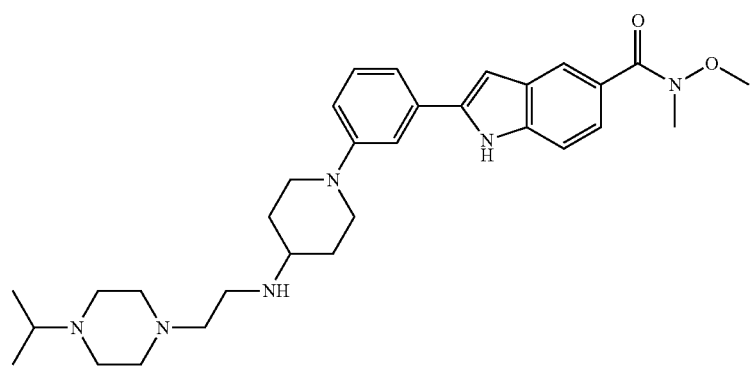 [SMILES: CON(C)C(=O)c1ccc2[nH]c(-c3cccc(N4CCC(NCCN5CCN(C(C)C)CC5)CC4)c3)cc2c1]

TABLE 1-continued
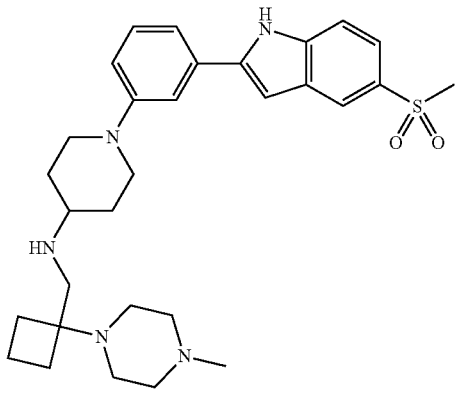 [SMILES: CN1CCN(C2(CNC3CCN(c4cccc(-c5cc6cc(S(C)(=O)=O)ccc6[nH]5)c4)CC3)CCC2)CC1]
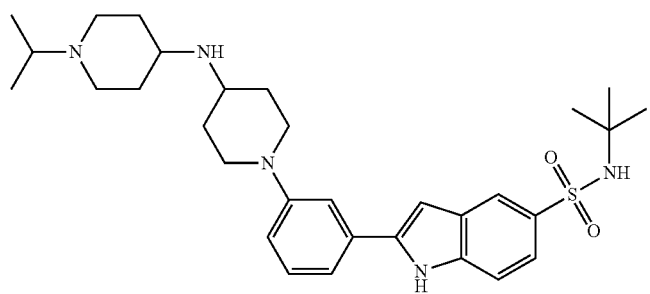 [SMILES: CC(C)N1CCC(NC2CCN(c3cccc(-c4cc5cc(S(=O)(=O)NC(C)(C)C)ccc5[nH]4)c3)CC2)CC1]
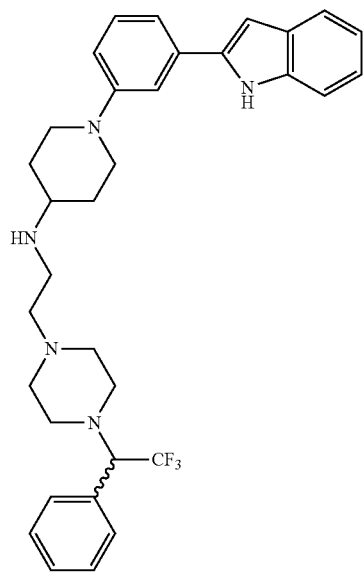 [SMILES: FC(F)(F)C(c1ccccc1)N1CCN(CCNC2CCN(c3cccc(-c4cc5ccccc5[nH]4)c3)CC2)CC1]

TABLE 1-continued
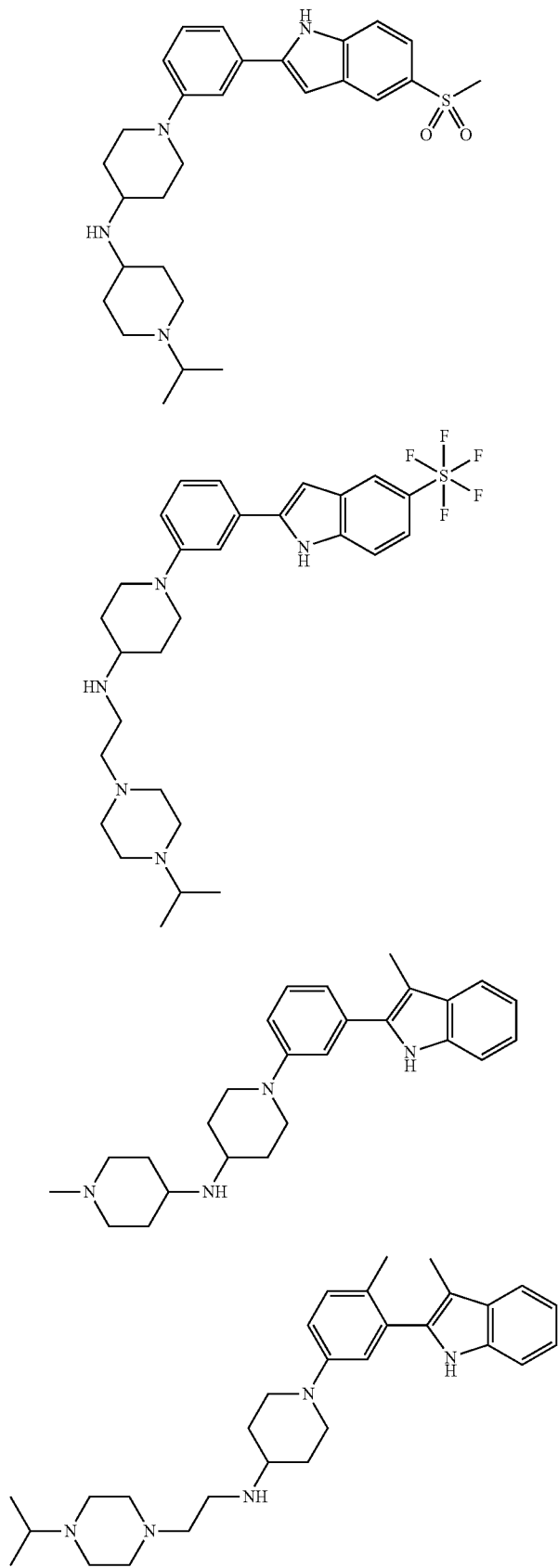

TABLE 1-continued
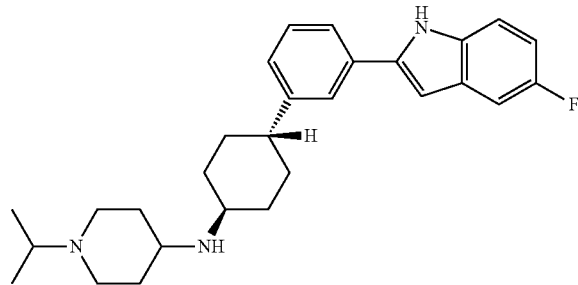 [SMILES: CC(C)N1CCC(N[C@H]2CC[C@H](c3cccc(-c4cc5cc(F)ccc5[nH]4)c3)CC2)CC1]
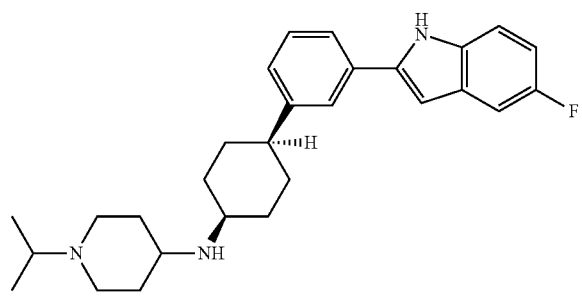 [SMILES: CC(C)N1CCC(N[C@H]2CC[C@@H](c3cccc(-c4cc5cc(F)ccc5[nH]4)c3)CC2)CC1]
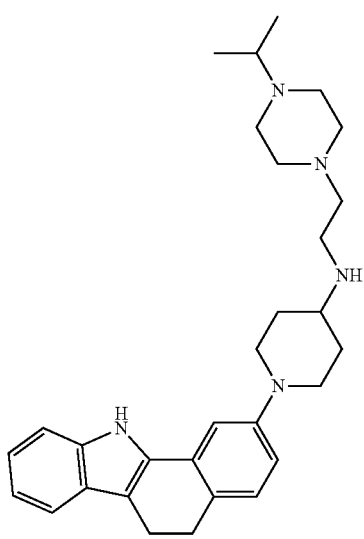 [SMILES: CC(C)N1CCN(CCNC2CCN(c3ccc4c(c3)-c3[nH]c5ccccc5c3CC4)CC2)CC1]
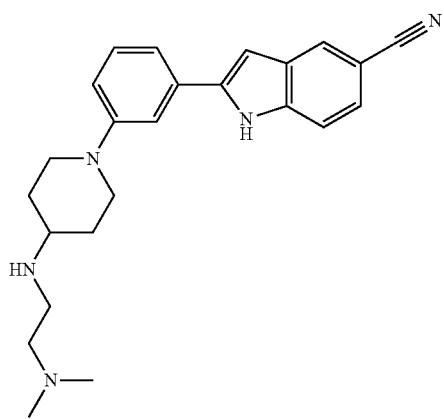 [SMILES: CN(C)CCNC1CCN(c2cccc(-c3cc4cc(C#N)ccc4[nH]3)c2)CC1]

TABLE 1-continued
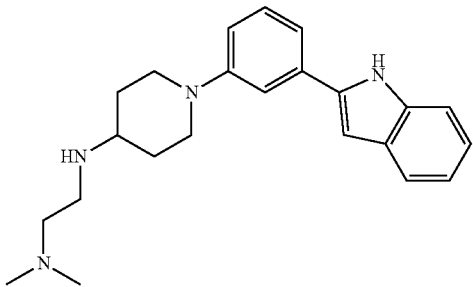 [SMILES: CN(C)CCNC1CCN(c2cccc(-c3cc4ccccc4[nH]3)c2)CC1]
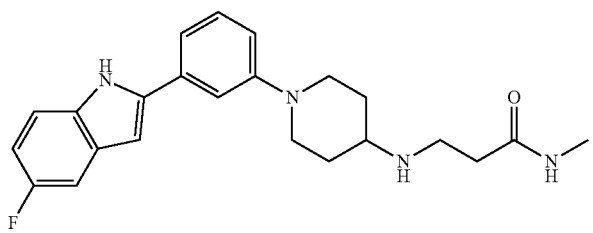 [SMILES: CNC(=O)CCNC1CCN(c2cccc(-c3cc4cc(F)ccc4[nH]3)c2)CC1]
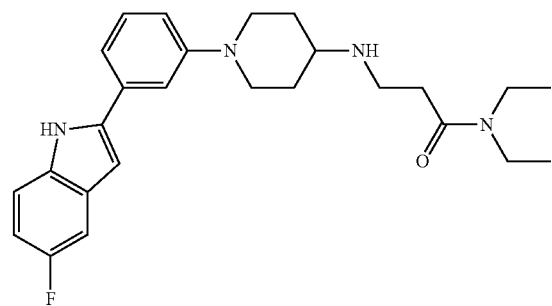 [SMILES: CCN(CC)C(=O)CCNC1CCN(c2cccc(-c3cc4cc(F)ccc4[nH]3)c2)CC1]
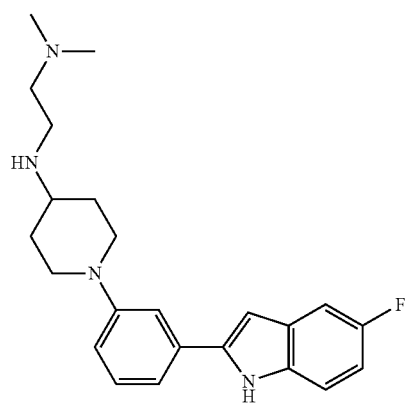 [SMILES: CN(C)CCNC1CCN(c2cccc(-c3cc4cc(F)ccc4[nH]3)c2)CC1]

TABLE 1-continued
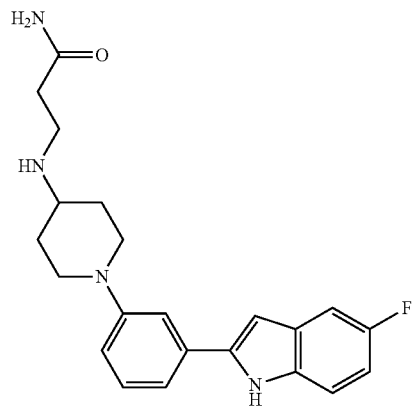 [SMILES: NC(=O)CCNC1CCN(c2cccc(-c3cc4cc(F)ccc4[nH]3)c2)CC1]
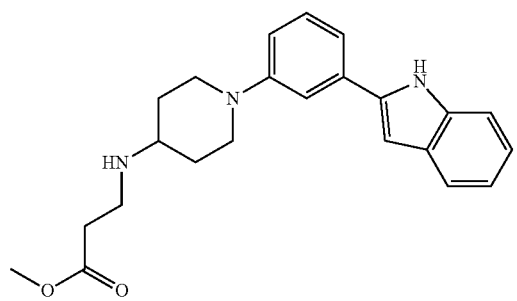 [SMILES: COC(=O)CCNC1CCN(c2cccc(-c3cc4ccccc4[nH]3)c2)CC1]
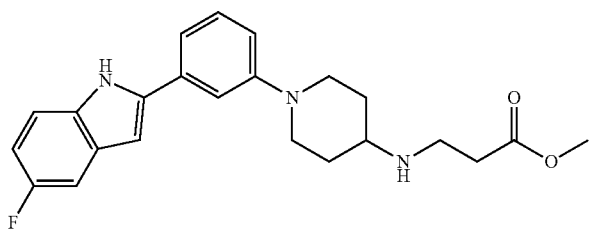 [SMILES: COC(=O)CCNC1CCN(c2cccc(-c3cc4cc(F)ccc4[nH]3)c2)CC1]
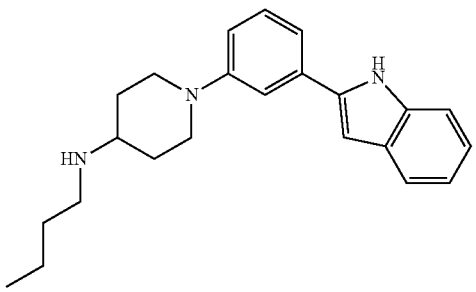 [SMILES: CCCCNC1CCN(c2cccc(-c3cc4ccccc4[nH]3)c2)CC1]
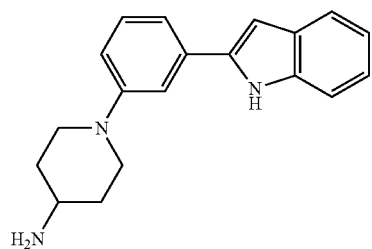 [SMILES: NC1CCN(c2cccc(-c3cc4ccccc4[nH]3)c2)CC1]

TABLE 1-continued
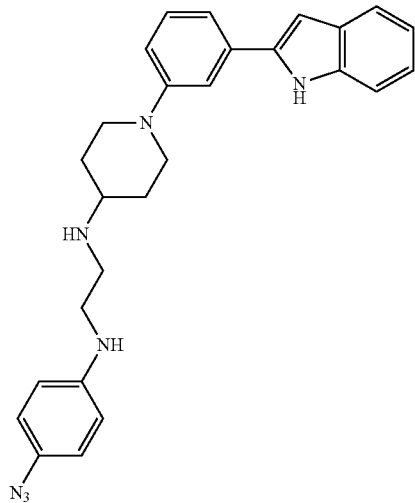 [SMILES: [N-]=[N+]=Nc1ccc(NCCNC2CCN(c3cccc(-c4cc5ccccc5[nH]4)c3)CC2)cc1]
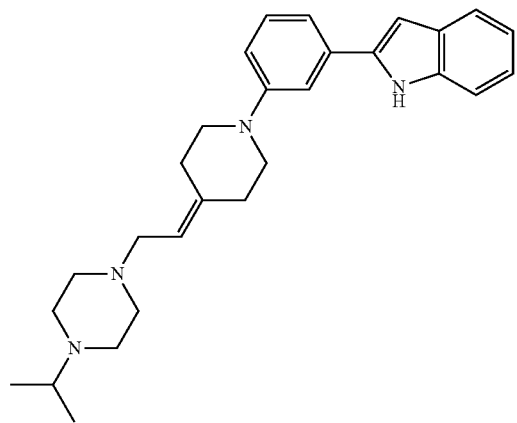 [SMILES: CC(C)N1CCN(CC=C2CCN(c3cccc(-c4cc5ccccc5[nH]4)c3)CC2)CC1]
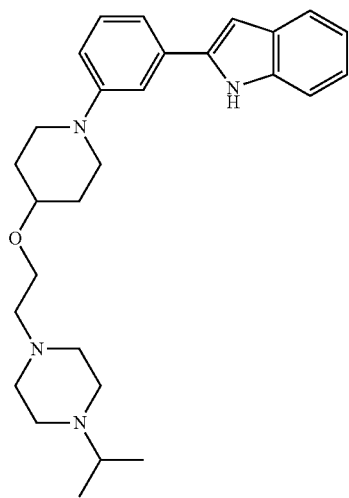 [SMILES: CC(C)N1CCN(CCOC2CCN(c3cccc(-c4cc5ccccc5[nH]4)c3)CC2)CC1]

TABLE 1-continued

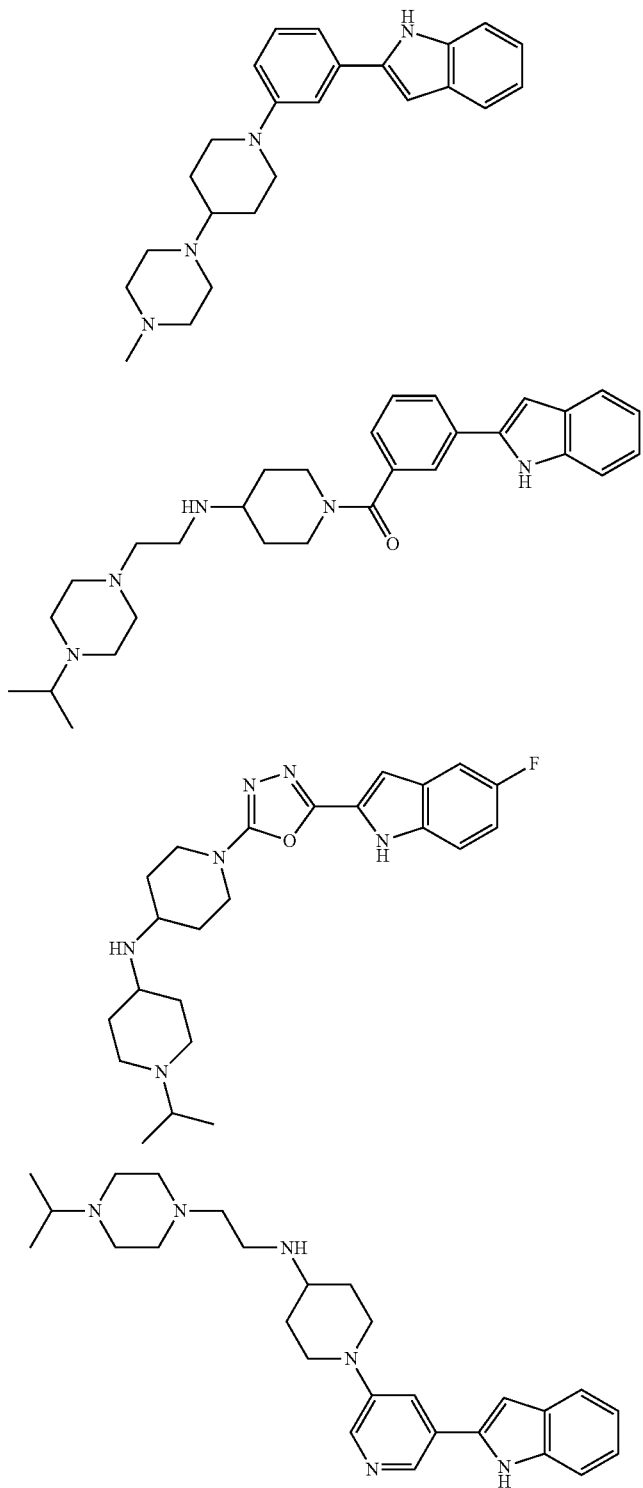

II. Methods of Treatment

In some embodiments, the compounds of the present disclosure have an ADP-Glo™ IC$_{50}$ value of less than about 25 μM, meaning that at a concentration of 25 μM, the compounds inhibit expression of p97 by half. In other embodiments, the compounds of the invention have an ADP-Glo™ IC$_{50}$ value of less than about 50 μM, less than about 45 μM, less than about 40 μM, less than about 35 μM, less than about 30 μM, less than about 25 μM, less than about 20 μM, less than about 15 μM, less than about 10 μM, or less than about 5 μM. ADP-Glo™ (Promega Corp.) is a bioluminescent, homogeneous assay that measures ADP formed from a biochemical reactions. Because of its high sensitivity, the assay is suitable for monitoring enzyme activities at very early substrate conversions requiring very low amount of enzymes. This is critical since inhibitor potency has to be demonstrated at the cellular level where ATP is present at millimolar concentrations.

One aspect of the present invention includes methods of inhibiting p97 in a subject in need thereof. In some embodiments, the treatment of the subject in need thereof comprises administering a compound of the present disclosure (e.g., a compound of Formula (I), (II) or Table 1) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

Another aspect of the present invention includes methods of treating cancers or neurodegenerative disorders susceptible to treatment by p97 inhibition in a subject diagnosed as having, suspected as having, or at risk of having cancer or a neurodegenerative disorder susceptible to treatment by p97 inhibition. As such, some embodiments of the disclosure include methods of treating a subject in need thereof who is suffering from, suspected as having, or at risk of having cancer or a neurodegenerative disorder susceptible to treatment by p97 inhibition. In some embodiments, the treatment of the subject in need thereof comprises administering a compound of the present disclosure (e.g., a compound of Formula (I), (II) or Table 1) to the subject suspected of, or already suffering from cancer or a neurodegenerative disorder susceptible to treatment by p97 inhibition, in an amount sufficient to cure, or at least partially arrest, the symptoms of the disease, including its complications and intermediate pathological phenotypes in development of the disease.

In some embodiments, cancers susceptible to treatment by p97 inhibition include but are not limited to solid tumor cancers, non-small cell lung carcinoma, multiple myeloma, or mantle cell lymphoma. In some embodiments, cancers susceptible to treatment by p97 inhibition include a solid tumor. See Valle et al., "Critical Role of VCP/p97 in the Pathogenesis and Progression of Non-Small Cell Lung Carcinoma," *PlosOne*, 6(12): e29073 (2011) and Deshaies et al., "Proteotoxic crisis, the ubiquitin-proteasome system, and cancer therapy," *BMC Biology*, 72(94) (2014).

In some embodiments, neurodegenerative disorders susceptible to treatment by p97 inhibition include but are not limited to inclusion body myopathy (IBM), Paget's disease of the bone (PDB), frontotemporal dementia (FTD) and amyotrophic lateral sclerosis (ALS)). Neurodegenerative disorders also include subjects having p97 mutations, and symptoms manifesting as, for example, Parkinsonism, ataxia, cataracts, dilated cardiomyopathy, hepatic fibrosis, and hearing loss.

The compound may be included in a pharmaceutical formulation such as those disclosed herein, and may be administered in any pharmaceutically acceptable manner, including methods of administration described herein.

The compounds useful in the methods of the present invention is administered to a mammal in an amount effective in treating or preventing elevated activity of p97, cancers susceptible to treatment by p97 inhibition, or neurodegenerative disorders susceptible to treatment by p97 inhibition. The therapeutically effective amount can be determined by methods known in the art.

An effective amount of a compound useful in the methods of the present invention, for example in a pharmaceutical composition, may be administered to a mammal in need thereof by any of a number of well-known methods for administering pharmaceutical compounds. The compound may be administered systemically or locally. In one embodiment, the compound is administered intravenously. For example, the compounds useful in the methods of the present technology may be administered via rapid intravenous bolus injection. In some embodiments, the compound is administered as a constant rate intravenous infusion. The compound may also be administered orally, topically, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord.

The compounds useful in the methods of the present technology may also be administered to mammals by sustained or controlled release, as is known in the art. Sustained release administration is a method of drug delivery to achieve a certain level of the drug over a particular period of time. The level typically is measured by serum or plasma concentration.

In one preferred embodiment, the compounds are administered orally. In one preferred embodiment, the compounds are administered intravenously. In one preferred embodiment, the compounds are administered at less than 1 gram per day.

III. Pharmaceutical Formulations

For oral administration, liquid or solid dose formulations may be used. Some examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant (such as a nonionic, ionic, anionic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. In some embodiments, the stabilizer or combination of stabilizers constitutes from about 0.1% to about 10% weight for weight of the compound.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v).

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In one embodiment, the mammal is a human.

IV. Combination Therapy

In some embodiments, the compounds of the present disclosure may be combined with one or more additional therapies for the prevention or treatment of a disease or condition amenable to treatment by inhibition of p97. Additional therapeutic agents or active agents include, but are not limited to, alkylating agents, nitrosoureas, antimetabolites, antitumor antibiotics, plant vinca alkaloids, and steroid hormones.

The multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

In one embodiment, the compounds of the present disclosure can be combined with proteosome inhibitors. In another embodiment, the compounds of the present disclosure can be combined with other anti-cancer agents. In another embodiment, the compounds of the present disclosure can be combined with heat shock protein (HSP) inhibitors. In another embodiment, the compounds of the present disclosure can be combined with two or more of proteasome inhibitors, HSP inhibitors, and other anti-cancer agents.

V. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Hence, isotopically labeled compounds are within the scope of the invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyfazaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The term "amine" (or "amino") as used herein refers to —NHR$^4$ and —NR$^5$R$^6$ groups, wherein R$^4$, R$^5$ and R$^6$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH$_2$, methylamino, dimethylamino, ethylamino, diethylamino, propylamino, isopropylamino, phenylamino, or benzylamino.

The term "amide" refers to a —NR'R"C(O)— group wherein R and R each independently refer to a hydrogen, (C$_1$-C$_5$)alkyl, or (C$_3$-C$_6$)aryl.

The term 'nitrile or cyano" can be used interchangeably and refer to a —CN group which is bound to a carbon atom of a heteroaryl ring, aryl ring and a heterocycloalkyl ring.

The substituent —CO$_2$H, may be replaced with bioisosteric replacements such as:

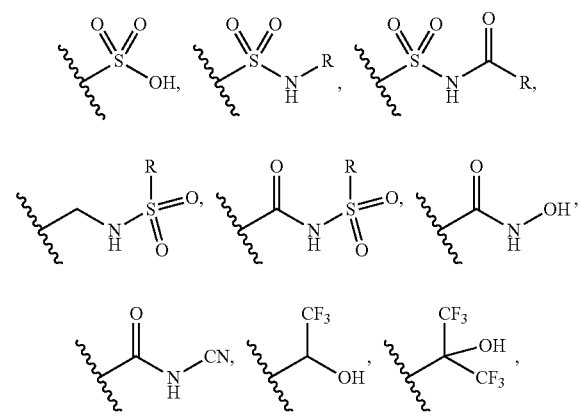

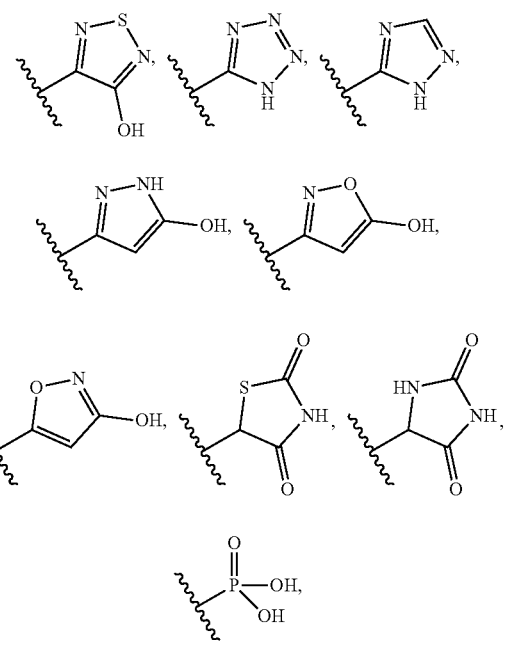

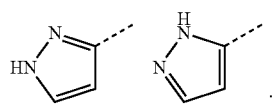

and the like, wherein R has the same definition as R' and R" as defined herein. See, e.g., THE PRACTICE OF MEDICINAL CHEMISTRY (Academic Press: New York, 1996), at page 203.

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

VI. Working Examples

The present technology is further illustrated by the following examples, which should not be construed as limiting in any way.

General information. All non-aqueous reactions were carried out under a nitrogen atmosphere in oven- or flame-dried glassware unless otherwise noted. Anhydrous tetrahydrofuran and diethyl ether were distilled from sodium benzophenone ketyl; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 $F_{254}$ plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g $Ce(NH_4)_2(NO_3)_6$, 12 g $(NH_4)_6Mo_7O_{24} \cdot 4H_2O$, and 28 mL conc. $H_2SO_4$ in 235 mL water), or vanillin (6 g vanillin and 1.5 mL conc. $H_2SO_4$ in 100 mL EtOH). Flash chromatography was performed with SiliCycle silica gel 60 (230-400 mesh) or with ISCO MPLC. $^1$H and $^{13}$C NMR spectra were recorded on Bruker Avance 300, 400, or 500 MHz spectrometers, using the residual solvent as an internal standard. IR spectra were obtained on a Smiths IdentifyIR or PerkinElmer Spectrum 100. HRMS data were obtained on a Thermo Scientific Exactive HRMS coupled to a Thermo Scientific Accela HPLC system using a 2.1×50 mm 3.5 μm Waters XTerra $C_{18}$ column eluting with $MeCN/H_2O$ containing 0.1% formic acid. Purity of compounds was assessed using the same HPLC system with either the PDA or an Agilent 385 ELSD. All final screening samples passed QC based on >95% purity by LC/MS/ELSD analysis.

General Synthetic Methods

The compounds of the present disclosure can be prepared using the following general methods and procedures. The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley, and Sons, 1991), *Rodd's Chemistry of Carbon Compounds*, Volumes 1-5, and Supplemental (Elsevier Science Publishers, 1989), *Organic Reactions*, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989).

More specifically, compounds provided herein can be synthesized as shown below (see Schemes 1 and 2), and following adaptations of the methods shown below and/or methods known to a skilled artisan and/or by using different commercially available starting materials.

Scheme 1. Method A

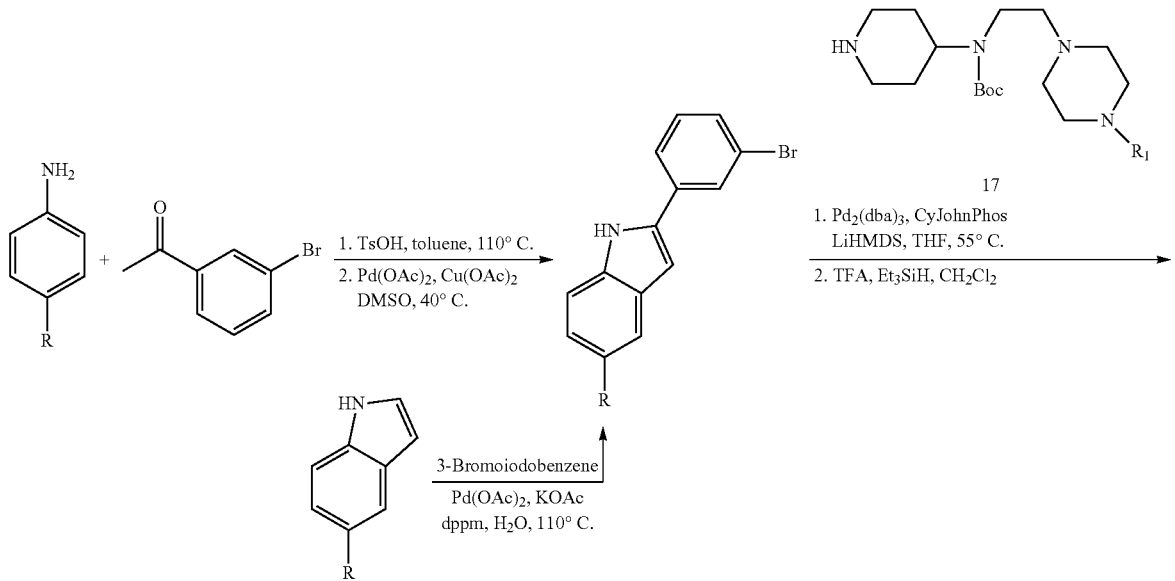

Final Product

Scheme 2. Method B

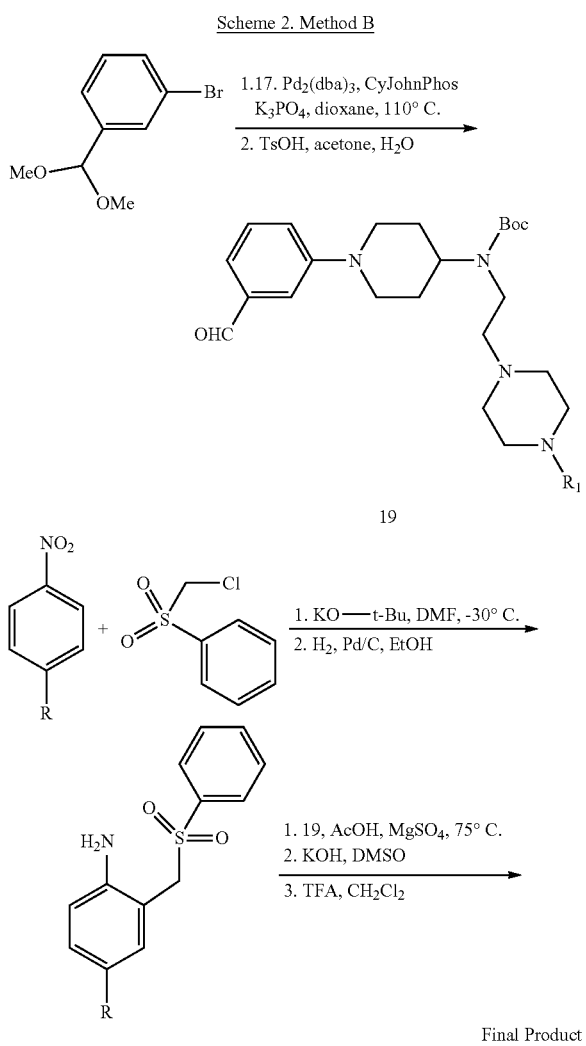

Synthesis of tert-Butyl (2-(4-isopropylpiperazin-1-yl)ethyl)(piperidin-4-yl)carbamate (17)

A solution of benzyl 4-oxopiperidine-1-carboxylate (1.54 g, 6.61 mmol), 2-(4-isopropylpiperazin-1-yl)ethan-1-amine (1.03 g, 6.01 mmol, Tapia, I.; Alonso-Cires, L.; Lopez-Tudanca, P. L.; Mosquera, R.; Labeaga, L.; Innerarity, A.; Orjales, A. *J. Med. Chem.* 1999, 42, 2870-2880), and AcOH (52.2 µL, 0.902 mmol) in anhydrous $CH_2Cl_2$ (100 mL) was treated with $NaBH(OAc)_3$ (1.94 g, 9.02 mmol). The reaction mixture was stirred at room temperature overnight, diluted with $CH_2Cl_2$ (100 mL), washed with sat. $NaHCO_3$, brine, dried ($Na_2SO_4$), and evaporated to give benzyl 4-((2-(4-isopropylpiperazin-1-yl)ethyl)amino)piperidine-1-carboxylate (2.33 g, quant.) as a pale yellow oil that was used without further purification: $^1$H NMR (300 MHz, $CDCl_3$) δ 7.37-7.32 (m, 5H), 5.12 (s, 2H), 4.11 (app d, J=10.3 Hz, 2H), 2.88 (app t, J=11.8 Hz, 2H), 2.74-2.47 (m, 14H), 1.85 (d, J=12.6 Hz, 2H), 1.35-1.22 (m, 2H), 1.06 (d, J=6.5 Hz, 6H).

A solution of benzyl 4-((2-(4-isopropylpiperazin-1-yl)ethyl)amino)piperidine-1-carboxylate (8.34 g, 21.5 mmol) in anhydrous $CH_2Cl_2$ (350 mL) was treated with $Boc_2O$ (8.43 g, 38.6 mmol). The reaction mixture was stirred at room temperature overnight, diluted with $CH_2Cl_2$ (350 mL), washed with sat. $NaHCO_3$, brine, dried ($Na_2SO_4$), evaporated, and purified by chromatography on $SiO_2$ (2% MeOH/$CH_2Cl_2$ with 1% TEA) followed by chromatography on basic $Al_2O_3$ (0 to 1% MeOH/$CH_2Cl_2$) to give benzyl 4-((tert-butoxycarbonyl)(2-(4-isopropylpiperazin-1-yl)ethyl)amino)piperidine-1-carboxylate (8.08 g, 77%) as a colorless oil: $^1$H NMR (400 MHz, $CDCl_3$) δ 7.38-7.29 (m, 5H), 5.11 (s, 2H), 4.26 (bs, 2H), 4.09 (bs, 1H), 3.17 (bs, 2H), 2.78 (bs, 2H), 2.66-2.40 (m, 11H), 1.65-1.56 (m, 4H), 1.45 (s, 9H), 1.03 (d, J=6.5 Hz, 6H).

A solution of benzyl 4-((tert-butoxycarbonyl)(2-(4-isopropylpiperazin-1-yl)ethyl)amino)piperidine-1-carboxylate (2.54 g, 5.20 mmol) in THF (120 mL) was treated with 10% Pd/C (0.512 g, 0.480 mmol). The reaction mixture was subjected to 3 cycles of vacuum/hydrogen backfill and stirred for 3 d under a hydrogen atmosphere. The reaction mixture was filtered through a pad of Celite® and concentrated to give tert-butyl (2-(4-isopropylpiperazin-1-yl)ethyl)(piperidin-4-yl)carbamate (17, 1.80 g, 98%) as a colorless oil: $^1$H NMR (300 MHz, $CDCl_3$) δ 4.01 (bs, 1H), 3.23 (app t, J=5.4 Hz, 2H), 3.11 (d, J=11.8 Hz, 2H), 2.68-2.43 (m, 13H), 1.68-1.65 (m, 2H), 1.60-1.52 (m, 2H), 1.46 (s, 9H), 1.04 (d, J=6.5 Hz, 6H); HRMS (ESI) m/z calcd for $C_{19}H_{39}O_2N_4$ [M+H]$^+$ 355.3068, found 355.3067.

Synthesis of N-(2-(4-Isopropylpiperazin-1-yl)ethyl)-1-(3-(5-(trifluoromethyl)-1H-indol-2-yl)phenyl)piperidin-4-amine (12)

Scheme 3.

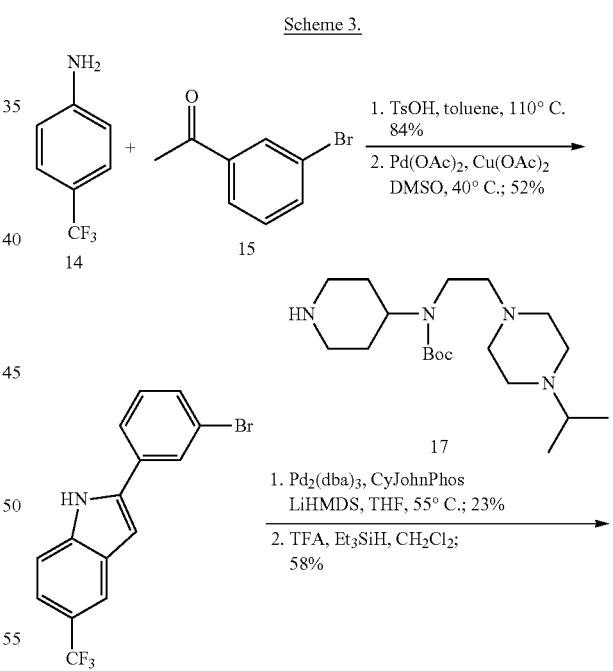

A solution of 3-bromoiodobenzene (32, 0.284 g, 1.00 mmol), 5-trifluoromethylindole (0.155 g, 0.840 mmol; Walkington, A.; Gray, M.; Hossner, F.; Kitteringham, J.; Voyle, M. *Synth. Commun.* 2003, 33, 2229-2233), $Pd(OAc)_2$ (10 mg, 0.04 mmol), bis(diphenylphosphino)methane (17 mg, 0.040 mmol), and KOAc (0.249 g, 2.51 mmol) in deoxygenated water (2 mL) was heated at 110° C. for 24 h, cooled to room temperature, diluted with EtOAc (10 mL) and 1 N HCl (5 mL), and extracted with EtOAc (2×10 mL). The combined organic layers were dried (MgSO₄), concentrated, and purified by chromatography on SiO₂ (10% EtOAc/petroleum ether). The residue was recrystallized (hexanes/CH₂Cl₂) to give 2-(3-bromophenyl)-5-(trifluoromethyl)-1H-indole (16, 139 mg, 49%) as a colorless solid: $^1$H NMR (400 MHz, CDCl₃) δ 8.48 (bs, 1H), 7.92 (s, 1H), 7.79 (s, 1H), 7.56 (d, J=7.6 Hz, 1H), 7.48 (d, J=7.9 Hz, 1H), 7.46-7.00 (m, 2H), 7.36-7.27 (m, 1H), 6.88 (d, J=1.6 Hz, 1H).

A solution of 2-(3-bromophenyl)-5-(trifluoromethyl)-1H-indole (16, 85 mg, 0.25 mmol), LiHMDS (0.10 g, 0.60 mmol), Pd₂(dba)₃ (5 mg, 0.005 mmol), and CyJohnPhos (7 mg, 0.02 mmol) in anhydrous THF was treated with tert-butyl (2-(4-isopropylpiperazin-1-yl)ethyl)(piperidin-4-yl)carbamate (17, 0.107 g, 0.300 mmol). The reaction mixture was heated at 55° C. overnight, cooled to room temperature, diluted with sat. NaHCO₃, and extracted with CH₂Cl₂ (3×). The combined organic layers were washed with brine, dried (Na₂SO₄), concentrated, and purified by chromatography on SiO₂ (2% MeOH/CH₂Cl₂ with 0.1% TEA) followed by chromatography on basic Al₂O₃ (CH₂Cl₂) to give tert-butyl (2-(4-isopropylpiperazin-1-yl)ethyl)(1-(3-(5-(trifluoromethyl)-1H-indol-2-yl)phenyl)piperidin-4-yl)carbamate (35 mg, 0.057 mmol, 23%) as a foam: IR (ATR) 3234, 2963, 2930, 2812, 1685, 1601, 1465, 1330, 1151, 1110, 1051 cm$^{-1}$; $^1$H NMR (400 MHz, CDCl₃) δ 9.19 (s, 1H), 7.89 (s, 1H), 7.48 (d, J=8.4 Hz, 1H), 7.38 (dd, J=8.4, 1.2 Hz, 1H), 7.31 (t, J=8.0 Hz, 1H), 7.23 (bs, 1H), 7.16 (bd, J=7.6 Hz, 1H), 6.90 (dd, J=7.8, 1.0 Hz, 1H), 6.84 (d, J=1.2 Hz, 1H), 4.12 (bs, 1H), 3.79 (bd, 7=4.0 Hz, 2H), 3.22 (bs, 2H), 2.82-2.47 (m, 13H), 1.76-1.75 (m, 3H), 1.48 (s, 9H), 1.25-1.22 (m, 1H), 1.11 (d, J=6.0 Hz, 6H); HRMS (ESI) m/z calcd for C₃₄H₄₇O₂N₅F₃ [M+H]⁺ 614.3676, found 614.3678.

A solution of TFA (0.43 mL, 5.7 mmol) and triethylsilane (92 μL, 0.57 mmol) in CH₂Cl₂ (1 mL) was added to a solution of tert-butyl (2-(4-isopropylpiperazin-1-yl)ethyl)(1-(3-(5-(trifluoromethyl)-1H-indol-2-yl)phenyl)piperidin-4-yl)carbamate (35 mg, 0.057 mmol) in CH₂Cl₂ (0.5 mL). The reaction mixture was stirred under an atmosphere of N₂ at room temperature for 1 h, concentrated, diluted with sat. NaHCO₃, and extracted with EtOAc (3×). The combined organic layers were washed with brine, dried (Na₂SO₄), concentrated, and purified by chromatography on SiO₂ (7 to 9% MeOH/CH₂Cl₂ with 0.1% TEA) followed by chromatography on basic Al₂O₃ (0 to 9% MeOH/CH₂Cl₂) to give A-(2-(4-isopropylpiperazin-1-yl)ethyl)-1-(3-(5-(trifluoromethyl)-1H-indol-2-yl)phenyl)piperidin-4-amine (12, 17 mg, 0.033 mmol, 58%) as a yellow oil: $^1$H NMR (500 MHz, CDCl₃) δ 8.83 (s, 1H), 7.89 (s, 1H), 7.44 (d, J=8.5 Hz, 1H), 7.40 (dd, J=8.5, 1.0 Hz, 1H), 7.33-7.30 (m, 1H), 7.22 (app s, 1H), 7.11 (d, J=7.5 Hz, 1H), 6.93 (dd, J=8.3, 2.3 Hz, 1H), 6.84 (d, J=1.5 Hz, 1H), 3.74 (app d, J=12.5 Hz, 2H), 2.85 (td, J=12.0, 1.8 Hz, 2H), 2.78 (t, J=6.3 Hz, 2H), 2.68-2.49 (m, 13H), 2.01 (bd, J=12.0 Hz, 2H), 1.54 (qd, J=11.6, 3.1 Hz, 2H), 1.05 (d, J=6.5 Hz, 6H); $^{13}$C NMR (125 MHz, CDCl₃) δ 152.2, 140.6, 138.1, 132.7, 129.9, 129.3, 128.7, 125.5 (q, J$_{CF}$=271.0 Hz), 122.7 (q, J$_{CF}$=31.6 Hz), 118.9 (q, J$_{CF}$=3.4 Hz), 118.3 (q, J$_{CF}$=4.2 Hz), 116.5, 113.6, 111.2, 100.5, 58.1, 55.2, 54.6, 53.7, 48.9, 48.6, 43.6, 32.7, 18.8; $^{19}$F NMR (376 MHz, CDCl₃) δ −60.4; HRMS (ESI) m/z calcd for C₂₉H₃₉N₅F₃ [M+H]⁺ 514.3152, found 514.3154.

Synthesis of 1-{3-[5-(Pentafluoro-λ⁶-sulfanyl)-1H-indol-2-yl]phenyl}-N-{2-[4-(propan-2-yl)piperazin-1-yl]ethyl}piperidin-4-amine (13)

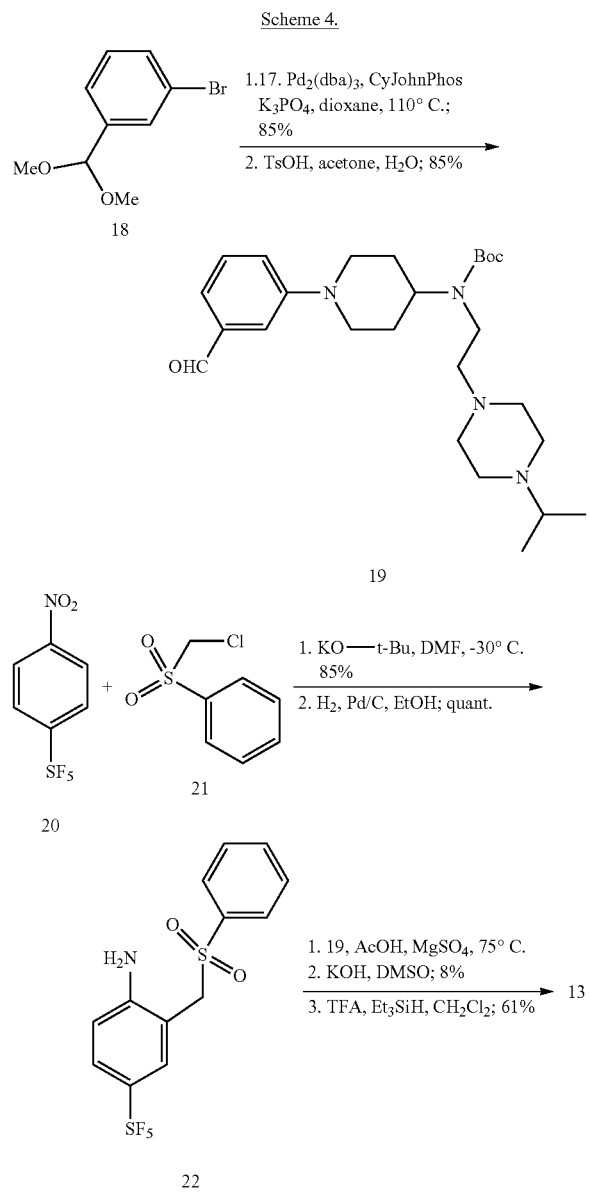

A suspension of 1-bromo-3-(dimethoxymethyl)benzene (18, 0.19 g, 0.82 mmol, Kumar et al., *Tetrahedron Lett.*, 46: 8319-8323 (2005)), 17 (0.32 g, 0.90 mmol) and K₃PO₄ (0.27 g, 1.2 mmol) in dry dioxane (2.5 mL) was degassed for 40 min by bubbling argon, then Pd₂(dba)₃ (8 mg, 0.008 mmol) and CyJohnPhos (12 mg, 0.032 mmol) were added. The flask was sealed and the reaction mixture was heated at 110° C. for 10 h, diluted with sat. NaHCO₃ and extracted with EtOAc (3×). The combined organic layers were washed with brine, dried (Na₂SO₄), and concentrated. The residue was dissolved in acetone (27 mL) and H₂O (3 mL) and treated with TsOH.H₂O (0.48 g, 2.5 mmol) at rt for 3 h, then diluted with sat. Na₂CO₃ and extracted with EtOAc (3×). The combined organic layers were washed with brine, dried ($Na_2SO_4$), and concentrated. The residue was purified by chromatography on $SiO_2$ (95:5 to 85:15 $CH_2Cl_2$/MeOH) to give tert-butyl (1-(3-formylphenyl)piperidin-4-yl)(2-(4-isopropylpiperazin-1-yl)ethyl)carbamate (19, 0.32 g, 0.70 mmol, 85% for two steps) as a pale yellow viscous oil: IR (ATR) 2961, 2931, 2808, 1685, 1595, 1450, 1365, 1175, 1145,776 $cm^{-1}$; $^1H$ NMR (500 MHz, $CD_2Cl_2$) δ 9.97 (s, 1H), 7.44 (t, J=7.9 Hz, 2H), 7.32 (d, J=7.4 Hz, 1H), 7.23 (dd, J=8.2, 2.4 Hz, 1H), 4.09 (t, J=1.9 Hz, 1H), 3.87 (d, J=12.5 Hz, 2H), 3.23 (s, 2H), 2.88 (t, 7=11.6 Hz, 2H), 2.70-2.45 (m, 11H), 1.90-1.80 (m, 4H), 1.48 (s, 9H), 1.06 (d, J=6.5 Hz, 6H); $^{13}C$ NMR (125 MHz, $CD_2Cl_2$) δ 192.6, 155.1, 151.7, 137.5, 129.7, 122.0, 120.9, 115.4, 79.3, 58.3, 54.5, 49.1, 48.5, 40.6, 29.9, 28.2, 18.2; HRMS (ESI) m/z calcd for $C_{26}H_{43}O_3N_4$ $[M+H]^+$ 459.3330, found 459.3329.

A solution of 1-nitro-4-(pentafluoro-$\lambda^6$-sulfanyl)benzene (20, 1.0 g, 4.0 mmol) and ((chloromethyl)sulfonyl)benzene (21, 0.77 g, 4.0 mmol) in DMF (4.0 mL) was added dropwise to a solution of t-BuOK (1.6 g, 14 mmol) in DMF (10 mL) at −30° C. The reaction mixture was stirred for 30 min at −30° C., quenched by addition of aq HCl (30 mL, 1 M), and extracted with $CH_2Cl_2$ (3×). The combined organic layers were washed with brine, dried ($Na_2SO_4$), and concentrated. The crude residue was purified by chromatography on $SiO_2$ (75:25 hexanes/EtOAc) to afford pentafluoro (4-nitro-3-((phenylsulfonyl)methyl)phenyl)-$\lambda^6$-sulfane) Iakobson, G.; Pošta, M.; Beier, P. *Synlett* 2013; 24, 855-859) (1.4 g, 3.4 mmol, 86%) as a pale yellow solid: $^1H$ NMR (400 MHz, $CDCl_3$) δ 8.12 (d, J=8.9 Hz, 1H), 7.95 (dd, J=8.9, 2.3 Hz, 1H), 7.74-7.69 (m, 4H), 7.56 (t, J=7.8 Hz, 2H), 4.98 (s, 2H); $^{13}C$ NMR (100 MHz, $CDCl_3$) δ 155.8 (quintuplet, $J_{CF}$=19.7), 150.6, 137.4, 134.6, 131.91, 131.86, 131.82, 129.6, 128.4, 127.97, 127.93, 127.88, 126.1, 124.5, 58.4.

A suspension of pentafluoro(4-nitro-3-((phenylsulfonyl)methyl)phenyl)-$\lambda^6$-sulfane (1.4 g, 3.5 mmol) and 10% Pd/C (0.11 g, 0.10 mmol) in EtOH (100 mL) was treated with $H_2$ (balloon, 1 atm) at room temperature for 4 h. The mixture was filtered on Celite® and concentrated to afford a pale yellow solid. The solid was suspended in $Et_2O$ and filtered. The residue was washed with cold $Et_2O$ to give 4-(pentafluoro-$\lambda^6$-sulfanyl)-2-((phenylsulfonyl)methyl)aniline (22, 0.5 g) as a white-pale yellow solid. More material was collected from concentration of the mother liquor as a pale yellow solid (0.7 g). The solids were combined to give 4-(pentafluoro-$\lambda^6$-sulfanyl)-2-((phenylsulfonyl)methyl)aniline (22, 1.2 g, 3.5 mmol, quant) that was used in the next step without further purification: $^1H$ NMR (400 MHz, MeOD) δ 7.79-7.71 (m, 3H), 7.68 (dd, J=9.1, 2.6 Hz, 1H), 7.59 (t, J=7.8 Hz, 2H), 7.39 (d, J=9.1 Hz, 1H), 7.06 (d, J=2.5 Hz, 1H), 4.58 (s, 2H).

A suspension of 4-(pentafluoro-$\lambda^6$-sulfanyl)-2-[(phenylsulfonyl)methyl]aniline (22, 0.20 g, 0.54 mmol), aldehyde 19 (0.49 g, 1.1 mmol), and $MgSO_4$ (0.32 g, 2.7 mmol) in acetic acid (2 mL) was heated at 75° C. for 14 h, concentrated, basified with $NaHCO_3$ and extracted with EtOAc (3×). The combined organic layers were washed with brine, dried ($Na_2SO_4$) and concentrated. The residue was dissolved in dry DMSO (4 mL) and added to a suspension of powdered KOH (0.15 g, 2.7 mmol) in dry DMSO (2 mL). The reaction mixture was stirred at rt for 90 min, then acidified to pH 8 with sat. $NH_4Cl$, and extracted with EtOAc (3×). The combined organic layers were washed with brine, dried ($Na_2SO_4$) and concentrated. The crude residue was purified by chromatography on $SiO_2$ (7:3, EtOAc/MeOH) to provide tert-butyl (2-(4-isopropylpiperazin-1-yl)ethyl)(1-(3-(5-(pentafluoro-$\lambda^6$-sulfanyl)-1H-indol-2-yl)phenyl)piperidin-4-yl)carbamate (0.030 g, 0.045 mmol, 8%) as a pale yellow foam: $^1H$ NMR (400 MHz, $CDCl_3$) δ 9.33 (s, 1H), 8.07 (d, J=1.8 Hz, 1H), 7.59 (dd, J=9.0, 2.1 Hz, 1H), 7.41 (d, J=8.9 Hz, 1H), 7.35 (t, J=7.9 Hz, 1H), 7.23 (s, 1H), 7.17 (d, J=7.6 Hz, 1H), 6.94 (d, J=7.7 Hz, 1H), 6.88 (d, J=0.7 Hz, 1H), 3.82-3.79 (m, 2H), 3.26 (t, J=1.1 Hz, 2H), 2.79-2.51 (m, 13H), 1.79 (s, 4H), 1.51 (s, 9H), 1.08 (d, J=6.5 Hz, 6H).

A solution of trifluoroacetic acid (1 mL) in $CH_2Cl_2$ (1 mL) was added to a solution of tert-butyl (2-(4-isopropylpiperazin-1-yl)ethyl)(1-(3-(5-(pentafluoro-$\lambda^6$-sulfanyl)-1H-indol-2-yl)phenyl)piperidin-4-yl)carbamate (0.025 g, 0.037 mmol) in $CH_2Cl_2$ (1 mL). The reaction mixture was stirred under $N_2$ at room temperature for 1 h, concentrated, diluted with $NaHCO_3$, extracted with EtOAc (3×), washed with brine, dried ($Na_2SO_4$) and concentrated. The crude residue was purified by chromatography on $SiO_2$ (100:8:1 to 100:15:1, $CH_2Cl_2$/MeOH/$NEt_3$). Purified fractions were concentrated and subsequently filtered through basic $Al_2O_3$ (100:0 then 100:10, $CH_2Cl_2$/MeOH) to provide N-(2-(4-isopropylpiperazin-1-yl)ethyl)-1-(3-(5-(pentafluoro-$\lambda^6$-sulfanyl)-1H-indol-2-yl)phenyl)piperidin-4-amine (13, 0.013 g, 0.023 mmol, 61%) as a white foam: IR(ATR) 3147, 2923, 2852, 2815, 1603, 1458, 1383, 1148, 839, 809 $cm^{-1}$; $^1H$ NMR (400 MHz, MeOD) δ 8.05 (d, J=2.0 Hz, 1H), 7.55 (dd, J=9.0, 2.1 Hz, 1H), 7.48 (d, J=9.0 Hz, 1H), 7.43 (s, 1H), 7.34-7.29 (m, 2H), 6.99-6.96 (m, 2H), 3.82 (d, J=12.6 Hz, 2H), 2.85-2.76 (m, 4H), 2.67-2.51 (m, 13H), 2.03 (d, J=11.7 Hz, 2H), 1.54 (dq, J=11.8, 3.2 Hz, 2H), 1.09 (d, J=6.5 Hz, 6H); $^{13}C$ NMR (100 MHz, MeOD)<δ 152.0, 146.8, 146.7, 146.5, 141.5, 137.8, 132.5, 129.3, 127.9, 118.5, 118.4, 118.3, 118.2, 116.6, 116.3, 113.3, 110.1, 99.6, 57.0, 54.8, 54.5, 52.7, 42.4, 31.4, 17.3; HRMS (ESI) m/z calcd for $C_{28}H_{39}N_5F_5S$ $[M+H]^+$ 572.2841, found 572.2836.

Synthesis of N-(2-(4-Isopropylpiperazin-1-yl)ethyl)-1-(3-(5-nitro-1H-indol-2-yl)phenyl)piperidin-4-amine (23)

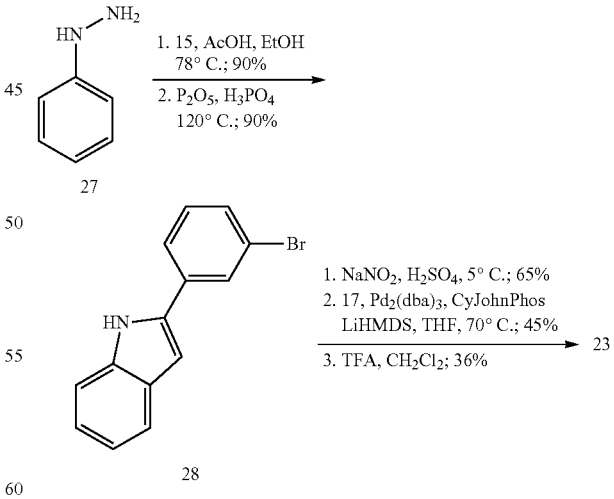

Scheme 5.

To a solution of phenylhydrazine (27, 1.80 g, 16.6 mmol) and 3'-bromoacetophenone (15, 3.31 g, 16.6 mmol) in EtOH (100 mL) was treated with AcOH (0.050 mL, 0.86 mmol). The mixture was heated at reflux for 2 h under nitrogen, and then concentrated. The residue was recrystallized from hexanes/EtOAc (4:1) and filtered to afford (E)-1-(1-(3- bromophenyl)ethylidene)-2-phenylhydrazine as a pale yellow solid (4.30 g, 14.9 mmol, 90%). This compound was quite unstable and was used immediately for the next conversion.

A suspension of $P_2O_5$ (12.8 g, 45.1 mmol) and concentrated $H_3PO_4$ (8 mL) was heated at 100° C. under nitrogen until it formed a clear solution, the temperature was increased to 120° C. and (E)-1-(1-(3-bromophenyl)ethylidene)-2-phenylhydrazine (2.00 g, 6.90 mmol) was added in one portion. The reaction mixture was stirred for 1 h at 120° C., cooled to room temperature, and quenched with crushed ice and water to obtain a white suspension. The solid was filtered, dried on the filter for 15 min, dissolved in $Et_2O$, dried ($Na_2SO_4$) and concentrated to afford 2-(3-bromophenyl)-1H-indole (28, 1.70 g, 6.25 mmol, 90%) as a pale yellow solid: Mp 153-154° C.; IR (ATR) 3430, 1562, 1439, 1420, 1346, 1230, 1073, 1051, 776, 712, 664 cm$^{-1}$; $^1$H NMR (500 MHz, CDCl$_3$) δ 8.26 (bs, 1H), 7.80 (t, J=2.0 Hz, 1H), 7.65 (dd, J=8.0, 0.5 Hz, 1H), 7.57 (ddd, J=7.8, 1.6, 1.0 Hz, 1H), 7.45 (ddd, J=8.0, 1.9, 1.0 Hz, 1H), 7.40 (dd, J=8.0, 0.5 Hz, 1H), 7.30 (t, J=8.0 Hz, 1H), 7.23 (ddd, J=8.1, 7.1, 1.1 Hz, 1H), 7.15 (ddd, J=7.9, 7.1, 0.9 Hz, 1H), 6.84 (dd, J=2.0, 1.0 Hz, 1H); $^{13}$C NMR (125 MHz, CDCl$_3$) δ 137.0, 136.2, 134.4, 130.52, 130.49, 129.1, 128.1, 123.7, 123.2, 122.9, 120.9, 120.5, 111.0, 101.0; HRMS (ESI) m/z calcd for $C_{14}H_{11}NBr$ [M+H]$^+$ 272.0069, found 272.0069.

A suspension of 2-(3-bromophenyl)-1H-indole (28, 5.49 g, 20.2 mmol) in concentrated sulfuric acid (120 mL) at 5° C. was treated dropwise over 30 min with a cold (5° C.) solution of sodium nitrate (1.82 g, 21.4 mmol) in concentrated sulfuric acid (60 mL). The mixture was stirred for 15 min, and then poured onto crushed ice. The yellow precipitate was filtered, dissolved in EtOAc (400 mL), washed with $H_2O$ (3×100 mL), sat. NaHCO$_3$ (2×50 mL) and brine, dried ($Na_2SO_4$), filtered and concentrated. The give crude product (5.53 g) was suspended in MeOH (350 mL), stirred overnight and filtered to afford 2-(3-bromophenyl)-5-nitro-1H-indole (4.18 g, 13.2 mmol, 65%) as a bright yellow solid: $^1$H NMR (300 MHz, DMSO-d$_6$) δ 12.37 (s, 1H), 8.55 (d, J=2.1 Hz, 1H), 8.14 (t, J=1.8 Hz, 1H), 8.03 (dd, J=8.9, 2.3 Hz, 1H), 7.93 (ddd, J=7.8, 1.6, 1.1 Hz, 1H), 7.61-7.56 (m, 2H), 7.47 (t, J=7.8 Hz, 1H), 7.30 (d, J=1.5 Hz, 1H); HRMS (ESI) m/z calcd for $C_{14}H_{10}O_2N_2Br$ [M+H]$^+$ 316.9920, found 316.9918.

A suspension of 2-(3-bromophenyl)-5-nitro-1H-indole (0.15 g, 0.47 mmol), and LiHMDS (0.061 mg, 1.4 mmol) in dry deoxygenated THF (1.5 mL) was treated with 17 (0.20 g, 0.57 mmol). The solution was purged with argon for 20 min and treated with Pd$_2$(dba)$_3$ (0.009 g, 0.01 mmol) and CyJohnPhos (0.013 g, 0.038 mmol). The reaction mixture was heated at 70-75° C. for 24 h in a sealed tube, quenched with sat. NaHCO$_3$ (2 mL) and extracted with EtOAc (3×3 mL). The combined organic layers were washed with brine, dried (Na$_2$SO$_4$) and evaporated. The residue was purified by chromatography on SiO$_2$, (10 to 20% MeOH/CH$_2$Cl$_2$) to give tert-butyl (2-(4-isopropylpiperazin-1-yl)ethyl)(1-(3-(5-nitro-1H-indol-2-yl)phenyl)piperidin-4-yl)carbamate (0.13 g, 0.31 mmol, 45%) as a yellowish foam: $^1$H NMR (400 MHz, CDCl$_3$) δ 9.84 (bs, 1H), 8.54 (d, J=2.0 Hz, 1H), 8.05 (dd, J=8.8, 2.4 Hz, 1H), 7.42 (d, J=8.8 Hz, 1H), 7.30 (t, 7.8 Hz, 1H), 7.20-7.16 (m, 2H), 6.94-6.83 (m, 2H), 4.06 (bs, 1H), 3.80-3.60 (m, 2H), 3.22 (bs, 2H), 2.70-2.44 (m, 14H), 1.82-1.61 (m, 4H), 1.49 (s, 9H), 1.04 (d, J=6.4 Hz, 6H); HRMS (ESI) m/z calcd for $C_{33}H_{47}O_4N_6$ [M+H]$^+$ 591.3653, found 591.3654.

A solution of TFA (0.14 mL, 1.9 mmol) in CH$_2$Cl$_2$ (0.5 mL) was treated with tert-butyl (2-(4-isopropylpiperazin-1-yl)ethyl)(1-(3-(5-nitro-1H-indol-2-yl)phenyl)piperidin-4-yl)carbamate (0.020 g, 0.033 mmol) in CH$_2$Cl$_2$ (0.5 mL) and stirred for 1.5 h. the reaction mixture was concentrated, diluted with sat. NaHCO$_3$, and extracted with EtOAc (3×2 mL). The combined organic layers were washed with brine, dried (Na$_2$SO$_4$), filtered, and evaporated. The residue was purified by chromatography on SiO$_2$, (5 to 10% MeOH/CH$_2$Cl$_2$ with 0.1% Et$_3$N) followed by filtration through a plug of basic Al$_2$O$_3$ (0 to 10% MeOH/CH$_2$Cl$_2$) to give N-(2-(4-isopropylpiperazin-1-yl)ethyl)-1-(3-(5-nitro-1H-indol-2-yl)phenyl)piperidin-4-amine (23, 0.006 g, 0.01 mmol, 36%) as a yellow foam: IR (ATR, neat) 2932, 2823, 2106, 1660, 1601, 1508, 1472, 1465, 1457, 1327, 1294, 1178, 1070, 753 cm$^{-1}$; $^1$H NMR (500 MHz, acetone-d$_6$) δ 8.55 (d, J=2.5 Hz, 1H), 8.03 (dd, J=9.0, 2.5 Hz, 1H), 7.56 (d, 9.0 Hz, 1H), 7.48 (t, J=1.8 Hz, 1H), 7.35-7.29 (m, 2H), 7.16 (d, J=1.0 Hz, 1H), 7.00 (ddd, J=7.8, 2.5, 1.4 Hz, 1H), 3.79-3.75 (m, 2H), 2.90 (td, J=11.9, 2.1 Hz, 2H), 2.78-2.71 (m, 6H), 2.67-2.57 (m, 3H), 2.48-2.41 (m, 10H), 1.99-1.95 (m, 2H), 1.50-1.43 (m, 2H), 0.98 (d, J=6.5 Hz, 6H); $^{13}$C NMR (125 MHz, acetone-d$_6$) δ 152.3, 142.4, 141.8, 140.1, 132.0, 129.7, 128.5, 116.84, 116.77, 116.1, 115.9, 112.8, 111.2, 100.7, 58.2, 54.6, 54.0, 53.7, 48.5, 47.6, 43.5, 32.4, 17.9; HRMS (ESI) m/z calcd for $C_{28}H_{39}O_2N_6$ [M+H]$^+$ 491.3129, found 491.3126.

Synthesis of N-(2-(4-Isopropylpiperazin-1-yl)ethyl)-1-(3-(5-methyl-1H-indol-2-yl)phenyl)piperidin-4-amine (24)

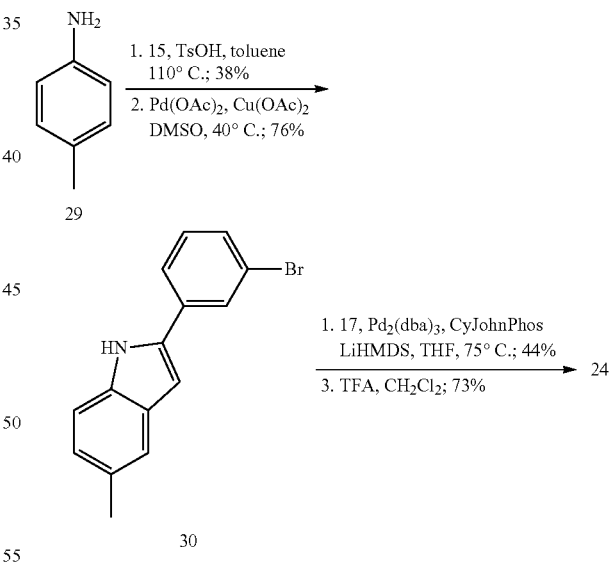

A solution of 3-bromoacetophenone (2.00 g, 10.0 mmol), p-toluidine (1.29 g, 12.1 mmol), and TsOH.H$_2$O (17 mg, 0.10 mmol) in toluene (50 mL) was heated overnight under Dean-Stark conditions. The reaction mixture was cooled to room temperature, concentrated, and purified by chromatography on SiO$_2$ (0 to 5% EtOAc/hexanes) to provide (E)-1-(3-bromophenyl)-N-(p-tolyl)ethan-1-imine as a yellow oil (1.10 g, 3.82 mmol, 38%) that was used without further purification.

A solution of (E)-1-(3-bromophenyl)-N-(p-tolyl)ethan-1-imine (0.246 g, 0.854 mmol), Pd(OAc)$_2$ (18 mg, 0.080 mmol), and Cu(OAc)₂·H₂O (514 mg, 2.57 mmol) in DMSO (3.0 mL) was heated at 90° C. for 5 h, cooled to room temperature, and diluted with EtOAc and H₂O. The layers were separated and the aqueous layer was back-extracted with EtOAc. The combined organic layers were dried (NaSO₄) and concentrated. The residue was absorbed onto SiO₂ and purified by chromatography on SiO₂ (ISCO-Rf, 0 to 20% EtOAc/hexanes) followed by trituration with Et₂O/hexanes (1/1) to give 2-(3-bromophenyl)-5-methyl-1H-indole (30, 0.156 g, 0.545 mmol, 64%) as an off white solid: Mp 189-190° C.; IR (ATR) 3428, 1575, 1450, 1420, 1215, 1077, 798, 767, 667 cm⁻¹; ¹H NMR (500 MHz, CDCl₃) δ 8.20 (bs, 1H), 7.79 (t, J=2.0 Hz, 1H), 7.56 (d, J=7.5 Hz, 1H), 7.43-7.41 (m, 2H), 7.31-7.27 (m, 2H), 7.04 (dd, J=1.0, 8.0 Hz, 1H), 6.75 (d, J=1.0 Hz, 1H), 2.45 (s, 3H); ¹³C NMR (125 MHz, CDCl₃) δ 136.2, 135.3, 134.6, 130.5, 130.3, 129.7, 129.3, 127.9, 124.5, 123.5, 123.1, 120.5, 110.6 (2C), 21.4; HRMS (ESI) m/z calcd for C₁₅H₁₃NBr [M+H]⁺ 286.0226, found 286.0224.

A solution of 2-(3-bromophenyl)-5-methyl-1H-indole (30, 0.143 g, 0.501 mmol), LiHMDS (0.201 g, 1.20 mmol), Pd₂(dba)₃ (9 mg, 0.01 mmol), and CyJohnPhos (14 mg, 0.040 mmol) in anhydrous THF was treated with tert-butyl (2-(4-isopropylpiperazin-1-yl)ethyl)(piperidin-4-yl)carbamate (17, 0.213 g, 0.601 mmol). The reaction mixture was heated at 75° C. overnight, cooled to room temperature, diluted with sat. NaHCO₃, and extracted with CH₂Cl₂ (3×). The combined organic layers were washed with brine, dried (Na₂SO₄), evaporated, and purified by chromatography on SiO₂ (2 to 7% MeOH/CH₂Cl₂) to provide tert-butyl (2-(4-isopropylpiperazin-1-yl)ethyl)(1-(3-(5-methyl-1H-indol-2-yl)phenyl)piperidin-4-yl)carbamate (0.124 g, 0.222 mmol, 44%) as a foam: IR (ATR) 3303, 2963, 2930, 2809, 1685, 1663, 1599, 1465, 1450, 1174, 1146, 1010, 775 cm⁻¹; ¹H NMR (400 MHz, CDCl₃) δ 8.96 (s, 1H), 7.39 (s, 1H), 7.27-7.24 (m, 2H), 7.20 (bs, 1H), 7.13 (d, J=7.2 Hz, 1H), 6.99 (dd, 8.0, 0.8 Hz, 1H), 6.82 (bd, J=7.2 Hz, 1H), 6.70 (s, 1H), 4.10 (bs, 1H), 3.70 (m, 2H), 3.23 (bs, 2H), 2.68-2.44 (m, 16H), 1.72 (bs, 4H), 1.51 (s, 9H), 1.04 (d, J=6.4 Hz, 6H); ¹³C NMR (100 MHz, CDCl₃) δ 155.5, 151.7, 138.6, 135.2, 133.5, 129.6, 129.5, 129.1, 123.6, 120.1, 116.7, 116.0, 113.6, 110.6, 99.2, 79.9, 54.5, 53.8, 49.6, 49.5, 48.6, 39.8, 30.0, 28.5, 21.5, 18.5; HRMS (ESI) m/z calcd for C₃₄H₅₀O₂N₅ [M+H]⁺ 560.3959, found 560.3932.

A solution of TFA (2.35 g, 20.4 mmol) in CH₂Cl₂ (1 mL) was added to a solution of tert-butyl (2-(4-isopropylpiperazin-1-yl)ethyl)(1-(3-(5-methyl-1H-indol-2-yl)phenyl)piperidin-4-yl)carbamate (0.114 g, 0.204 mmol) in CH₂Cl₂ (0.5 mL). The reaction mixture was stirred under an atmosphere of N₂ at room temperature for 1 h, concentrated, diluted with sat. NaHCO₃, and extracted with EtOAc (3×). The combined organic layers were washed with brine, dried (Na₂SO₄), concentrated, and purified by chromatography on SiO₂ (7 to 9% MeOH/CH₂Cl₂ with 0.1% TEA) followed by filtration on basic Al₂O₃ (CH₂Cl₂/MeOH, 100:0 to 100:10) to provide N-(2-(4-isopropylpiperazin-1-yl)ethyl)-1-(3-(5-methy 1-1H-indol-2-yl)phenyl)piperidin-4-amine (24, 68 mg, 0.15 mmol, 73%) as a yellow foam: IR (ATR) 2930, 2924, 2811, 1599, 1457, 1448, 1379, 1344, 1189, 1176, 1144, 1117, 982, 775, 734 cm⁻¹; ¹H NMR (400 MHz, CDCl₃) δ 8.52 (s, 1H), 7.39 (d, J=0.7 Hz, 1H), 7.30-7.26 (m, 2H), 7.21 (t, J=1.9 Hz, 1H), 7.10 (ddd, J=7.6, 1.4, 0.8 Hz, 1H), 7.01-6.98 (ddd, J=8.0, 1.6, 0.4 Hz, 1H), 6.88 (dd, J=8.0, 2.1 Hz, 1H), 6.70 (dd, J=2.1, 0.8 Hz, 1H), 3.73 (app d, J=12.6 Hz, 2H), 2.86-2.76 (m, 4H), 2.68-2.48 (m, 12H), 2.44 (s, 3H), 2.00 (dd, J=12.6, 2.2 Hz, 2H), 1.53 (dq, J=11.5, 3.0 Hz, 2H), 1.05 (d, J=6.5 Hz, 6H); ¹³C NMR (100 MHz, CDCl₃) δ 152.1, 138.8, 135.2, 133.5, 129.7, 129.6, 129.3, 123.8, 120.3, 116.4, 115.9, 113.5, 110.6, 99.4, 58.1, 55.2, 54.6, 53.6, 48.8, 48.7, 43.5, 32.7, 21.6, 18.8; HRMS (ESI) m/z calcd for C₂₉H₄₂N₅ [M+H]⁺ 460.3435, found 460.3434.

Synthesis of N-(2-(4-Isopropylpiperazin-1-yl)ethyl)-1-(3-(5-methoxy-1H-indol-2-yl)phenyl)piperidin-4-amine (25)

Scheme 7.

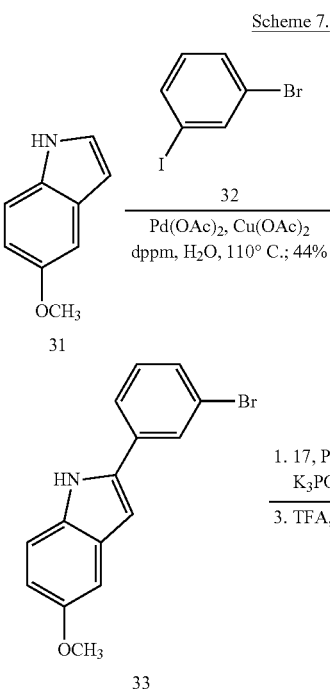

A solution of 3-bromoiodobenzene (32, 0.283 g, 1.00 mmol), 5-methoxyindole (31, 0.147 g, 1.00 mmol), Pd(OAc)₂ (12 mg, 0.050 mmol), bis(diphenylphosphino)methane (20 mg, 0.05 mmol), and KOAc (0.297 g, 3.00 mmol) in deoxygenated water (2 mL) was heated at 110° C. for 24 h, cooled to room temperature, diluted with ethyl acetate (10 mL) and 1 N HCl (5 mL), and extracted with ethyl acetate (2×10 mL). The combined organic layers were dried (MgSO₄), evaporated, and purified by chromatography on SiO₂ (10% EtOAc/hexanes) followed by recrystallization from hexanes and CH₂Cl₂ to give 2-(3-bromophenyl)-5-methoxy-1H-indole (33, 0.133 g, 0.440 mmol, 44%) as a white solid: ¹H NMR (300 MHz, CDCl₃) δ 8.20 (bs, 1H), 7.77 (s, 1H), 7.55 (app d, J=7.7 Hz, 1H), 7.43 (app d, J=8.1 Hz, 1H), 7.30 (m, 2H), 7.08 (d, J=2.3 Hz, 1H), 6.88 (dd, J=8.8, 2.4 Hz, 1H), 6.76 (d, J=1.5 Hz, 1H), 3.87 (s, 3H); HRMS (ESI) m/z calcd for C₁₅H₁₃ONBr [M+H]⁺ 302.0175, found 302.0174.

A solution of 33 (76 mg, 0.25 mmol), K₃PO₄ (82 mg, 0.38 mmol), Pd₂(dba)₃ (5 mg, 0.005 mmol), CyJohnPhos (7 mg, 0.02 mmol) in anhydrous and deoxygenated dioxane (1 mL) in a 2-5 mL conical sealed vessel was degassed by bubbling argon for 5 min. The reaction mixture was treated with tert-butyl (2-(4-isopropylpiperazin-1-yl)ethyl)(piperidin-4-yl)carbamate (17, 0.106 g, 0.300 mmol) in dry dioxane (1.5 mL) and degassed for 15 min. The vessel was sealed and heated at 110° C. for 11 h in a Biotage Initiator microwave reactor, cooled to room temperature, diluted with sat.

NaHCO$_3$, and extracted with CH$_2$Cl$_2$ (3×). The combined organic layers were washed with brine, dried (Na$_2$SO$_4$), evaporated, and purified by chromatography on SiO$_2$ (2% MeOH/CH$_2$Cl$_2$ and 0.1% TEA) followed by chromatography on basic Al$_2$O$_3$ (CH$_2$Cl$_2$) to give tert-butyl (2-(4-isopropylpiperazin-1-yl)ethyl)(1-(3-(5-methoxy-1H-indol-2-yl)phenyl)piperidin-4-yl)carbamate (46 mg, 0.080 mmol, 32%) as a yellow oil: $^1$H NMR (400 MHz, CDCl$_3$) δ 8.76 (s, 1H), 7.28-7.25 (m, 2H), 7.18 (br s, 1H), 7.12 (d, J=7.6 Hz, 1H), 7.07 (d, J=2.2 Hz, 1H), 6.85-6.81 (m, 2H), 6.71 (d, J=1.2 Hz, 1H), 4.11 (br s, 1H), 3.85 (s, 3H), 3.74-3.72 (m, 2H), 3.29-3.19 (m, 2H), 2.71-2.45 (m, 13H), 1.76-1.72 (m, 3H), 1.48 (s, 9H), 1.05 (d, J=6.5 Hz, 6H); $^{13}$C NMR (100 MHz, CDCl$_3$) δ 155.5, 154.4, 151.8, 139.3, 133.5, 132.1, 129.7, 116.7, 116.1, 113.6, 112.4, 111.8, 102.2, 99.6, 80.0, 55.9, 49.6, 48.6, 30.11, 30.09, 28.6, 18.6.

A solution of TFA (0.599 mL, 7.99 mmol) and triethylsilane (0.129 mL, 0.799 mmol) in CH$_2$Cl$_2$ (1 mL) was added to a solution of tert-butyl (2-(4-isopropylpiperazin-1-yl)ethyl)(1-(3-(5-methoxy-1H-indol-2-yl)phenyl)piperidin-4-yl)carbamate (46 mg, 0.080 mmol) in CH$_2$Cl$_2$ (0.5 mL). The reaction mixture was stirred under an atmosphere of N$_2$ at room temperature for 2 h, evaporated, diluted with sat. NaHCO$_3$, and extracted with EtOAc (3×). The combined organic layers were washed with brine, dried (Na$_2$SO$_4$), evaporated, and purified by chromatography on SiO$_2$ (7 to 9% MeOH/CH$_2$Cl$_2$ with 0.1% TEA) followed by chromatography on basic Al$_2$O$_3$ (0 to 9% MeOH/CH$_2$Cl$_2$) to give N-(2-(4-isopropylpiperazin-1-yl)ethyl)-1-(3-(5-methoxy-1H-indol-2-yl)phenyl)piperidin-4-amine (25, 20 mg, 0.041 mmol, 51%) as a yellow oil: IR (ATR) 3221, 2924, 2818, 1577, 1452, 1881, 1381, 1204, 1176, 1146, 1114, 839, 775 cm$^{-1}$; $^1$H NMR (400 MHz, CDCl$_3$) δ 8.74 (bs, 1H), 7.29 (m, 2H), 7.21 (app t, J=1.9 Hz, 1H), 7.11 (app d, J=7.8 Hz, 1H), 7.07 (d, J=2.3 Hz, 1H), 6.87 (dd, J=8.1, 2.1 Hz, 1H), 6.83 (dd, J=8.8, 2.4 Hz, 1H), 6.71 (app d, J=1.0 Hz, 1H), 4.01 (bs, 2H), 3.85 (s, 3H), 3.72 (app d, J=12.6 Hz, 2H), 2.84-2.51 (m, 16H), 2.00 (m, 3H), 1.56 (qd, J=11.6, 3.0 Hz, 2H), 1.06 (d, J=6.5 Hz, 6H); $^{13}$C NMR (100 MHz, CDCl$_3$) δ 154.5, 152.0, 139.5, 133.5, 132.2, 129.8, 116.6, 116.0, 113.5, 112.4, 111.8, 102.3, 99.7, 57.4, 56.0, 55.0, 54.7, 53.1, 48.67, 48.54, 43.0, 32.1, 18.5; HRMS (ESI) m/z calcd for C$_{29}$H$_{42}$ON$_5$ [M+H]$^+$ 476.3384, found 476.3383.

Synthesis of N-(2-(4-Isopropylpiperazin-1-yl)ethyl)-1-(3-(5-(trifluoromethoxy)-1H-indol-2-yl)phenyl)piperidin-4-amine (26)

Scheme 8.

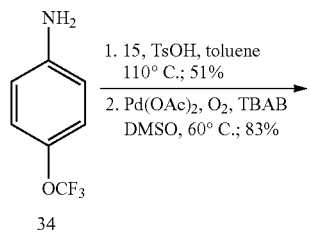

34

1. 15, TsOH, toluene 110° C.; 51%
2. Pd(OAc)$_2$, O$_2$, TBAB DMSO, 60° C.; 83%

-continued

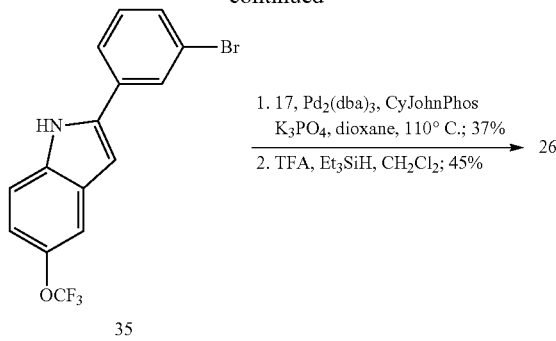

35

1. 17, Pd$_2$(dba)$_3$, CyJohnPhos K$_3$PO$_4$, dioxane, 110° C.; 37%
2. TFA, Et$_3$SiH, CH$_2$Cl$_2$; 45%

→ 26

A solution of 3-bromoacetophenone (15, 1.00 g, 5.02 mmol), 4-(trifluoromethoxy)aniline (1.07 g, 6.04 mmol), and TsOH.H$_2$O (8.7 mg, 0.046 mmol) in toluene (50 mL) was heated under Dean-Stark conditions overnight. The reaction mixture was cooled to room temperature, concentrated, and purified by chromatography on SiO$_2$ (0 to 5% EtOAc/hexanes) to give (E)-1-(3-bromophenyl)-N-(4-(trifluoromethoxy)phenyl)ethan-1-imine as a yellow oil (0.91 g, 2.5 mmol, 51%): $^1$H NMR (400 MHz, CDCl$_3$) δ 8.14 (s, 1H), 7.88-7.86 (m, 1H), 7.62-7.59 (m, 1H), 7.32 (td, J=7.6, 0.4 Hz, 1H), 7.21 (app d, J=8.8 Hz, 2H), 6.81-6.77 (m, 2H), 2.22 (s, 3H).

A solution of (E)-1-(3-bromophenyl)-N-(4-(trifluoromethoxy)phenyl)ethan-1-imine (75 mg, 0.21 mmol), Pd(OAc)$_2$ (5 mg, 0.02 mmol), and TBAB (0.13 g, 0.40 mmol) in DMSO (1 mL) in a Schlenk tube was purged, filled with oxygen and heated at 60° C. for 24 h. The reaction mixture was cooled to room temperature, diluted with ethyl acetate (5 mL), and filtered through SiO$_2$. The filtrate was washed with 1 M NaHSO$_3$, concentrated and purified by chromatography on SiO$_2$ (30% CH$_2$Cl$_2$/hexanes) to give 2-(3-bromophenyl)-5-(trifluoromethoxy)-1H-indole (35, 62 mg, 0.17 mmol, 83%): $^1$H NMR (400 MHz, CDCl$_3$) δ 8.36 (bs, 1H), 7.78 (s, 1H), 7.55 (d, J=7.6 Hz, 1H), 7.48-7.46 (m, 2H), 7.35 (d, J=8.8 Hz, 1H), 7.31 (app t, J=8.0 Hz, 1H), 7.09 (d, J=8.8 Hz, 1H), 6.81 (s, 1H); $^{13}$C NMR (100 MHz, CDCl$_3$) δ 143.7, 138.2, 135.3, 134.0, 131.1, 130.7, 129.3, 128.3, 123.9, 123.4, 120.9 (q, J$_{CF}$=255.3 Hz), 116.9, 113.3, 111.7, 101.3; HRMS (ESI) m/z calcd for C$_{15}$H$_{10}$ONBrF$_3$ [M+H]$^+$ 355.9892, found 355.9891.

A solution of 35 (89.1 mg, 0.250 mmol), K$_3$PO$_4$ (82 mg, 0.39 mmol), Pd$_2$(dba)$_3$ (4.70 mg, 0.005 mmol), and CyJohnPhos (7.20 mg, 0.020 mmol) in anhydrous and deoxygenated dioxane (1 mL) in a 2-5 mL conical sealed vial was degassed by bubbling argon for 5 min. The reaction mixture was treated with a solution of tert-butyl (2-(4-isopropylpiperazin-1-yl)ethyl)(piperidin-4-yl)carbamate (17, 0.106 g, 0.299 mmol) in dry dioxane (1.5 mL) and degassed for 15 min. The vial was sealed and heated at 110° C. for 11 h in a Biotage Initiator microwave reactor, cooled to room temperature, diluted with sat. NaHCO$_3$, and extracted with CH$_2$Cl$_2$ (3×). The organic layers were combined, washed with brine, dried (Na$_2$SO$_4$), evaporated, and purified by chromatography on SiO$_2$ (2% MeOH/CH$_2$Cl$_2$ with 0.1% TEA) followed by chromatography on basic Al$_2$O$_3$ (CH$_2$Cl$_2$) to give tert-butyl (2-(4-isopropylpiperazin-1-yl)ethyl)(1-(3-(5-(trifluoromethoxy)-1H-indol-2-yl)phenyl)piperidin-4-yl)carbamate (46 mg, 0.073 mmol, 29%) as a light yellow oil: IR (ATR) 3266, 2969, 2961, 2952, 2933, 2928, 2818, 2810, 1681, 1664, 1601, 1478, 1465, 1450, 1413, 1383, 1366, 1346, 1329, 1301, 1253, 1217, 1152, 1010, 1003, 995, 973, 895, 867 cm$^{-1}$; $^1$H NMR (400 MHz, acetone-d$_6$) δ 10.47 (s, 1H), 6.97-6.93 (m, 3H), 6.80-6.76 (m, 2H), 6.52 (d, J=8.8 Hz, 1H), 6.45-6.43 (m, 2H), 3.40 (d, J=12.0 Hz, 2H), 2.72 (bs, 2H), 2.48 (bs, 2H), 2.29 (app t, J=11.6 Hz, 2H), 1.93-1.89 (m, 9H), 1.52 (app s, 1H), 1.42 (bs, 2H), 1.24 (bs, 2H), 0.93 (s, 9H), 0.43 (d, J=6.4 Hz, 6H); $^{13}$C NMR (100 MHz, acetone-d$_6$) δ 155.6, 152.8, 143.7, 141.9, 136.6, 133.6, 130.5, 130.3, 129.1, 128.4, 121.8 (q, J$_{CF}$=253.2 Hz), 117.0, 116.7, 116.0, 113.8, 113.1, 112.8, 100.1, 79.5, 54.9, 54.8, 50.0, 49.3, 28.7, 18.7; HRMS [ESI] m/z calcd for C$_{34}$H$_{47}$O$_3$N$_5$F$_3$ [M+H]$^+$ 630.3626, found 630.3628.

A solution of TFA (0.50 mL) and triethylsilane (0.10 mL, 0.64 mmol) in CH$_2$Cl$_2$ (1 mL) was added to a solution of tert-butyl (2-(4-isopropylpiperazin-1-yl)ethyl)(1-(3-(5-(trifluoromethoxy)-1H-indol-2-yl)phenyl)piperidin-4-yl)carbamate (40 mg, 0.064 mmol) in CH$_2$Cl$_2$ (0.5 mL). The reaction mixture was stirred under an atmosphere of N$_2$ at room temperature for 1 h, concentrated, diluted with sat. NaHCO$_3$, and extracted with EtOAc (3×). The combined organic layers were washed with brine, dried (Na$_2$SO$_4$), concentrated, and purified by chromatography on SiO$_2$ (7 to 9% MeOH/CH$_2$Cl$_2$ with 0.1% TEA) followed by chromatography on basic Al$_2$O$_3$ (0 to 9% MeOH/CH$_2$Cl$_2$) to give N-(2-(4-isopropylpiperazin-1-yl)ethyl)-1-(3-(5-(trifluoromethoxy)-1H-indol-2-yl)phenyl)piperidin-4-amine (26, 15 mg, 0.028 mmol, 45%) as a light yellow foam: IR(ATR) 2975, 2818, 1670, 1458, 1254, 1199, 1174, 1130, 829, 800, 783, 719 cm$^{-1}$; $^1$H NMR (400 MHz, CDCl$_3$) δ 9.02 (s, 1H), 7.45 (d, J=1.2 Hz, 1H), 7.36 (d, J=8.8 Hz, 1H), 7.30 (app t, J=7.6 Hz, 1H), 7.24 (app t, J=1.6 Hz, 1H), 7.14-7.11 (m, 1H), 7.03 (ddd, J=8.8, 2.4, 0.8 Hz, 1H), 6.90 (ddd, J=8.4, 2.4, 0.8 Hz, 1H), 6.77 (app d, J=1.2 Hz, 1H), 3.74 (app d, J=12.8 Hz, 2H), 2.86-2.52 (m, 16H), 2.01 (dd, J=12.7, 2.3 Hz, 2H), 1.59 (qd, J=12.8, 4.0 Hz, 2H), 1.08 (d, J=6.4 Hz, 6H); $^{13}$C NMR (100 MHz, CDCl$_3$) δ 152.0, 143.4, 140.7, 135.2, 133.0, 129.9, 129.5, 121.0 (q, J$_{CF}$=255.2 Hz), 116.7, 116.4, 116.1, 113.7, 112.9, 111.6, 100.1, 57.1, 55.2, 55.0, 52.9, 48.5, 43.0, 31.9, 18.4; HRMS [ESI] m/z calcd for C$_{29}$H$_{39}$ON$_5$F$_3$ [M+H]$^+$ 530.3101, found 530.3100.

Biological Assays

To optimize p97 inhibitors, the C-5 trifluoromethylated trifluoromethylated indole 12 was generated as a promising lead structure. In the ADP-Glo assay, it was determined that this compound exhibits a 5.96±1.66 μM IC$_{50}$ value (Table 1), after which the effect of replacing the CF$_3$— with an SF$_5$-group at the C-5 position as shown for compound 13 was explored. The ADP-Glo assay can be conducted as described in Chou, T.-F.; Bulfer, S. L.; Weihl, C. C.; Li, K.; Lis, L. G.; Walters, M. A.; Schoenen, F. J.; Lin, H. J.; Deshaies, R. J.; Arkin, M. R., "Specific inhibition of p97/VCP atpase and kinetic analysis demonstrate interaction between D1 and D2 ATPase domains." J. Mol. Biol. 2014, 426, 2886-2899.

Figure 3:
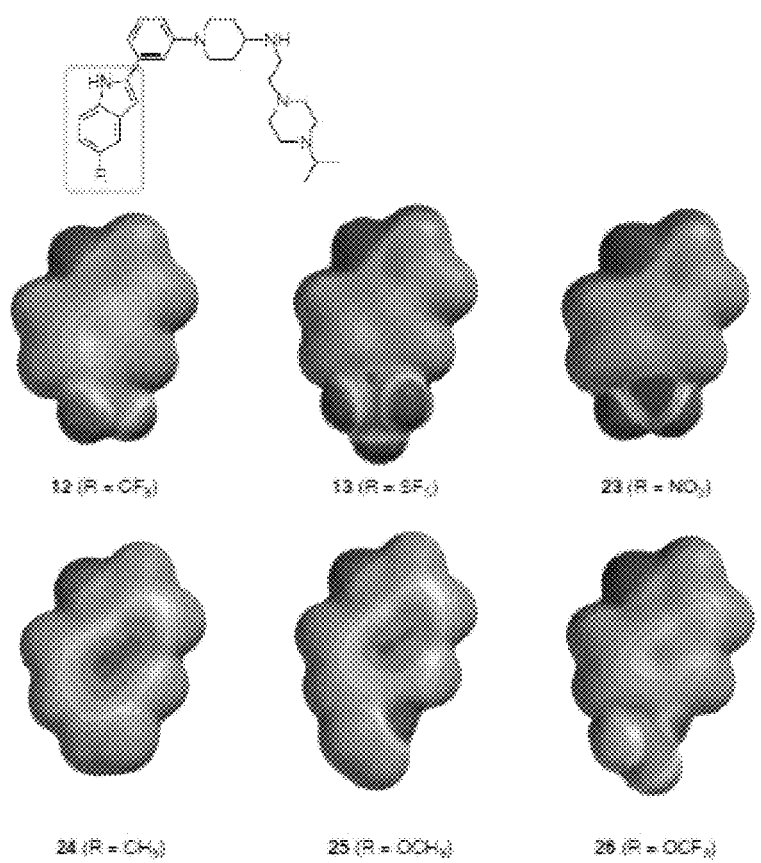
FIG. 3 shows the structures and steric/electronic features of compounds of the present disclosure.

Surprisingly, replacement of the trifluoromethyl with a pentafluorosulfanyl group reduced the p97 inhibition almost 4-fold to an IC$_{50}$ of 21.48±0.49 μM. It was hypothesized that this decrease could either be due to the larger size of the SF$_5$ group or its stronger electron-withdrawing effect on the indole ring. Accordingly, the corresponding nitro (23), methyl (24), methoxy (25), and trifluoromethoxy (26) analogs were prepared to test these parameters. Electron-density surfaces encoded with electrostatic potential maps for the indole segments of these compounds illustrate both their steric features as well as the range of their inductive effects on the aromatic π-system (FIG. 3). Sterically, SF$_5$-analog 13 and CF$_3$O-analog 26 are the closest match, but their electronic effects on the indole ring and the indole nitrogen are significantly different. As expected, nitro-analog 23 is the best electronic match of the pentafluorosulfanyl derivative. Sterically, and, in particular, electronically, CH$_3$O-analog 25 is most closely related to CH$_3$-analog 24. Arguably, CF$_3$-analog 12 is somewhat unique in this series, but sterically its closest match would be NO$_2$-analog 23 and CH$_3$-analog 24, whereas electronically it is situated between SF$_5$-analog 13 and CF$_3$O-analog 26. Accordingly, it was expected that the methylated indole 24 would have similar activity to 12 if steric effects were dominant, whereas electronic effects would likely favor ethers 25 and 26, since the bulkier and more electron-deficient pentafluorosulfanyl had registered a significant drop in activity.

Evaluation of 23-26 in the p97 ADP-Glo assay revealed a remarkable three orders of magnitude range of activities between the six indoles (Table 2). Nitro-analog 23 was found to be a 40 nM inhibitor of the AAA ATPase (Entry 3, IC$_{50}$ 0.04±0.04 μM). CF$_3$O-analog 26 was considerably less active (Entry 6, IC$_{50}$ 3.72±0.77 μM), but showed higher activity than CF$_3$-analog 12. Methylated 24 and methoxylated 25 had intermediate but still sub-micromolar IC$_{50}$'s (Entries 4 and 5, IC$_{50}$ 0.20±0.12 μM and 0.66±0.20 μM, respectively).

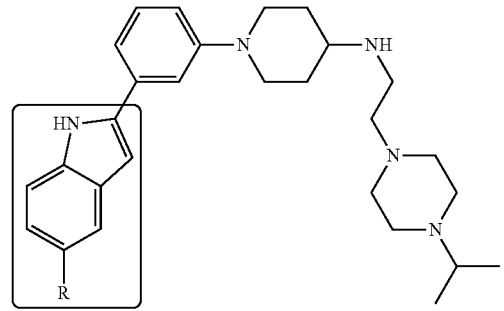

TABLE 2

Biochemical Activities of p97 Inhibitors[a]

| Entry | Compound/R-Group | p97-ADPGlo IC$_{50}$ [μM] | p97-ADPGlo Std. Dev. [μM] |
|---|---|---|---|
| 1 | 12/CF$_3$ | 4.7 | ±2.0 |
| 2 | 13/SF$_5$ | 21.5 | ±0.4 |
| 3 | 23/NO$_2$ | 0.05 | ±0.04 |
| 4 | 24/CH$_3$ | 0.24 | ±0.11 |
| 5 | 25/OCH$_3$ | 0.71 | ±0.22 |
| 6 | 26/OCF$_3$ | 3.8 | ±0.8 |

[a]Assay conditions: ADP Glo with p97 ATPase WT in the presence of 100 μM. ATP. Assays were run in quadruplicate (12, 13, 25, 26), seven times (24), or nine times (23).

TABLE 3
| Biochemical Activities of p97 Inhibitors | |
|---|---|
| Structure | ADPGlo IC$_{50}$ (μM) |
| 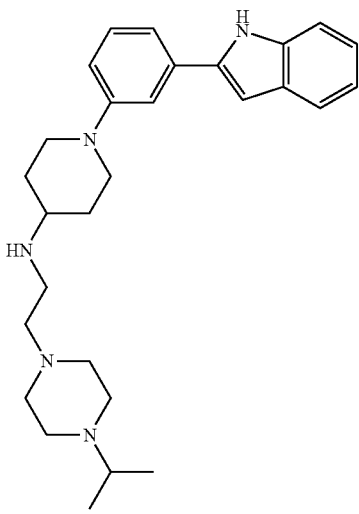 [SMILES: CC(C)N1CCN(CCNC2CCN(c3cccc(-c4cc5ccccc5[nH]4)c3)CC2)CC1] | 0.1 |
| 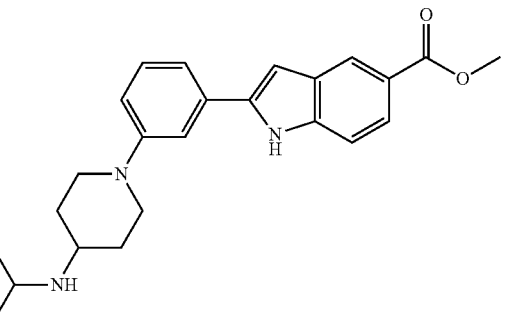 | 0.51 |
| 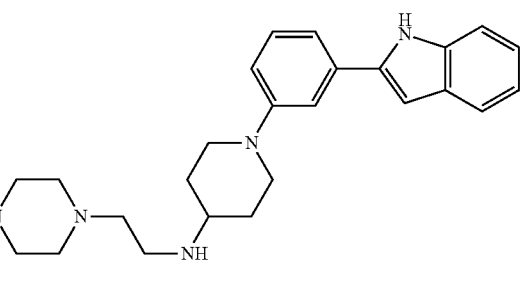 | 0.3 |

TABLE 3-continued
Biochemical Activities of p97 Inhibitors
| Structure | ADPGlo IC$_{50}$ (µM) |
|---|---|
| 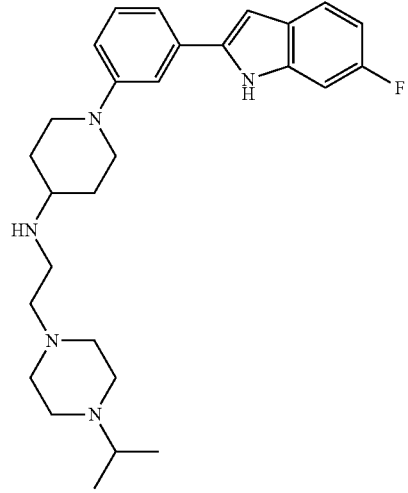 [SMILES: CC(C)N1CCN(CCNC2CCN(c3cccc(-c4cc5ccc(F)cc5[nH]4)c3)CC2)CC1] | 0.54 |
| 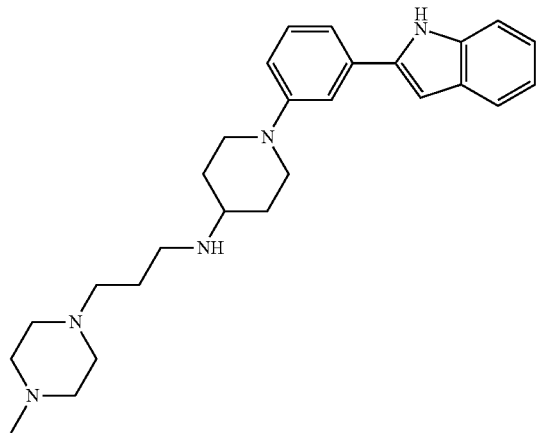 [SMILES: CN1CCN(CCCNC2CCN(c3cccc(-c4cc5ccccc5[nH]4)c3)CC2)CC1] | 0.21 |
| 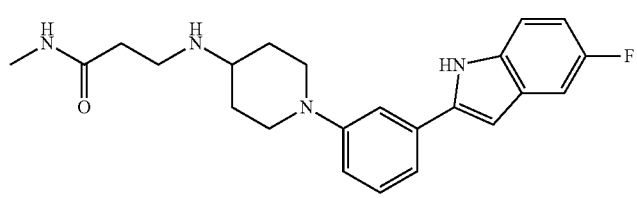 | 0.63 |

TABLE 3-continued
| Biochemical Activities of p97 Inhibitors | |
|---|---|
| Structure | ADPGlo IC$_{50}$ (μM) |
| 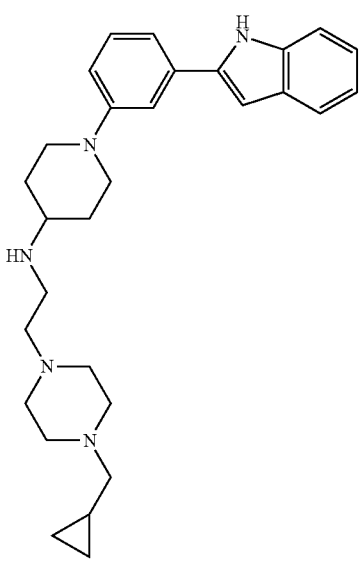 [SMILES: c1cc(-c2cc3ccccc3[nH]2)cc(N2CCC(NCCN3CCN(CC4CC4)CC3)CC2)c1] | 0.17 |
| 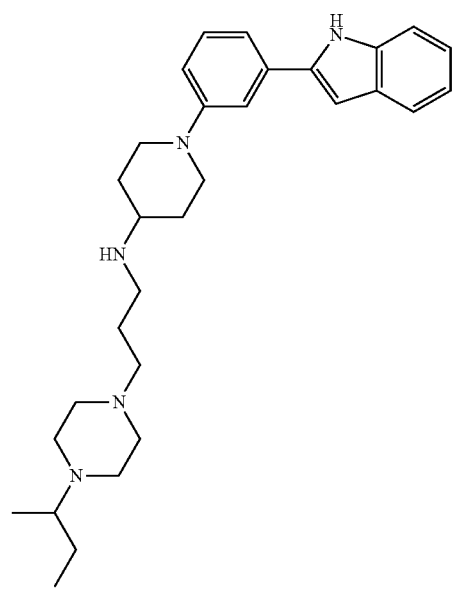 [SMILES: CCC(C)N1CCN(CCCNC2CCN(c3cccc(-c4cc5ccccc5[nH]4)c3)CC2)CC1] | 0.64 |

TABLE 3-continued

Biochemical Activities of p97 Inhibitors

| Structure | ADPGlo IC$_{50}$ (μM) |
|---|---|
| (structure) | 0.14 |
| (structure) | 0.66 |
| (structure) | 0.38 |
| (structure) | 0.67 |

TABLE 3-continued

| Biochemical Activities of p97 Inhibitors | |
|---|---|
| Structure | ADPGlo IC$_{50}$ (μM) |
| *[structure: 3-(1H-indol-2-yl)phenyl-piperidine-4-amine linked via ethyl to 4-methylpiperazine]* | 0.38 |
| *[structure: 3-(5-fluoro-1H-indol-2-yl)phenyl-piperidine-4-amine linked via CH$_2$ to 3-azidophenyl]* | 0.68 |
| *[structure: 3-(1H-indol-2-yl)phenyl-piperidine-4-amine linked via ethyl to 4-ethylpiperazine]* | 0.19 |

TABLE 3-continued
| Biochemical Activities of p97 Inhibitors | |
|---|---|
| Structure | ADPGlo IC$_{50}$ (μM) |
| 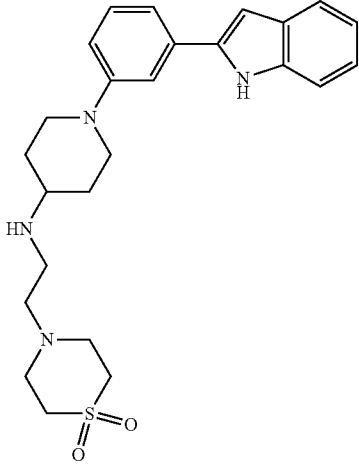 [SMILES: O=S1(=O)CCN(CCNC2CCN(c3cccc(-c4cc5ccccc5[nH]4)c3)CC2)CC1] | 0.7 |
| 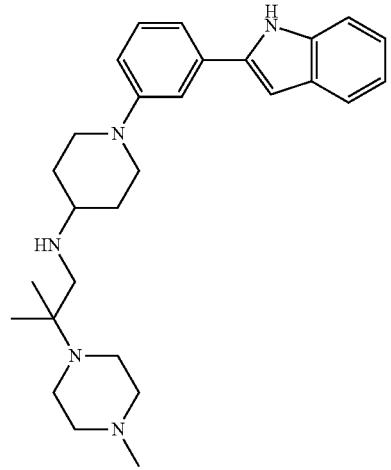 [SMILES: CN1CCN(C(C)(C)CNC2CCN(c3cccc(-c4cc5ccccc5[nH]4)c3)CC2)CC1] | 0.45 |
| 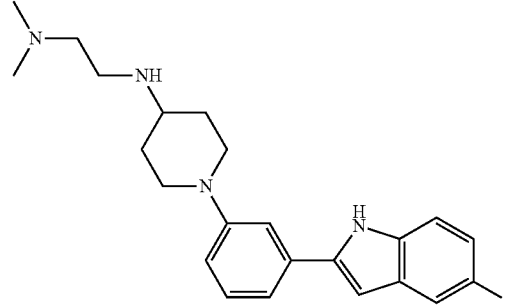 | 0.71 |

TABLE 3-continued

Biochemical Activities of p97 Inhibitors

| Structure | ADPGlo IC$_{50}$ (μM) |
|---|---|
| (structure) | 0.3 |
| (structure) | 0.76 |
| (structure) | 0.8 |

TABLE 3-continued

Biochemical Activities of p97 Inhibitors

| Structure | ADPGlo IC$_{50}$ (μM) |
|---|---|
| (structure) | 0.8 |
| (structure) | 0.81 |
| (structure) | 0.85 |

TABLE 3-continued
Biochemical Activities of p97 Inhibitors
| Structure | ADPGlo IC$_{50}$ (μM) |
|---|---|
| 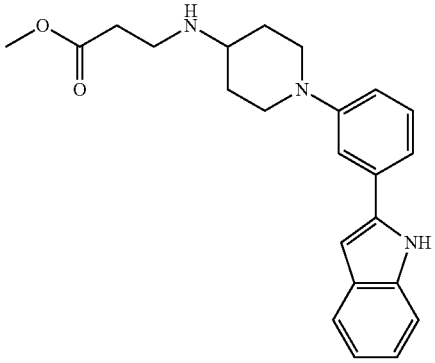 [SMILES: COC(=O)CCNC1CCN(c2cccc(-c3cc4ccccc4[nH]3)c2)CC1] | 1 |
| 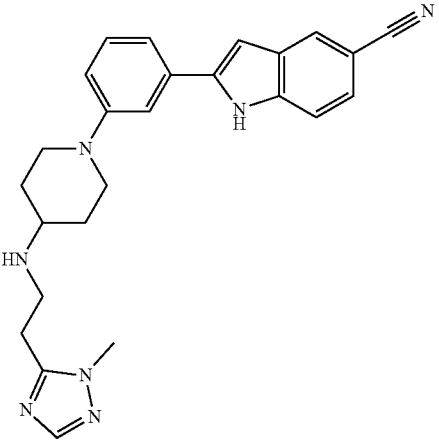 [SMILES: Cn1ncnc1CCNC1CCN(c2cccc(-c3cc4cc(C#N)ccc4[nH]3)c2)CC1] | 0.89 |
| 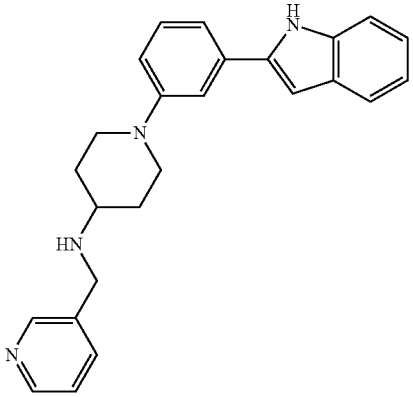 [SMILES: c1cncc(CNC2CCN(c3cccc(-c4cc5ccccc5[nH]4)c3)CC2)c1] | 0.74 |

TABLE 3-continued

Biochemical Activities of p97 Inhibitors

| Structure | ADPGlo IC$_{50}$ (μM) |
|---|---|
| (structure) | 0.96 |
| (structure) | 0.72 |
| (structure) | 1.1 |
| (structure) | 0.57 |

TABLE 3-continued
Biochemical Activities of p97 Inhibitors
| Structure | ADPGlo IC$_{50}$ (μM) |
|---|---|
| 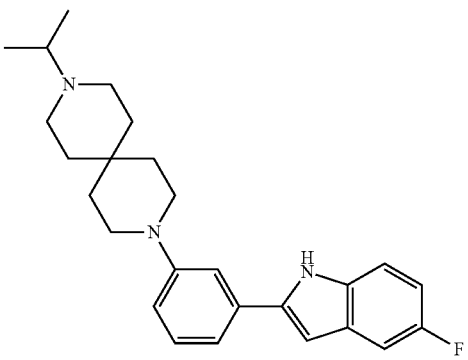 [SMILES: CC(C)N1CCC2(CCN(c3cccc(-c4cc5cc(F)ccc5[nH]4)c3)CC2)CC1] | 1.1 |
| 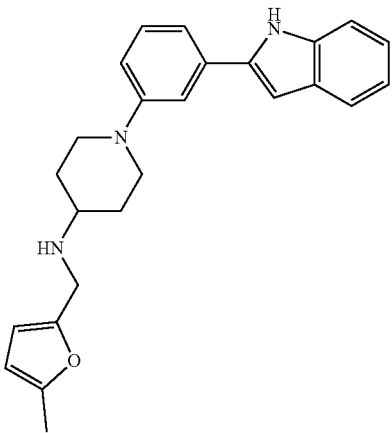 [SMILES: Cc1ccc(CNC2CCN(c3cccc(-c4cc5ccccc5[nH]4)c3)CC2)o1] | 0.89 |
| 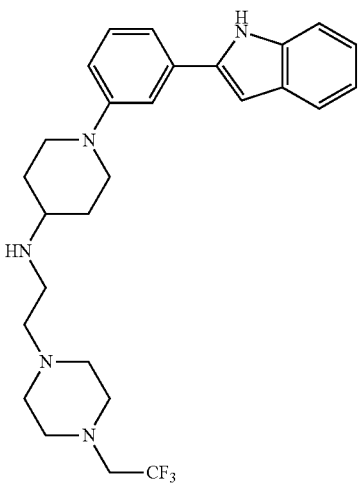 [SMILES: FC(F)(F)CN1CCN(CCNC2CCN(c3cccc(-c4cc5ccccc5[nH]4)c3)CC2)CC1] | 1.3 |

TABLE 3-continued
| Biochemical Activities of p97 Inhibitors | |
|---|---|
| Structure | ADPGlo IC$_{50}$ (μM) |
| 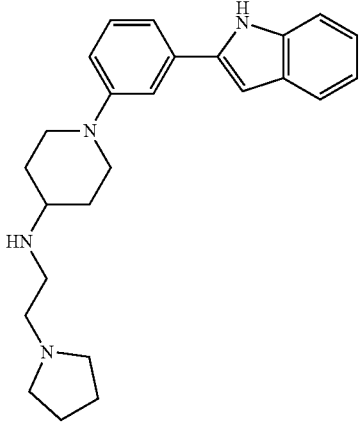 [SMILES: c1cc(-c2cc3ccccc3[nH]2)cc(N2CCC(NCCN3CCCC3)CC2)c1] | 0.88 |
| 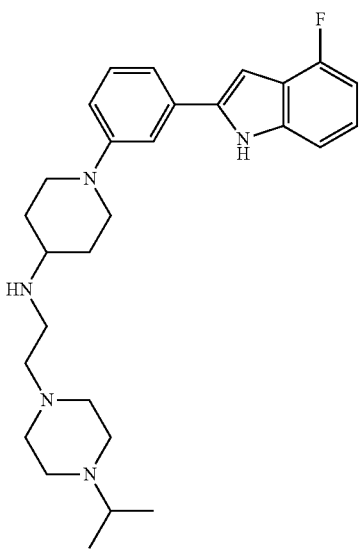 [SMILES: CC(C)N1CCN(CCNC2CCN(c3cccc(-c4cc5c(F)cccc5[nH]4)c3)CC2)CC1] | 1.3 |
| 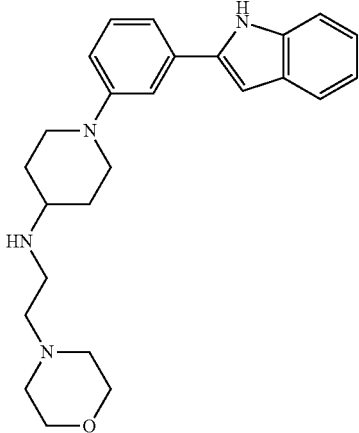 [SMILES: c1cc(-c2cc3ccccc3[nH]2)cc(N2CCC(NCCN3CCOCC3)CC2)c1] | 0.91 |

TABLE 3-continued

Biochemical Activities of p97 Inhibitors

| Structure | ADPGlo IC$_{50}$ (μM) |
|---|---|
| *[structure]* | 1.3 |
| *[structure]* | 1 |
| *[structure]* | 1.3 |
| *[structure]* | 1.7 |

TABLE 3-continued

Biochemical Activities of p97 Inhibitors

| Structure | ADPGlo IC$_{50}$ (μM) |
|---|---|
| (structure) | 1.3 |
| (structure) | 1.4 |
| (structure) | 1.4 |
| (structure) | 2.7 |

TABLE 3-continued
Biochemical Activities of p97 Inhibitors
| Structure | ADPGlo IC$_{50}$ (μM) |
|---|---|
| 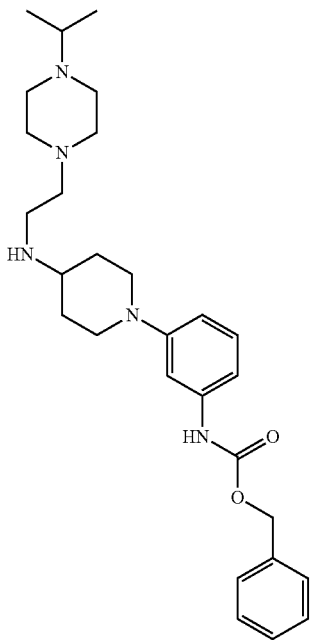 [SMILES: CC(C)N1CCN(CCNC2CCN(c3cccc(NC(=O)OCc4ccccc4)c3)CC2)CC1] | 1.7 |
| 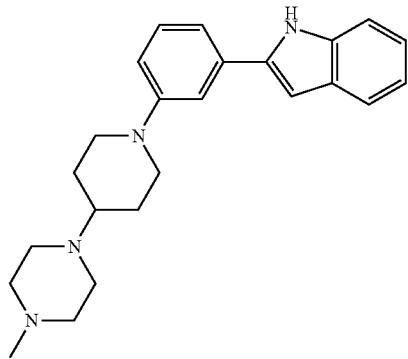 [SMILES: CN1CCN(C2CCN(c3cccc(-c4cc5ccccc5[nH]4)c3)CC2)CC1] | 13 |
| 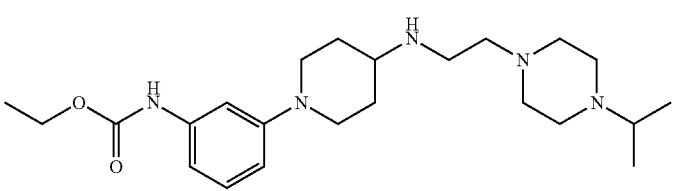 [SMILES: CCOC(=O)Nc1cccc(N2CCC(NCCN3CCN(C(C)C)CC3)CC2)c1] | 1.7 |

TABLE 3-continued

Biochemical Activities of p97 Inhibitors

| Structure | ADPGlo IC$_{50}$ (μM) |
|---|---|
| | 0.015 |
| 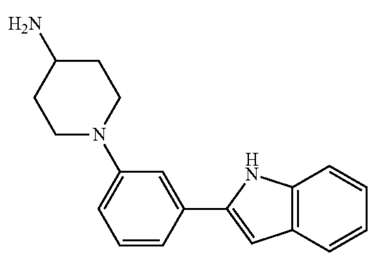 [SMILES: NC1CCN(c2cccc(-c3cc4ccccc4[nH]3)c2)CC1] | 1.8 |
| | 0.015 |

TABLE 3-continued

Biochemical Activities of p97 Inhibitors

| Structure | ADPGlo IC$_{50}$ (μM) |
|---|---|
| (structure) | 1.9 |
| (structure) | 0.025 |
| (structure) | 2.2 |

TABLE 3-continued
Biochemical Activities of p97 Inhibitors
| Structure | ADPGlo IC$_{50}$ (μM) |
|---|---|
| 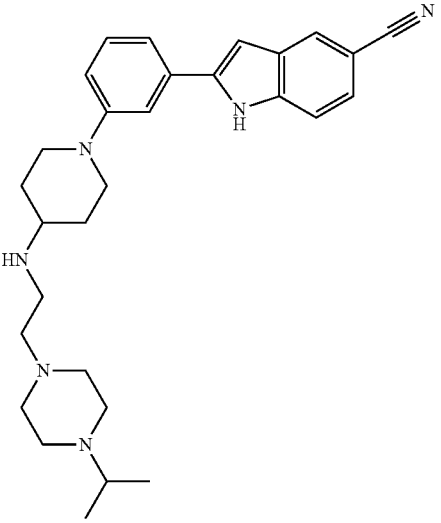 [SMILES: CC(C)N1CCN(CCNC2CCN(c3cccc(-c4cc5cc(C#N)ccc5[nH]4)c3)CC2)CC1] | 0.026 |
| 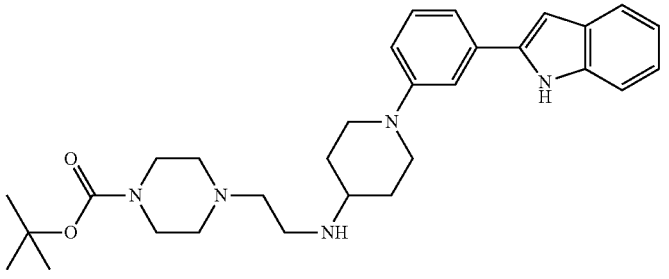 [SMILES: CC(C)(C)OC(=O)N1CCN(CCNC2CCN(c3cccc(-c4cc5ccccc5[nH]4)c3)CC2)CC1] | 2.4 |
| 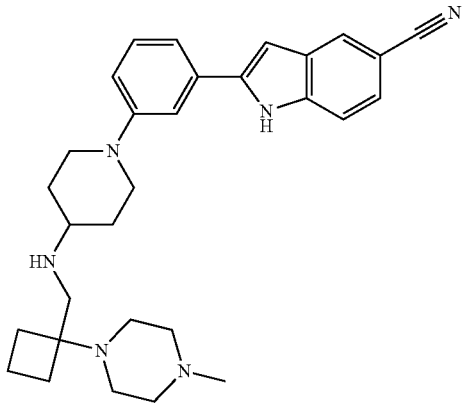 [SMILES: CN1CCN(C2(CNC3CCN(c4cccc(-c5cc6cc(C#N)ccc6[nH]5)c4)CC3)CCC2)CC1] | 0.026 |

TABLE 3-continued

Biochemical Activities of p97 Inhibitors

| Structure | ADPGlo IC$_{50}$ (µM) |
|---|---|
| (structure) | 2.4 |
| (structure) | 0.027 |
| (structure) | 3.3 |

TABLE 3-continued
Biochemical Activities of p97 Inhibitors
| Structure | ADPGlo IC$_{50}$ (μM) |
|---|---|
| 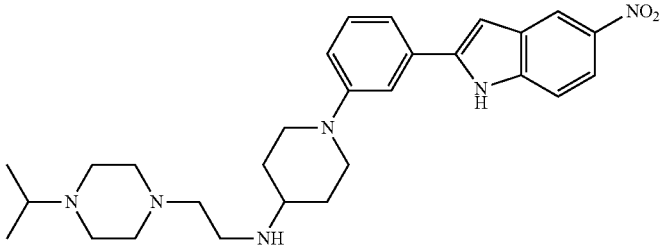 [SMILES: CC(C)N1CCN(CCNC2CCN(c3cccc(-c4cc5cc([N+](=O)[O-])ccc5[nH]4)c3)CC2)CC1] | 0.036 |
| 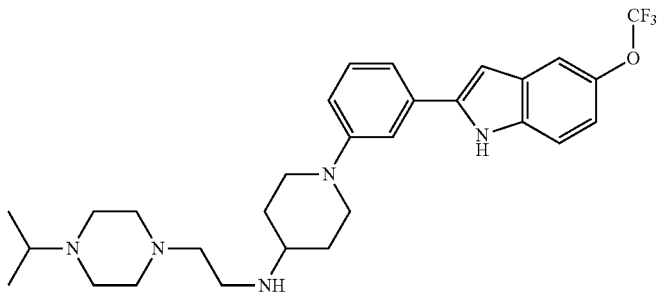 [SMILES: CC(C)N1CCN(CCNC2CCN(c3cccc(-c4cc5cc(OC(F)(F)F)ccc5[nH]4)c3)CC2)CC1] | 3.7 |
| 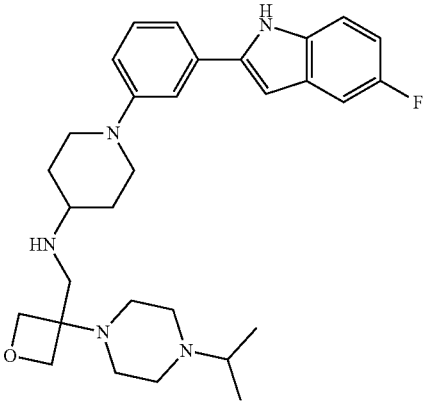 [SMILES: CC(C)N1CCN(C2(CNC3CCN(c4cccc(-c5cc6cc(F)ccc6[nH]5)c4)CC3)COC2)CC1] | 0.041 |
| 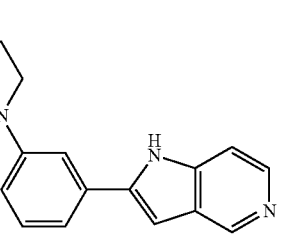 | 3.8 |

TABLE 3-continued

Biochemical Activities of p97 Inhibitors

| Structure | ADPGlo IC$_{50}$ (μM) |
|---|---|
| (structure: 5-cyanoindole-2-yl phenyl linked to piperidine-N, 4-position NH to 1-isopropylpiperidin-4-yl) | 0.047 |
| (structure: 5-fluoroindole-2-yl phenyl linked to piperidine-N; piperidine-4-carboxamide NH-CH$_2$-cyclobutyl-(4-isopropylpiperazin-1-yl)) | 3.8 |
| (structure: 5-fluoroindole-2-yl phenyl linked to piperidine-N, 4-position NH to 1-isopropylpiperidin-4-yl) | 0.049 |

TABLE 3-continued
Biochemical Activities of p97 Inhibitors
| Structure | ADPGlo IC$_{50}$ (μM) |
|---|---|
| 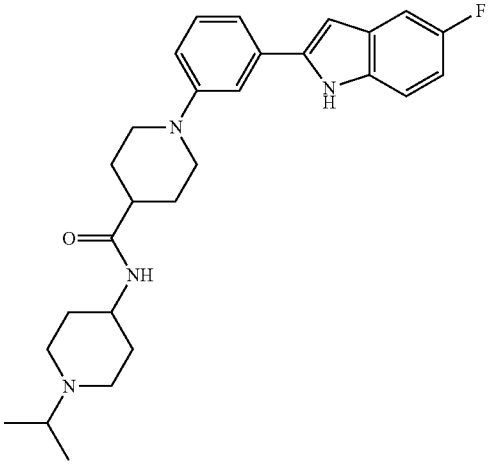 [SMILES: CC(C)N1CCC(NC(=O)C2CCN(c3cccc(-c4cc5cc(F)ccc5[nH]4)c3)CC2)CC1] | 3.9 |
| 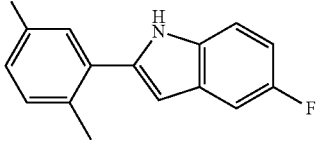 | 0.082 |
| 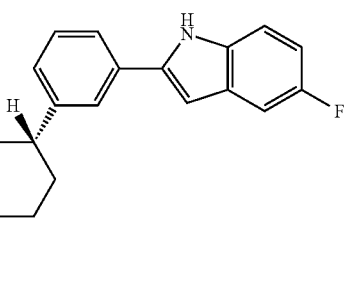 | 4.139 |
| 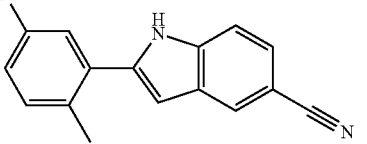 | 0.086 |

TABLE 3-continued
Biochemical Activities of p97 Inhibitors
| Structure | ADPGlo IC$_{50}$ (μM) |
|---|---|
| 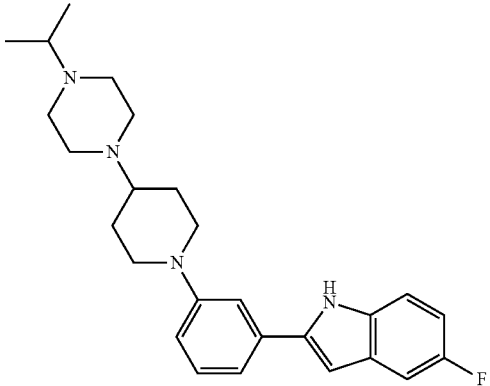 [SMILES: CC(C)N1CCN(C2CCN(c3cccc(-c4cc5cc(F)ccc5[nH]4)c3)CC2)CC1] | 4.3 |
| 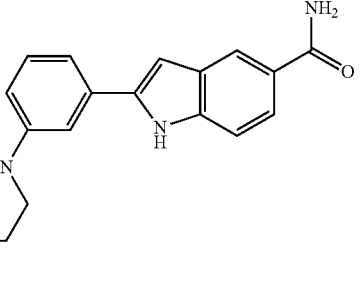 | 0.087 |
| 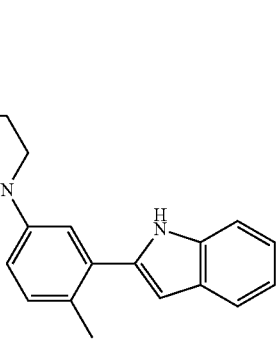 | 4.5 |
| 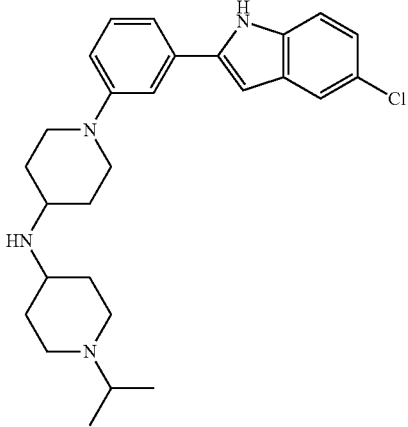 [SMILES: CC(C)N1CCC(NC2CCN(c3cccc(-c4cc5cc(Cl)ccc5[nH]4)c3)CC2)CC1] | 0.092 |

TABLE 3-continued

| Biochemical Activities of p97 Inhibitors | |
|---|---|
| Structure | ADPGlo IC$_{50}$ (μM) |
| 3-(1-isopropylpiperazinyl-ethylamino-piperidinyl-phenyl)-6-nitroindole | 4.6 |
| 3-(1-isopropylpiperazinyl-ethylamino-piperidinyl-phenyl)-5-hydroxyindole | 0.1 |
| 3-(1-isopropylpiperidinyl-amino-piperidinyl-phenyl)-5-cyanoindole | 4.9 |

TABLE 3-continued
Biochemical Activities of p97 Inhibitors
| Structure | ADPGlo IC$_{50}$ (μM) |
|---|---|
| 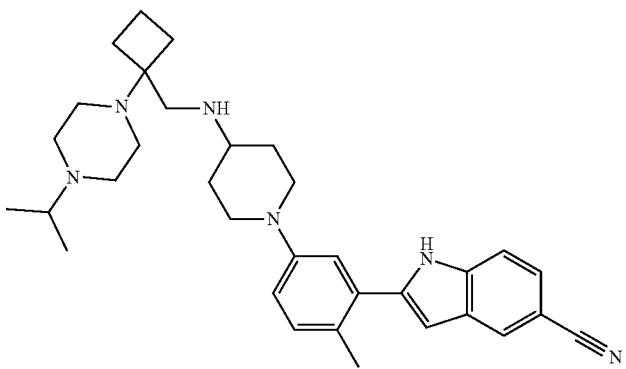 [SMILES: Cc1ccc(N2CCC(NCC3(N4CCN(C(C)C)CC4)CCC3)CC2)cc1-c1cc2cc(C#N)ccc2[nH]1] | 0.1 |
| 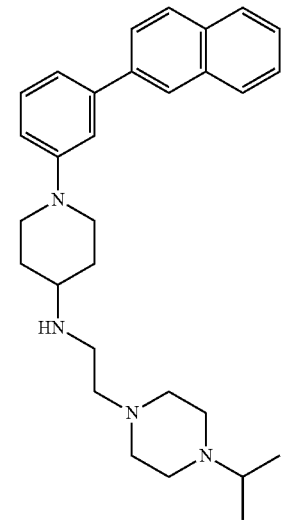 [SMILES: CC(C)N1CCN(CCNC2CCN(c3cccc(-c4ccc5ccccc5c4)c3)CC2)CC1] | 5.1 |
| 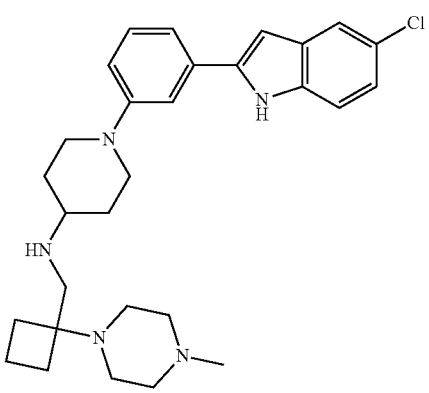 [SMILES: CN1CCN(C2(CNC3CCN(c4cccc(-c5cc6cc(Cl)ccc6[nH]5)c4)CC3)CCC2)CC1] | 0.11 |

TABLE 3-continued
Biochemical Activities of p97 Inhibitors
| Structure | ADPGlo IC$_{50}$ (μM) |
|---|---|
| 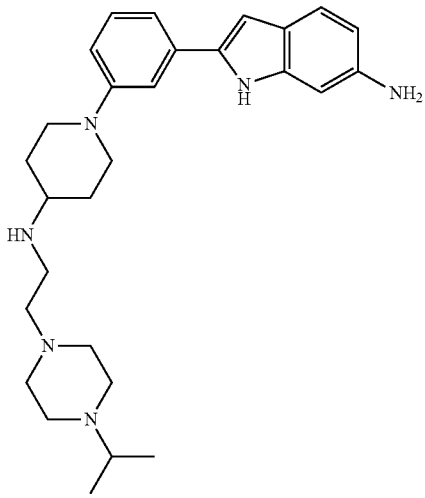 [SMILES: CC(C)N1CCN(CCNC2CCN(c3cccc(-c4cc5ccc(N)cc5[nH]4)c3)CC2)CC1] | 5.2 |
| 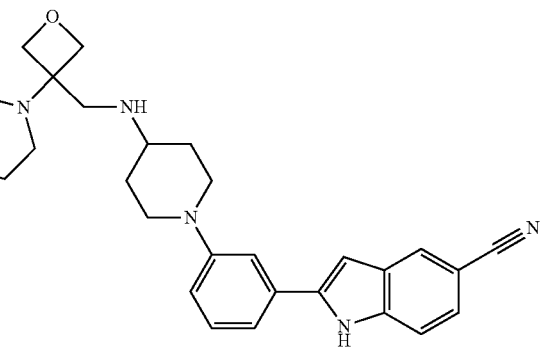 | 0.11 |
| 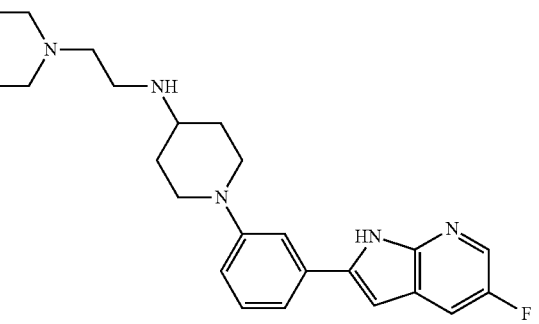 | 5.3 |
| 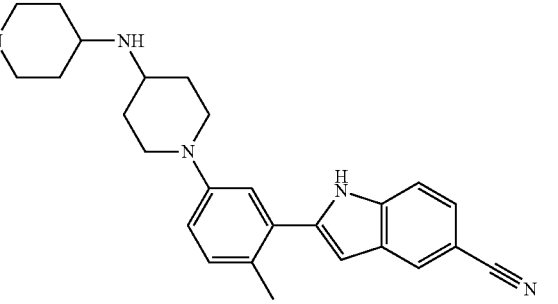 | 0.11 |

TABLE 3-continued
Biochemical Activities of p97 Inhibitors
| Structure | ADPGlo IC$_{50}$ (μM) |
|---|---|
| 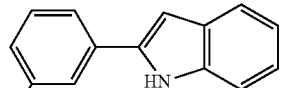 | 5.6 |
| 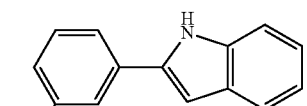 | 0.11 |
| 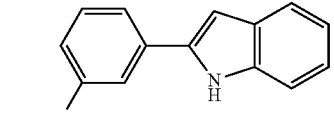 | 5.8 |

TABLE 3-continued
Biochemical Activities of p97 Inhibitors
| Structure | ADPGlo IC$_{50}$ (μM) |
|---|---|
| 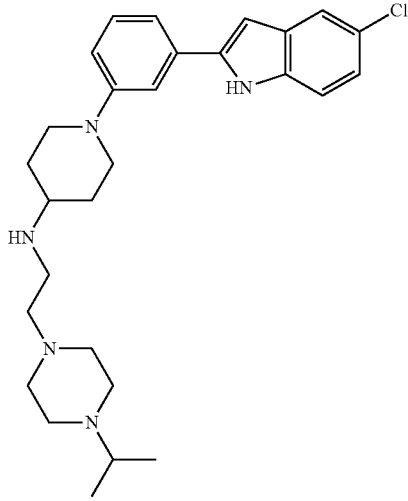 [SMILES: CC(C)N1CCN(CCNC2CCN(c3cccc(-c4cc5cc(Cl)ccc5[nH]4)c3)CC2)CC1] | 0.12 |
| 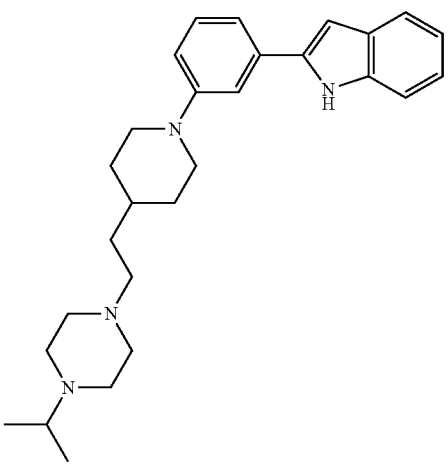 [SMILES: CC(C)N1CCN(CCC2CCN(c3cccc(-c4cc5ccccc5[nH]4)c3)CC2)CC1] | 6 |
| 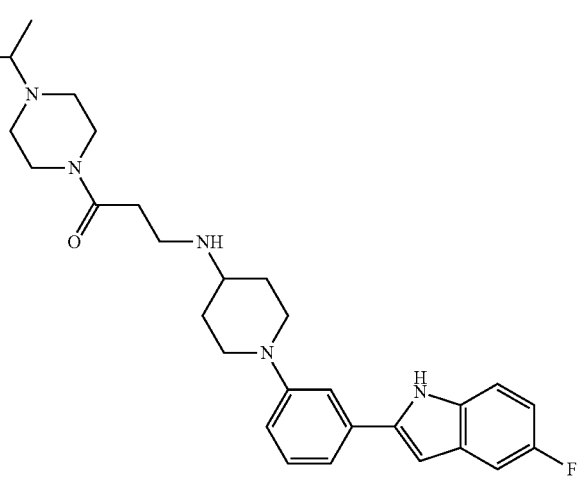 | 0.12 |

TABLE 3-continued
Biochemical Activities of p97 Inhibitors
| Structure | ADPGlo IC$_{50}$ (μM) |
|---|---|
| 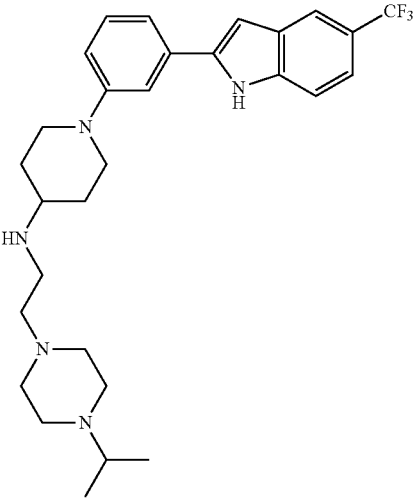 [SMILES: CC(C)N1CCN(CCNC2CCN(c3cccc(-c4cc5cc(C(F)(F)F)ccc5[nH]4)c3)CC2)CC1] | 6 |
| 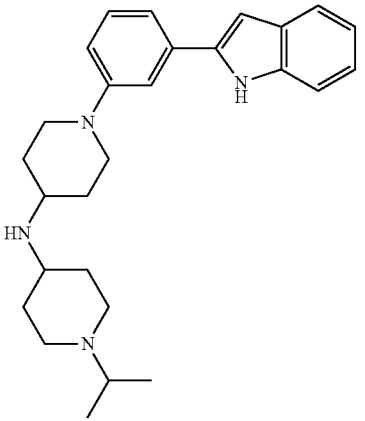 [SMILES: CC(C)N1CCC(NC2CCN(c3cccc(-c4cc5ccccc5[nH]4)c3)CC2)CC1] | 0.13 |
| 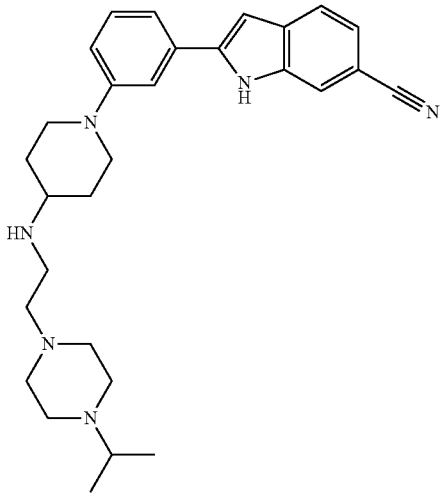 [SMILES: CC(C)N1CCN(CCNC2CCN(c3cccc(-c4cc5ccc(C#N)cc5[nH]4)c3)CC2)CC1] | 6.1 |

TABLE 3-continued

| Biochemical Activities of p97 Inhibitors | |
|---|---|
| Structure | ADPGlo IC$_{50}$ (μM) |
| | 0.13 |
| | 6.2 |
| | 0.13 |

TABLE 3-continued

Biochemical Activities of p97 Inhibitors

| Structure | ADPGlo IC$_{50}$ (µM) |
|---|---|
| 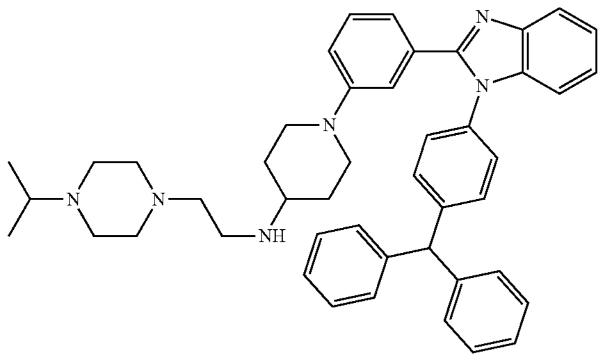 [SMILES: CC(C)N1CCN(CCNC2CCN(c3cccc(-c4nc5ccccc5n4-c4ccc(C(c5ccccc5)c5ccccc5)cc4)c3)CC2)CC1] | 7.1 |
| 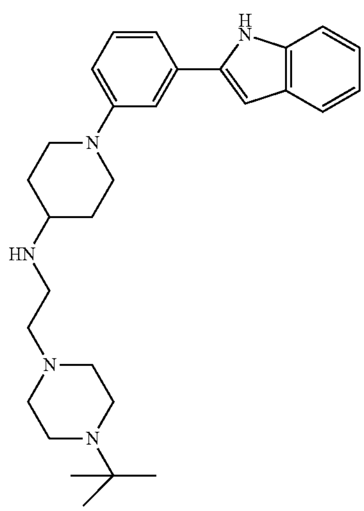 [SMILES: CC(C)(C)N1CCN(CCNC2CCN(c3cccc(-c4cc5ccccc5[nH]4)c3)CC2)CC1] | 0.13 |
| 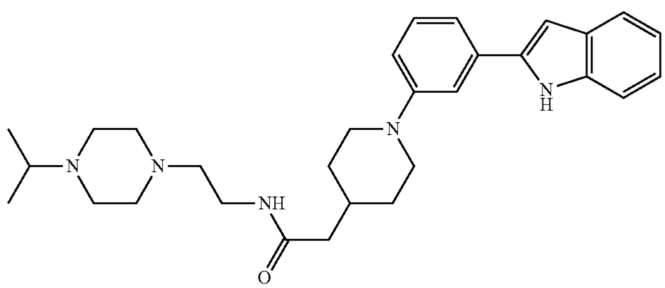 [SMILES: CC(C)N1CCN(CCNC(=O)CC2CCN(c3cccc(-c4cc5ccccc5[nH]4)c3)CC2)CC1] | 7.34 |

TABLE 3-continued
Biochemical Activities of p97 Inhibitors
| Structure | ADPGlo IC$_{50}$ (μM) |
|---|---|
| 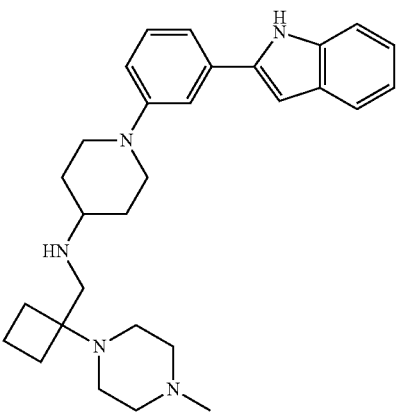 [SMILES: CN1CCN(C2(CNC3CCN(c4cccc(-c5cc6ccccc6[nH]5)c4)CC3)CCC2)CC1] | 0.14 |
| 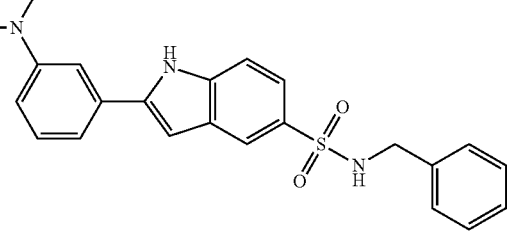 | 7.5 |
| 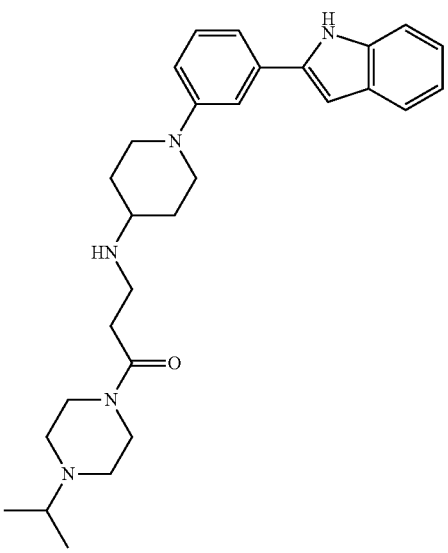 [SMILES: CC(C)N1CCN(C(=O)CCNC2CCN(c3cccc(-c4cc5ccccc5[nH]4)c3)CC2)CC1] | 0.14 |

TABLE 3-continued

| Biochemical Activities of p97 Inhibitors | |
|---|---|
| Structure | ADPGlo IC$_{50}$ ($\mu$M) |
| | 7.58 |
| | 0.14 |
| | 7.6 |

TABLE 3-continued

Biochemical Activities of p97 Inhibitors

| Structure | ADPGlo IC$_{50}$ (μM) |
|---|---|
| (structure: 3-(1H-indol-2-yl)phenyl-piperidin-4-yl-NH-ethyl-(4-isopropyl-1,4-diazepan-1-yl)) | 0.15 |
| (structure: 5-(1H-indol-2-yl)pyridin-3-yl-piperidin-4-yl-NH-ethyl-(4-isopropylpiperazin-1-yl)) | 8 |
| (structure: 4-methylpiperazin-1-yl-C(O)-CH2CH2-NH-piperidin-4-yl-N-phenyl-(5-fluoro-1H-indol-2-yl)) | 0.15 |

TABLE 3-continued

Biochemical Activities of p97 Inhibitors

| Structure | ADPGlo IC$_{50}$ ($\mu$M) |
|---|---|
| (structure) | 8.6 |
| (structure) | 0.15 |
| (structure) | 9.3 |

TABLE 3-continued
| Structure | ADPGlo IC$_{50}$ (μM) |
|---|---|
| 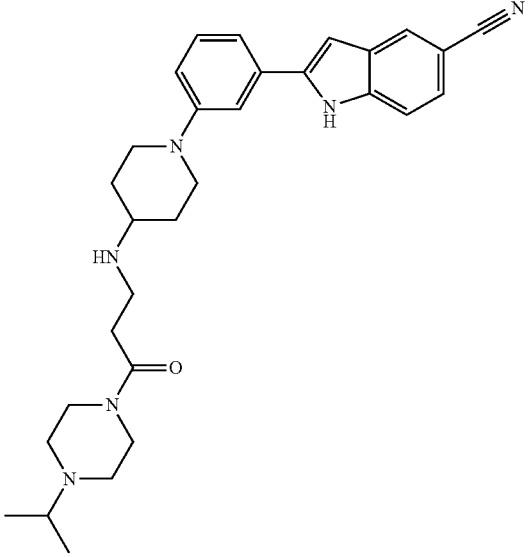 [SMILES: CC(C)N1CCN(C(=O)CCNC2CCN(c3cccc(-c4cc5cc(C#N)ccc5[nH]4)c3)CC2)CC1] | 0.15 |
| 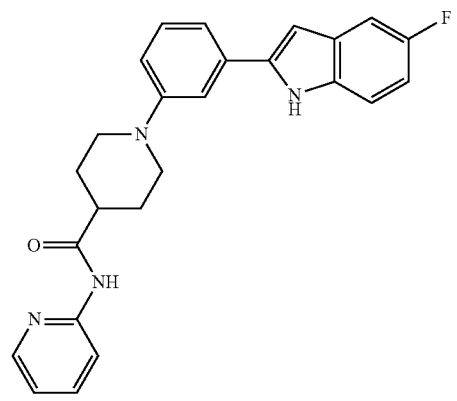 [SMILES: O=C(Nc1ccccn1)C1CCN(c2cccc(-c3cc4cc(F)ccc4[nH]3)c2)CC1] | 9.7 |
| 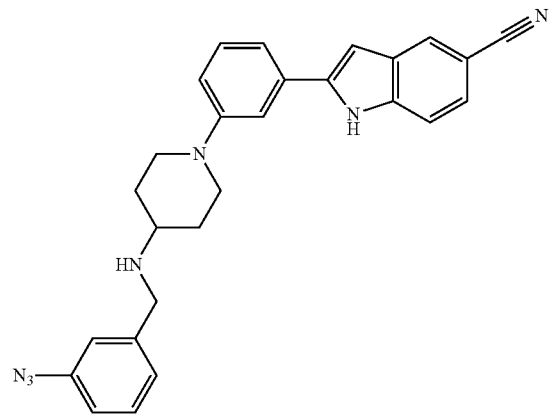 [SMILES: N#Cc1ccc2[nH]c(-c3cccc(N4CCC(NCc5cccc(N=[N+]=[N-])c5)CC4)c3)cc2c1] | 0.16 |

TABLE 3-continued
Biochemical Activities of p97 Inhibitors
| Structure | ADPGlo IC$_{50}$ (μM) |
|---|---|
| 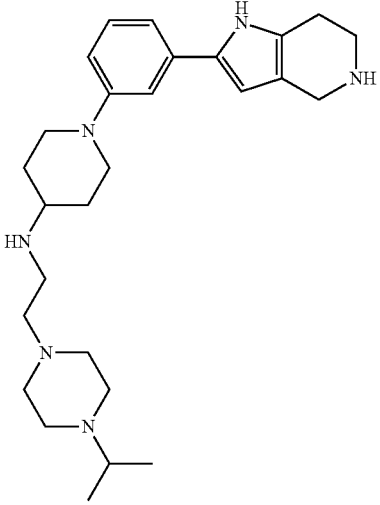 [SMILES: CC(C)N1CCN(CCNC2CCN(c3cccc(-c4cc5c([nH]4)CCNC5)c3)CC2)CC1] | 11 |
| 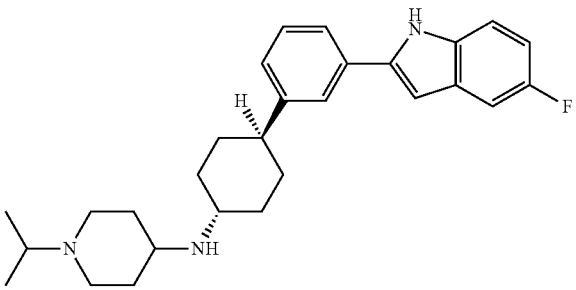 [SMILES: CC(C)N1CCC(N[C@H]2CC[C@H](c3cccc(-c4cc5cc(F)ccc5[nH]4)c3)CC2)CC1] | 0.175 |
| 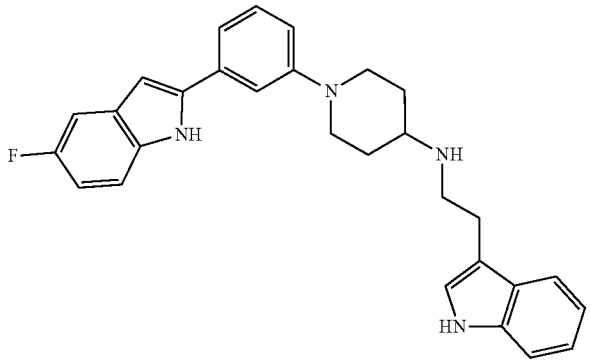 [SMILES: Fc1ccc2[nH]c(-c3cccc(N4CCC(NCCc5c[nH]c6ccccc56)CC4)c3)cc2c1] | 11 |
| 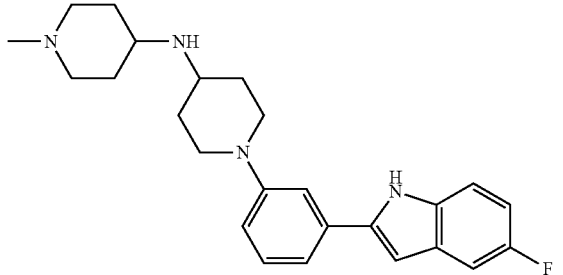 [SMILES: CN1CCC(NC2CCN(c3cccc(-c4cc5cc(F)ccc5[nH]4)c3)CC2)CC1] | 0.18 |

TABLE 3-continued
Biochemical Activities of p97 Inhibitors
| Structure | ADPGlo IC$_{50}$ (µM) |
|---|---|
| 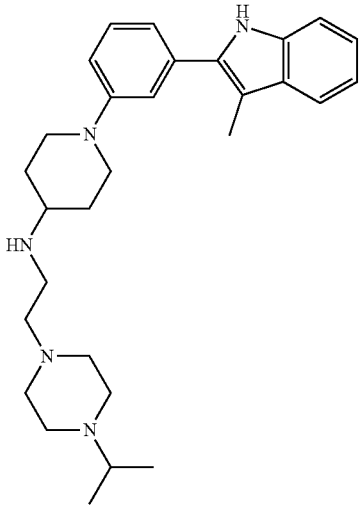 [SMILES: Cc1c(-c2cccc(N3CCC(NCCN4CCN(C(C)C)CC4)CC3)c2)[nH]c2ccccc12] | 12 |
| 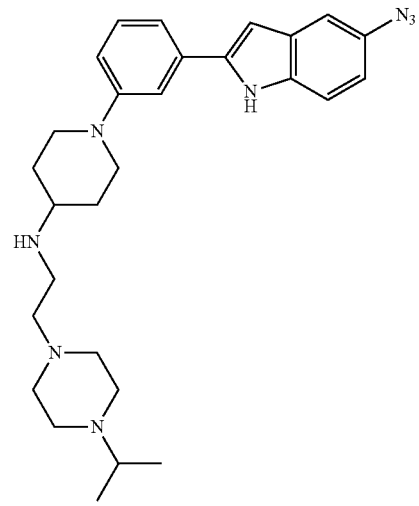 [SMILES: CC(C)N1CCN(CCNC2CCN(c3cccc(-c4cc5cc(N=[N+]=[N-])ccc5[nH]4)c3)CC2)CC1] | 0.2 |
| 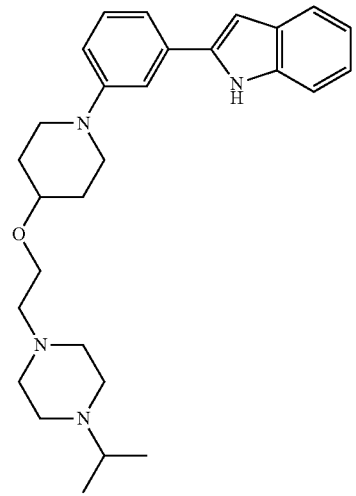 [SMILES: CC(C)N1CCN(CCOC2CCN(c3cccc(-c4cc5ccccc5[nH]4)c3)CC2)CC1] | 12 |

TABLE 3-continued
Biochemical Activities of p97 Inhibitors
| Structure | ADPGlo IC$_{50}$ (µM) |
|---|---|
| 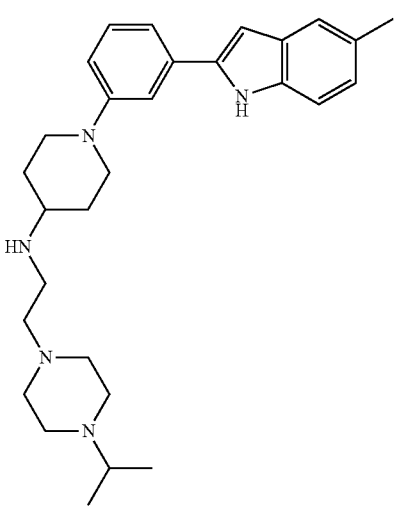 [SMILES: Cc1ccc2[nH]c(-c3cccc(N4CCC(NCCN5CCN(C(C)C)CC5)CC4)c3)cc2c1] | 0.2 |
| 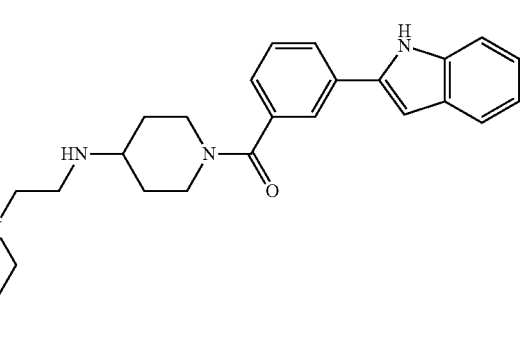 | 13.587 |
| 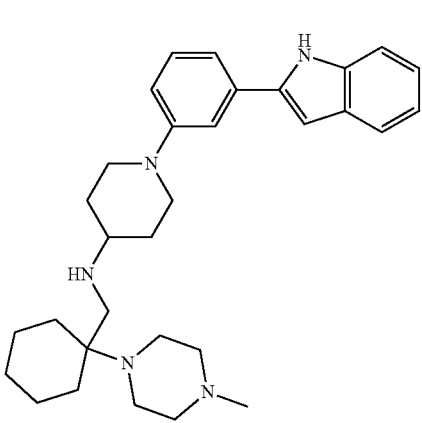 [SMILES: CN1CCN(C2(CNC3CCN(c4cccc(-c5cc6ccccc6[nH]5)c4)CC3)CCCCC2)CC1] | 0.26 |

TABLE 3-continued
Biochemical Activities of p97 Inhibitors
| Structure | ADPGlo IC$_{50}$ (μM) |
|---|---|
| 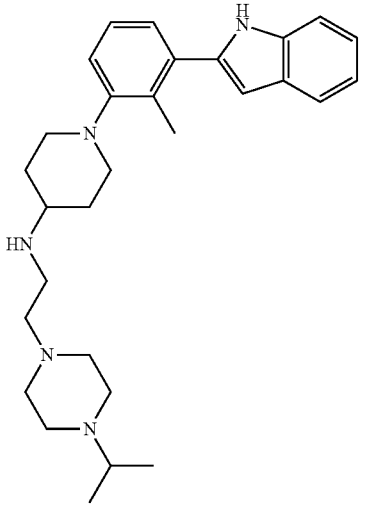 [SMILES: Cc1c(-c2cc3ccccc3[nH]2)cccc1N1CCC(NCCN2CCN(C(C)C)CC2)CC1] | 14 |
| 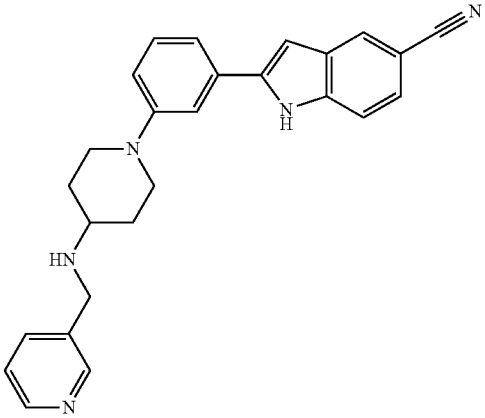 [SMILES: N#Cc1ccc2[nH]c(-c3cccc(N4CCC(NCc5cccnc5)CC4)c3)cc2c1] | 0.29 |
| 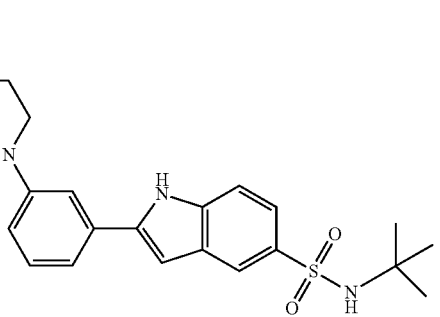 | 14 |

TABLE 3-continued

| Biochemical Activities of p97 Inhibitors | |
|---|---|
| Structure | ADPGlo IC$_{50}$ ($\mu$M) |
| *[structure: 3-(1H-indol-2-yl)phenyl-piperidin-4-yl-NH-CH$_2$CH$_2$-C(O)-N(4-methylpiperazine)]* | 0.29 |
| *[structure: 2HCl salt; 2-methyl-3-(1H-indol-2-yl)phenyl-piperidin-4-yl-NH-(1-methylpiperidin-4-yl)]* | 15 |
| *[structure: 3-(1H-indol-2-yl)phenyl-piperidin-4-yl-NH-CH$_2$CH$_2$-piperazine]* | 0.31 |

TABLE 3-continued
| Biochemical Activities of p97 Inhibitors | |
|---|---|
| Structure | ADPGlo IC$_{50}$ (μM) |
| 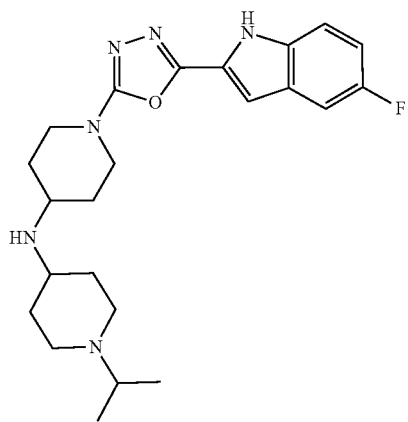 [SMILES: CC(C)N1CCC(NC2CCN(c3nnc(-c4cc5cc(F)ccc5[nH]4)o3)CC2)CC1] | 15.773 |
| 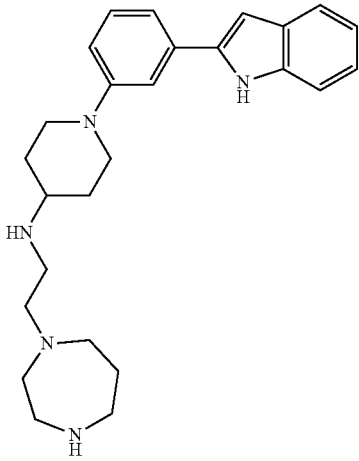 [SMILES: c1cc(-c2cc3ccccc3[nH]2)cc(N2CCC(NCCN3CCCNCC3)CC2)c1] | 0.32 |
| 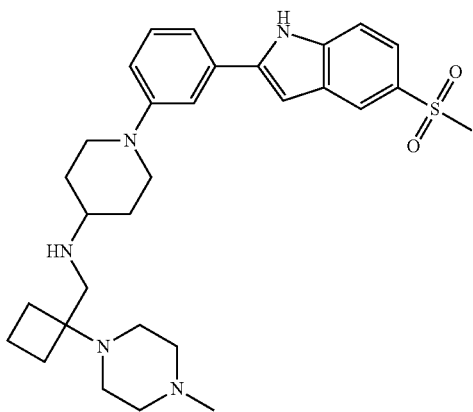 [SMILES: CN1CCN(C2(CNC3CCN(c4cccc(-c5cc6cc(S(C)(=O)=O)ccc6[nH]5)c4)CC3)CCC2)CC1] | 16 |

TABLE 3-continued
Biochemical Activities of p97 Inhibitors
| Structure | ADPGlo IC$_{50}$ (μM) |
|---|---|
| 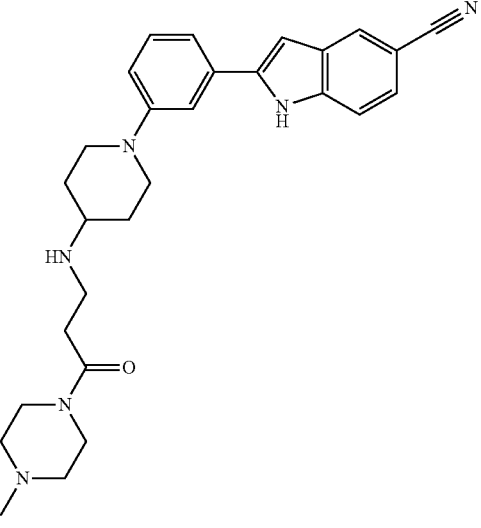 [SMILES: CN1CCN(C(=O)CCNC2CCN(c3cccc(-c4cc5cc(C#N)ccc5[nH]4)c3)CC2)CC1] | 0.32 |
| 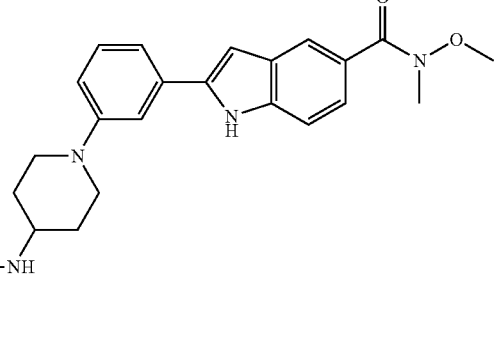 | 16 |
| 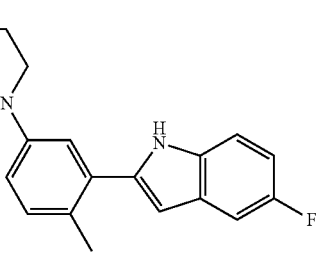 | 0.32 |

TABLE 3-continued

Biochemical Activities of p97 Inhibitors

| Structure | ADPGlo IC$_{50}$ (μM) |
|---|---|
| (structure) | 17 |
| (structure) | 0.33 |
| (structure) | 19 |

TABLE 3-continued

| Biochemical Activities of p97 Inhibitors | |
|---|---|
| Structure | ADPGlo IC$_{50}$ ($\mu$M) |
| *[structure: 5-fluoro-1H-indol-2-yl phenyl connected to piperidine-N, with 4-NH-CH$_2$-pyridin-3-yl]* | 0.34 |
| *[structure: benzofuran-2-yl phenyl connected to piperidine-N, with 4-NH-CH$_2$CH$_2$-(4-isopropylpiperazin-1-yl)]* | 20 |
| *[structure: 2-methylphenyl-(1H-indol-2-yl) connected to piperidine-N, with 4-NH-(1-methylpiperidin-4-yl)]* | 0.35 |

TABLE 3-continued

Biochemical Activities of p97 Inhibitors

| Structure | ADPGlo IC$_{50}$ (μM) |
|---|---|
| 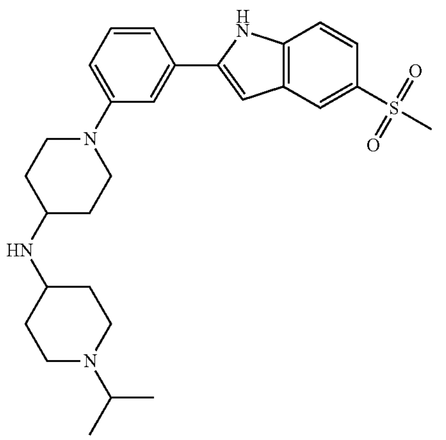 [SMILES: CC(C)N1CCC(NC2CCN(c3cccc(-c4cc5cc(S(C)(=O)=O)ccc5[nH]4)c3)CC2)CC1] | 20 |
| 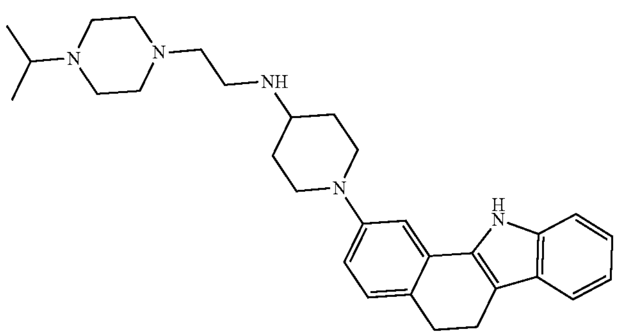 [SMILES: CC(C)N1CCN(CCNC2CCN(c3ccc4c(c3)-c3[nH]c5ccccc5c3CC4)CC2)CC1] | 0.37 |
| 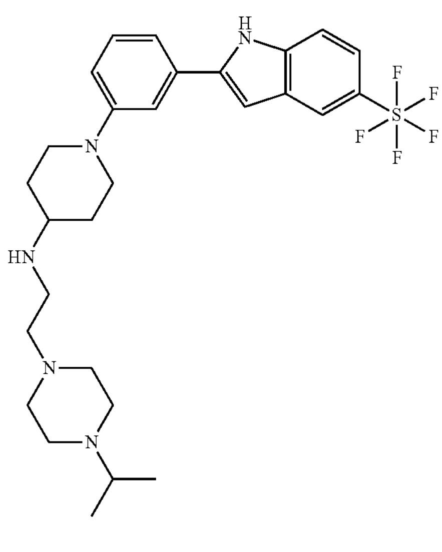 [SMILES: CC(C)N1CCN(CCNC2CCN(c3cccc(-c4cc5cc(S(F)(F)(F)(F)F)ccc5[nH]4)c3)CC2)CC1] | 21 |

TABLE 3-continued

Biochemical Activities of p97 Inhibitors

| Structure | ADPGlo IC$_{50}$ (μM) |
|---|---|
| 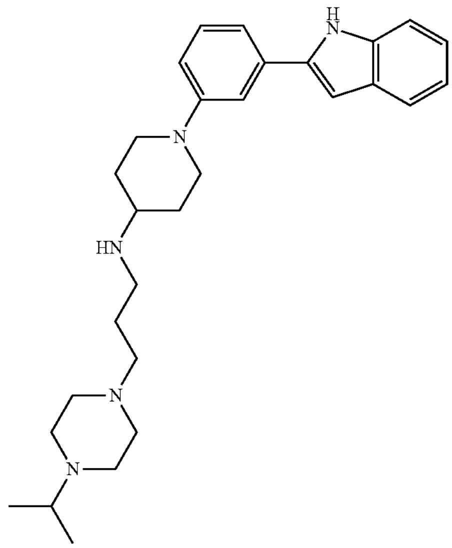 [SMILES: CC(C)N1CCN(CCCNC2CCN(c3cccc(-c4cc5ccccc5[nH]4)c3)CC2)CC1] | 0.37 |
| 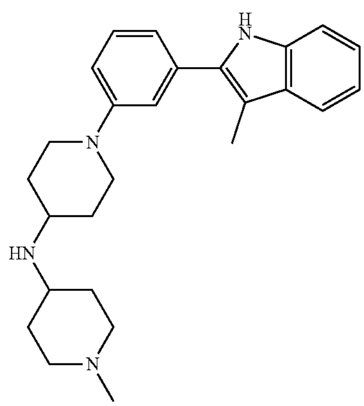 [SMILES: Cc1c(-c2cccc(N3CCC(NC4CCN(C)CC4)CC3)c2)[nH]c2ccccc12] | 22 |
| 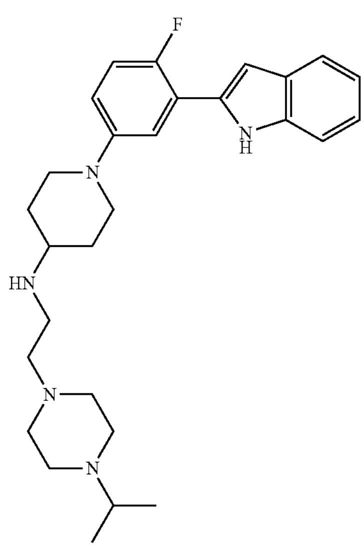 [SMILES: CC(C)N1CCN(CCNC2CCN(c3ccc(F)c(-c4cc5ccccc5[nH]4)c3)CC2)CC1] | 0.41 |

TABLE 3-continued
Biochemical Activities of p97 Inhibitors
| Structure | ADPGlo IC$_{50}$ (μM) |
|---|---|
| 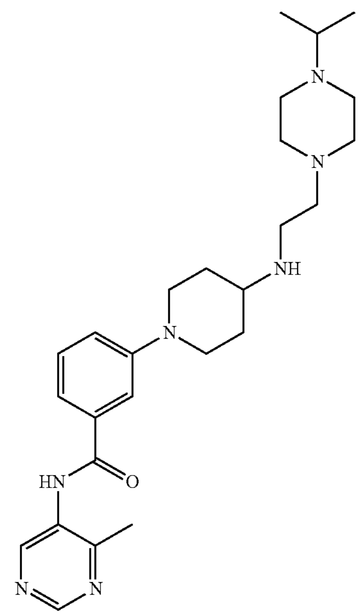 [SMILES: Cc1ncncc1NC(=O)c1cccc(N2CCC(NCCN3CCN(C(C)C)CC3)CC2)c1] | 23 |
| 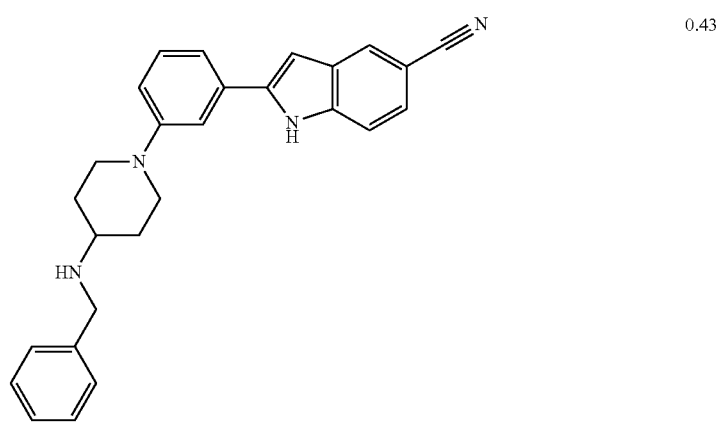 | 0.43 |

TABLE 3-continued
Biochemical Activities of p97 Inhibitors
| Structure | ADPGlo IC$_{50}$ (μM) |
|---|---|
| 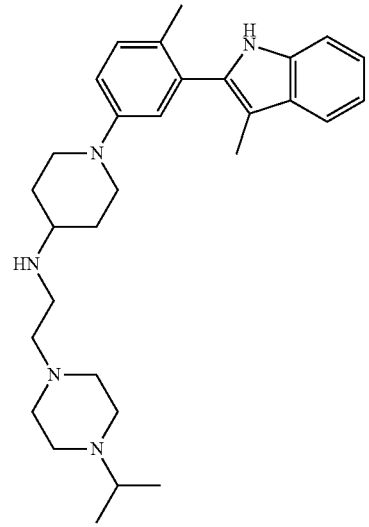 [SMILES: Cc1ccc(N2CCC(NCCN3CCN(C(C)C)CC3)CC2)cc1-c1[nH]c2ccccc2c1C] | 23 |
| 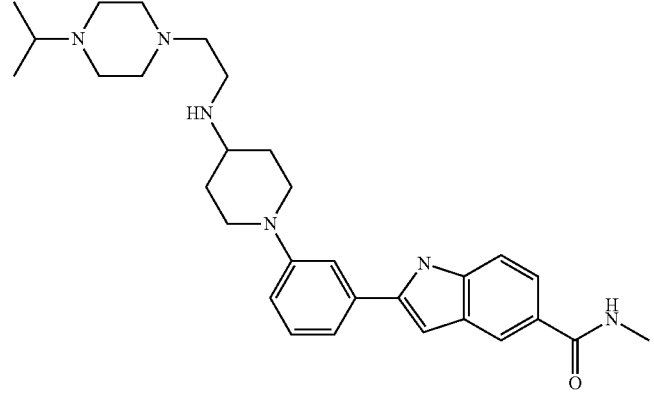 [SMILES: CNC(=O)c1ccc2[nH]c(-c3cccc(N4CCC(NCCN5CCN(C(C)C)CC5)CC4)c3)cc2c1] | 0.43 |
| 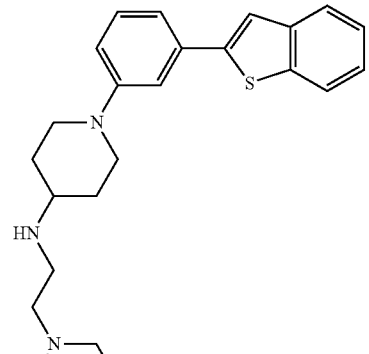 | 24 |

TABLE 3-continued

Biochemical Activities of p97 Inhibitors

| Structure | ADPGlo IC$_{50}$ (μM) |
|---|---|
| (structure) | 0.44 |
| (structure) | 25 |
| (structure) | 0.46 |
| (structure) | 0.5 |

Additional Embodiments

E1. A compound having the structure of formula (I):

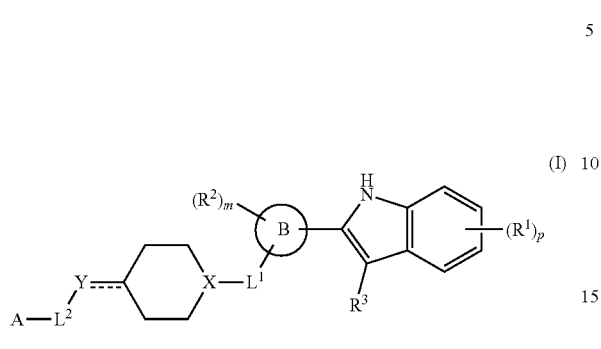

or a pharmaceutically acceptable salt thereof, wherein:

$R^1$ is H, D, halo, cyano, hydroxyl, nitro, —C(O)NR$^5$R$^6$, —C(O)OR$^5$, —N=N$^+$=N$^-$, an optionally substituted $C_1$-$C_3$ alkyl, an optionally substituted $C_1$-$C_3$ alkoxy, —S(O)$_2$NR$^5$R$^6$, an optionally substituted 6-10 membered aryl, an optionally substituted 5-10 membered heteroaryl, —S(O)$_2$R$^5$, —OCZ$_3$, —OCHZ$_2$, —OCH$_2$Z, —SZ$_3$, —SCZ$_3$, or —S(Z)$_5$;

each of $R^5$ or $R^6$ is independently H, D, an optionally substituted $C_1$-$C_5$ alkyl, an optionally substituted $C_1$-$C_3$ alkoxy, or $R^5$ and $R^6$, together with the intervening atoms to which they are attached, can form a 5-6 membered ring;

Z is a halo;

ring B is 6-10 membered aryl, a 5-10 membered heteroaryl, or a 5-10 membered heterocyclyl;

$R^2$ is H, D, halo, cyano, or an optionally substituted $C_1$-$C_3$ alkyl;

m is 0, 1, 2, 3, or 4;

$R^3$ is H, D, or an optionally substituted $C_1$-$C_3$ alkyl; or $R^2$ and $R^3$, together with the intervening atoms to which they are attached, can form a 5-6 membered ring;

$L^1$ is a bond; —C(O)—; —C(O)O—; —OC(O)—; —NR$^5$C(O)NR$^6$—; —NR$^5$C(O)O—; —C(O)NR$^6$—; —S(O)—; or —S(O)$_2$—;

X is CH or N;

Y is a bond, CH, CH$_2$, CH$_3$, N, NH, NH$_2$, O, or S;

$L^2$ is a bond, an optionally substituted $C_1$-$C_5$ alkyl, or an optionally substituted 3-10 membered cycloalkyl;

A is —NR$^{10}$R$^{10}$, —C(O)OR$^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl;

each $R^{10}$ independently is H, an optionally substituted $C_1$-$C_3$ alkyl, an optionally substituted 5-7 membered heteroaryl, or an optionally substituted 6-10 membered aryl;

p is 0, 1, 2, 3, or 4; and

 denotes a single or double bond;

wherein the compound is not:

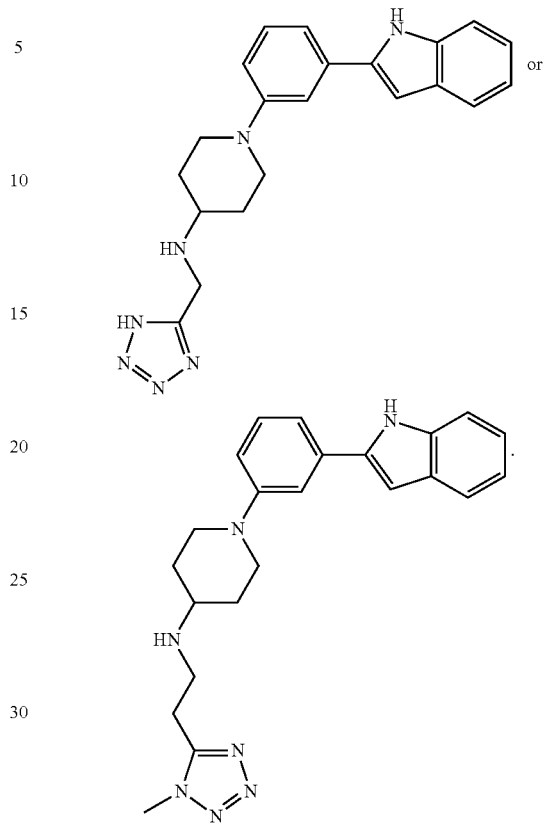

E2. The compound of E1, wherein X is N.
E3. The compound of one of E1-E2, wherein Y is NH.
E4. The compound of any of E1-E3, wherein A is a 5-10 membered heterocyclyl.
E5. The compound of any of E1-E4, wherein at least one ring heteroatom of A is N.
E6. The compound of any of E1-E5, wherein A has the structure:

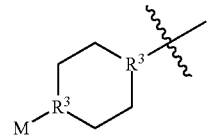

wherein each $R^3$ is independently CH or N and M is an optionally substituted $C_1$-$C_6$ alkyl.

E7. The compound of E6, wherein A has the structure:

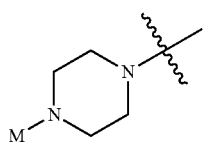

E8. The compound of any of E1-E7, wherein M is a $C_1$-$C_3$ alkyl.
E9. The compound of any of E1-E8, wherein $L^2$ is an optionally substituted $C_1$-$C_3$ alkyl.

E10. The compound of any of E1-E9, wherein $L^2$ is an optionally substituted $C_2$ alkyl.

E11. The compound of any of E1-E10, wherein $R^1$ is halo, cyano, $N(O)_2$, hydroxyl, or —C(O)$NR^5R^6$.

E12. The compound of any of E1-E11, wherein p is 0.

E13. A compound of formula (I), selected from the group consisting of the compounds of Table 1, or a pharmaceutically acceptable salt thereof.

E14. A pharmaceutical composition comprising a compound of any of E1-E12 and at least one pharmaceutically acceptable excipient.

E15. A pharmaceutical composition comprising a compound of E13 and at least one pharmaceutically acceptable excipient.

E16. A method of inhibiting p97 in a subject in need thereof, comprising administering to the subject a therapeutically effective amount of a compound of formula II or a therapeutically effective amount of a pharmaceutical composition comprising a compound of formula II and at least one pharmaceutically acceptable excipient:

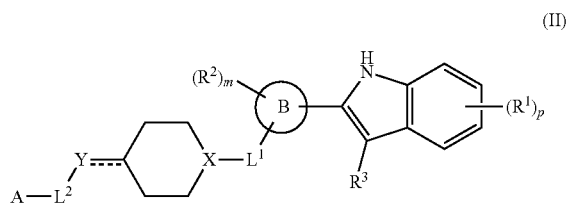

(II)

or a pharmaceutically acceptable salt thereof, wherein:
$R^1$ is H, D, halo, cyano, hydroxyl, nitro, —C(O)$NR^5R^6$, —C(O)$OR^5$, —N=$N^+$=$N^-$, an optionally substituted $C_1$-$C_3$ alkyl, an optionally substituted $C_1$-$C_3$ alkoxy, —S(O)$_2NR^5R^6$, an optionally substituted 6-10 membered aryl, an optionally substituted 5-10 membered heteroaryl, —S(O)$_2R^5$, —OCZ$_3$, —OCHZ$_2$, —OCH$_2$Z, —SZ$_3$, —SCZ$_3$, or S(Z)$_5$;
each of $R^5$ or $R^6$ is independently H, D, an optionally substituted $C_1$-$C_5$ alkyl, an optionally substituted $C_1$-$C_3$ alkoxy, or $R^5$ and $R^6$, together with the intervening atoms to which they are attached, can form a 5-6 membered ring;
Z is a halo;
ring B is a 6-10 membered aryl, a 5-10 membered heteroaryl, or a 5-10 membered heterocyclyl;
$R^2$ is H, D, halo, cyano, or an optionally substituted $C_1$-$C_3$ alkyl;
m is 0, 1, 2, 3, or 4;
$R^3$ is H, D, or an optionally substituted $C_1$-$C_3$ alkyl; or $R^2$ and $R^3$, together with the intervening atoms to which they are attached, can form a 5-6 membered ring
$L^1$ is a bond; —C(O)—; —C(O)O—; —OC(O)—; —$NR^5$C(O)$NR^6$—; —$NR^5$C(O)O—; —C(O)$NR^6$—; —S(O)—; or —S(O)$_2$—;
X is CH or N;
Y is a bond, CH, CH$_2$, CH$_3$, N, NH, NH$_2$, O, or S;
$L^2$ is a bond, an optionally substituted $C_1$-$C_5$ alkyl, or an optionally substituted 3-10 membered cycloalkyl;
A is —$NR^{10}R^{10}$, —C(O)$OR^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl; each $R^{10}$ independently is H, an optionally substituted $C_1$-$C_3$ alkyl, an optionally substituted 5-7 membered heteroaryl, or an optionally substituted 6-10 membered aryl;

p is 0, 1, 2, 3, or 4; and

⫽ denotes a single or double bond.

E17. A method of treating cancer or a neurodegenerative disease susceptible to treatment by p97 inhibition in a subject in need thereof comprising administering to the subject a therapeutically effective amount of a compound of formula II or a therapeutically effective amount of a pharmaceutical composition comprising a compound of formula II and at least one pharmaceutically acceptable excipient:

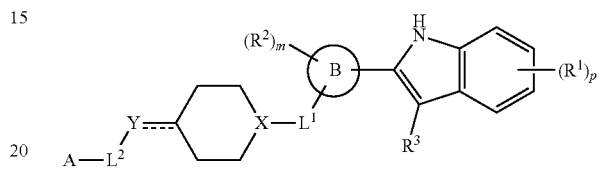

(II)

or a pharmaceutically acceptable salt thereof, wherein:
$R^1$ is a H, D, halo, cyano, hydroxyl, nitro, —C(O)$NR^5R^6$, —C(O)$OR^5$, —N=$N^+$=$N^-$, an optionally substituted $C_1$-$C_3$ alkyl, an optionally substituted $C_1$-$C_3$ alkoxy, —S(O)$_2NR^5R^6$, an optionally substituted 6-10 membered aryl, an optionally substituted 5-10 membered heteroaryl, —S(O)$_2R^5$, —OCZ$_3$, —OCHZ$_2$, —OCH$_2$Z, —SZ$_3$, —SCZ$_3$, or S(Z)$_5$;
each of $R^5$ or $R^6$ is independently H, D, an optionally substituted $C_1$-$C_5$ alkyl, an optionally substituted $C_1$-$C_3$ alkoxy, or $R^5$ and $R^6$, together with the intervening atoms to which they are attached, can form a 5-6 membered ring;
Z is a halo;
ring B is a 6-10 membered aryl, a 5-10 membered heteroaryl, or a 5-10 membered heterocyclyl;
$R^2$ is H, D, halo, cyano, or an optionally substituted $C_1$-$C_3$ alkyl;
m is 0, 1, 2, 3, or 4;
$R^3$ is H, D, or an optionally substituted $C_1$-$C_3$ alkyl; or $R^2$ and $R^3$, together with the intervening atoms to which they are attached, can form a 5-6 membered ring
$L^1$ is a bond; —C(O)—; —C(O)O—; —OC(O)—; —$NR^5$C(O)$NR^6$—; —$NR^5$C(O)O—; —C(O)$NR^6$—; —S(O)—; or —S(O)$_2$—;
X is CH or N;
Y is a bond, CH, CH$_2$, CH$_3$, N, NH, NH$_2$, O, or S;
$L^2$ is a bond, an optionally substituted $C_1$-$C_5$ alkyl, or an optionally substituted 3-10 membered cycloalkyl;
A is —$NR^{10}R^{10}$, —C(O)$OR^{10}$, an optionally substituted $C_1$-$C_5$ alkyl, an optionally substituted 4-10 membered heterocyclyl, an optionally substituted 5-10 membered heteroaryl, an optionally substituted 6-10 membered aryl, or an optionally substituted 4-7 membered cycloalkyl;
each $R^{10}$ independently is H, an optionally substituted $C_1$-$C_3$ alkyl, an optionally substituted 5-7 membered heteroaryl, or an optionally substituted 6-10 membered aryl;
p is 0, 1, 2, 3, or 4; and ⫽ denotes a single or double bond.

E18. A method of inhibiting p97 in a subject in need thereof, comprising administering to the subject a therapeutically effective amount of a compound of any one of E1-16 or a therapeutically effective amount of a pharmaceutical composition of E14 or E15.

E19. A method of treating cancer or a neurodegenerative disease susceptible to treatment by p97 inhibition in a subject in need thereof comprising administering to the subject a therapeutically effective amount of a compound of any one of E1-E13 or a therapeutically effective amount of E14 or E15.

E20. The method of any one of E17-E19, wherein the cancer susceptible to treatment by p97 inhibition is selected from the group consisting of a solid tumor, non-small cell lung carcinoma, multiple myeloma, and mantle cell lymphoma.

E21. The method of any one of E17-E19, wherein the neurodegenerative disease susceptible to treatment is selected from the group consisting of inclusion body myopathy (IBM), Paget's disease of the bone (PDB), frontotemporal dementia (FTD) and amyotrophic lateral sclerosis (ALS).

The invention claimed is:

1. A method of inhibiting p97 in a subject, comprising administering to the subject a therapeutically effective amount of a compound of formula II or a therapeutically effective amount of a pharmaceutical composition comprising a compound of formula II and at least one pharmaceutically acceptable excipient:

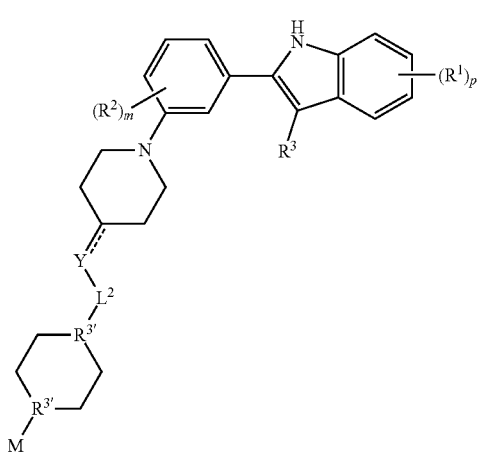

(II)

or a pharmaceutically acceptable salt thereof, wherein:
$R^1$ is H, D, halo, cyano, hydroxyl, nitro, —C(O)NR$^5$R$^6$, —C(O)OR$^5$, —N=N$^+$=N$^-$, $C_1$-$C_3$ alkyl, $C_1$-$C_3$ alkoxy, —S(O)$_2$NR$^5$R$^6$, —S(O)$_2$R$^5$, —OCZ$_3$, —OCHZ$_2$, —OCH$_2$Z, —SZ$_3$, —SCZ$_3$, or S(Z)$_5$;
each of $R^5$ or $R^6$ is independently H, D, $C_1$-$C_5$ alkyl, or $C_1$-$C_3$ alkoxy optionally substituted with one or more halo;
Z is a halo;
$R^2$ is H, D, halo, cyano, $C_1$-$C_3$ alkyl optionally substituted with one or more halo;
m is 0, 1, 2, 3, or 4;
$R^3$ is H, D, or $C_1$-$C_3$ alkyl optionally substituted by one or more halo;
each $R^{3'}$ is independently CH or N, and at least one $R^{3'}$ is N;
M is $C_1$-$C_6$ alkyl;
Y is a bond, CH, CH$_2$, N, NH, O, or S;
$L^2$ is $C_1$-$C_5$ alkyl optionally further including a cycloalkyl group or optionally substituted with one or more oxo;

p is 0, 1, 2, 3, or 4; and

⟋⟋ denotes a single or double bond.

2. A method of treating non-small cell lung carcinoma in a subject,
the method comprising administering to the subject a therapeutically effective amount of a compound of formula II or a therapeutically effective amount of a pharmaceutical composition comprising a compound of formula II and at least one pharmaceutically acceptable excipient:

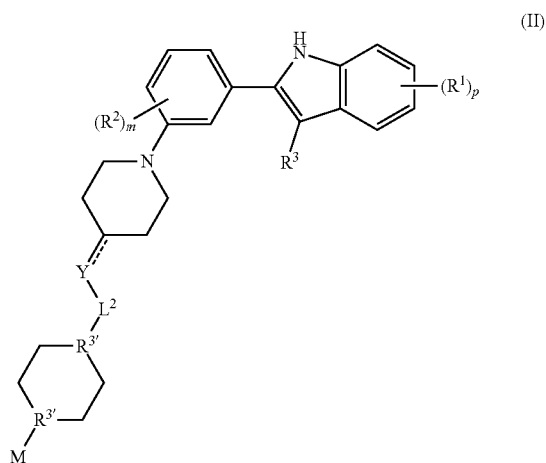

(II)

or a pharmaceutically acceptable salt thereof, wherein:
$R^1$ is H, D, halo, cyano, hydroxyl, nitro, —C(O)NR$^5$R$^6$, —C(O)OR$^5$, —N=N$^+$=N$^-$, $C_1$-$C_3$ alkyl, $C_1$-$C_3$ alkoxy, —S(O)$_2$NR$^5$R$^6$, —S(O)$_2$R$^5$, —OCZ$_3$, —OCHZ$_2$, —OCH$_2$Z, —SZ$_3$, —SCZ$_3$, or S(Z)$_5$;
each of $R^5$ or $R^6$ is independently H, D, $C_1$-$C_5$ alkyl, or $C_1$-$C_3$ alkoxy optionally substituted with one or more halo;
Z is a halo;
$R^2$ is H, D, halo, cyano, $C_1$-$C_3$ alkyl optionally substituted with one or more halo;
m is 0, 1, 2, 3, or 4;
$R^3$ is H, D, or $C_1$-$C_3$ alkyl optionally substituted by one or more halo;
each $R^{3'}$ is independently CH or N, and at least one $R^{3'}$ is N;
M is $C_1$-$C_6$ alkyl;
Y is a bond, CH, CH$_2$, N, NH, O, or S;
$L^2$ is $C_1$-$C_5$ alkyl optionally further including a cycloalkyl group or optionally substituted with one or more oxo,
p is 0, 1, 2, 3, or 4; and ⟋⟋ denotes a single or double bond.

3. The method of claim 1 or 2, wherein $R^1$ is H, D, halo, cyano, hydroxyl, nitro, or —N=N$^+$=N$^-$.

4. The method of claim 1 or 2, wherein M is a $C_1$-$C_3$ alkyl.

5. The method of claim 1 or 2, wherein both $R^{3'}$ are N.

6. The method of claim 1 or 2, wherein $L^2$ is a $C_2$ alkyl.

7. The method of claim 1 or 2, wherein $R^1$ is halo, cyano, N(O)$_2$, hydroxyl, or —C(O)NR$^5$R$^6$.

8. The method of claim 1 or 2, wherein p=0.

* * * * *